(12) United States Patent
Baranowitz

(10) Patent No.: US 12,226,392 B2
(45) Date of Patent: *Feb. 18, 2025

(54) PREVENTION AND TREATMENT OF VIRAL INFECTIONS

(71) Applicant: Steven Baranowitz, Wyncote, PA (US)

(72) Inventor: Steven Baranowitz, Wyncote, PA (US)

( * ) Notice: Subject to any disclaimer, the term of this patent is extended or adjusted under 35 U.S.C. 154(b) by 43 days.

This patent is subject to a terminal disclaimer.

(21) Appl. No.: 18/096,182

(22) Filed: Jan. 12, 2023

(65) Prior Publication Data

US 2024/0033245 A1   Feb. 1, 2024

Related U.S. Application Data

(60) Continuation of application No. 17/089,020, filed on Nov. 4, 2020, now Pat. No. 11,590,099, which is a division of application No. 16/793,066, filed on Feb. 18, 2020, now Pat. No. 10,874,632, which is a continuation of application No. 16/502,150, filed on Jul. 3, 2019, now Pat. No. 10,603,299, which is a continuation-in-part of application No. 16/201,205, filed on Nov. 27, 2018, now Pat. No. 10,383,852, which is a continuation-in-part of application No. PCT/US2017/035150, filed on May 31, 2017.

(60) Provisional application No. 62/344,591, filed on Jun. 2, 2016.

(51) Int. Cl.

| A61K 31/24 | (2006.01) |
| A61K 31/34 | (2006.01) |
| A61K 31/343 | (2006.01) |
| A61K 31/65 | (2006.01) |
| A61P 31/14 | (2006.01) |

(52) U.S. Cl.
CPC .............. *A61K 31/343* (2013.01); *A61P 31/14* (2018.01)

(58) Field of Classification Search
CPC ......... A61K 31/24; A61K 31/34; A61K 31/65
USPC ................................. 514/152, 153, 470, 538
See application file for complete search history.

(56) References Cited

U.S. PATENT DOCUMENTS

| 4,727,069 | A | 2/1988 | Nelson et al. |
| 4,748,173 | A | 5/1988 | Nelson et al. |
| 4,753,935 | A | 6/1988 | Nelson et al. |
| 4,861,776 | A | 8/1989 | Nelson et al. |
| 5,389,879 | A | 2/1995 | Pulyer |
| 5,441,953 | A | 8/1995 | Sjogren |
| 5,444,072 | A | 8/1995 | Patterson et al. |
| 5,493,030 | A | 2/1996 | Morgans et al. |
| 5,536,747 | A | 7/1996 | Patterson et al. |
| 5,538,969 | A | 7/1996 | Morgans et al. |
| 5,554,612 | A | 9/1996 | Patterson et al. |
| 5,633,279 | A | 5/1997 | Morgans et al. |
| 5,688,529 | A | 11/1997 | Lidgate et al. |
| 10,383,852 | B2 | 8/2019 | Baranowitz |
| 10,603,299 | B2 | 3/2020 | Baranowitz |
| 10,874,632 | B2 | 12/2020 | Baranowitz |
| 11,590,099 | B2 | 2/2023 | Baranowitz |
| 2015/0031686 | A1 | 1/2015 | Zhong et al. |

FOREIGN PATENT DOCUMENTS

| WO | 03101199 A1 | 12/2003 |
| WO | 2023150067 A1 | 8/2023 |

OTHER PUBLICATIONS

Baranowitz, Steven, Treatment of Covid-19 with Minocycline and a Guanosine-Restricted Diet: Case Report, Dec. 23, 2020.
Cao, S. et al., "Mycophenolic Acid, Mycophenolate Mofetil, Mizorbine, Ribavirnin, and 7-Nitcindole Inhibit Propagalion of Babesia Parasites by Targeting Inosine 5-Monophosphage Dehydrogenase" Journal of Parasitology, 2014, 100(4) pp. 522-526.
Eugul et al., "Lymphocyte-Selective Cytostatic and immunosuppressive Effects of Mycophenolic Acid in vitro: Role of Deoxyguanosine Nucelotide Deletion" Scand. J. Immuno 33, 1991, pp. 161-173.
Gong, M. et al., "Antiviral effects of selected IMPD and DHODH inhibitors against foot and mouth disease virus" Biomedicine & Pharmacotherapy, 2019, Elsevier.
Heredia, A. et al., "Abacavir in Combination with the Inosine Monophosphate Dehydrogenase (MDPH-Inhibitor Mycophenolic Acid is Active Against Multidrug Resistant HIV-1", Journal of Acquired Immune Deficiency Syndromes, 1999, vol. 22, pp. 406-412.
International Preliminary Report on Patentability re International Application No. PCT/US2017/035150 issued on Dec. 4, 2018.
Karuppannan, A. et al. "Natural compounds inhibiting the replication of Porcine reproductive and respiratory syndrome virus", 2012, Antivirial Research, pp. 188-194.
Kitchin, J.E.S. et al., "Rediscovering mycophenolic acid: A review of its mechanism, side effects, and potential uses", Journal of the American Academy of Dermatology, 1997, vol. 37, pp. 445-449.
Krajczyk, A. et al., "Antivirally active ribavirin analogues-4.5-disubstituted 1,23,-triazole nucleosides; biological evaluation against certain respiratory viruses and computational modeling", Antiviral Chemistry & Chemotherapy, 2014, vol. 23, pp. 161-171.
Markland, W. et al., "Broad spectrum Antiviral Activity of the IMP Dehydrogenase Inhibitor VX-497; a Comparsion with ribavirin and demonstration of Antiviral Additivity with Alpha Interferon", Antimicrobial Agents an Chemotherapy 2000, vol. 44(4), pp. 859-866.
Michaels et al., "Minocycline inhibits West Nile virus replication and apoptosis in human neuron cells" Journal Antimicrobial Chemotherapy, 2007, 60, pp. 981-986.
Montefiori et al., "Selective antiviral activity of synthetic soluble L-tyrosine and L-dopa melanins against human immunodeficiency virus in virt" Antiviral Research 15, 1991, pp. 11-26.

(Continued)

*Primary Examiner* — Raymond J Henley, III
(74) *Attorney, Agent, or Firm* — Joseph F. Murphy; Potomac Law Group, PLLC

(57) ABSTRACT

The present disclosure targets West Nile virus, Respiratory Syncytial Virus, and other disease-causing microbes, including viruses, bacteria, fungi, and parasites. It does this using agents and methods with little toxicity compared to existing therapies.

8 Claims, No Drawings

(56) References Cited

OTHER PUBLICATIONS

Shen, L. et al., "High-throughout Screening an Identification of Potent Broad-spectrum Inhibitors of Coronaviruses, Journal of Virology", May 29, 2019, 93(12) pp. 1-15.
Smith, D.W. et al., "A Controlled Trial of Aerosolized Ribavinin in Infants Receiving Mechanical Ventilation for Service Respiratory Syncylial Virus Infection", The New England Journal of Medicine, 1991, vol. 325(1), pp. 24-29.
Youngnam, K. "Ribavirin efficiently suppresses porcine nidovirus replication", 2013, Virus Research, pp. 44-53.
Cho et al., "Mycophenolic mofetil, an alternative antiviral and immunomodulator for the highly pathogenic avian influenza H5N1 virus infection" Biochem Biophys Res Commun. Dec. 9, 2017;494(1-2):298-304.
International Search Report and Written Opinion for International Application No. PCT/US2024/047146 dated Nov. 27, 2024.

PREVENTION AND TREATMENT OF VIRAL INFECTIONS

This application is a Continuation of U.S. Ser. No. 17/089,020 filed Nov. 4, 2020, which is a Divisional of U.S. Ser. No. 16/793,066 filed Feb. 18, 2020, now U.S. Pat. No. 10,874,632 issued Dec. 29, 2020, which is a Continuation of U.S. Ser. No. 16/502,150 filed Jul. 3, 2019, now U.S. Pat. No. 10,603,299, issued Mar. 31, 2020, which is a Continuation-in-part of U.S. Ser. No. 16/201,205 filed Nov. 27, 2018, now U.S. Pat. No. 10,383,852 issued Aug. 20, 2019, which is a bypass continuation-in-part of PCT/US2017/035150 filed May 31, 2017, which claims benefit of U.S. Provisional Patent Application No. 62/344,591, filed Jun. 2, 2016, which are incorporated herein by reference in their entirety.

BACKGROUND

The emergence of the Zika virus represents a global health threat (Sikka, V. et al. "The emergence of Zika Virus as a Global Health Security Threat: A Review and Consensus Statement of the INDUSEM Joint Working Groups (JWG). Journal of Global Infectious Diseases. 8 (2016): 3-15). The present disclosure represents a method for prevention and treatment of the Zika virus. It provides physical, chemical, and metabolic barriers to infection by this pathogenic agent.

The Zika virus is a member of the family Flaviviridae and is an RNA containing virus. It is usually transmitted by an *Aedes* mosquito which injects it into the skin with a stinger, causing infection of three types of skin cells (epidermal keratinocytes, dermal fibroblasts, dermal macrophages)(Hamel, R., et al., "Biology of Zika Virus Infection in Human Skin Cells" J. Virol. 89 (2015):8880-8896.) and then proceeds to a viremia. It can also be transmitted sexually. It is asymptomatic in 80% of people infected, but causes mild to moderate systemic symptoms such as arthralgia, myalgia, and rash in 20% of people. Additionally it has caused catastrophic nervous system developmental impairment and microcephaly in fetuses and newborns, and Guillain-Barre paralytic syndrome in some adults. There is at this time no preventative vaccine or direct antiviral treatment. There is no way to reverse the catastrophic developmental impairment in embryos, fetuses, and newborns. For Guillain Barre Syndrome, only supportive care and immunoglobulin treatment, which is only partially effective, are available.

The inventor has found that mycophenolic acid, derivatives thereof, and combinations with other agents, such as minocycline, doxycycline, tetracycline, tetracycline derivatives, L-DOPA, and dopamine are effective in preventing and/or treating certain viruses. In addition, the inventor has found that minocycline, doxycycline, tetracycline, tetracycline derivatives, L-DOPA, dopamine, and combinations thereof are useful for preventing and/or treating a pathogenic infection in a patient, including, for example, viral infection, bacterial infection, fungal infection, parasitic infection, and combinations thereof.

The inventor has discovered that low guanosine diets can dramatically and surprisingly enhance the efficacy of oseltamivir and other neuraminidase inhibitors for treatment and prevention of viral influenza, including pandemic influenza, and other viruses.

The disclosure provides means for prevention and/or treatment of dangerous pathogenic organisms. The disclosure provides methods and pharmaceutical compositions which are active against an unusually wide range of pathogens and which have lesser toxicity compared to many currently available antimicrobial therapies.

It is shown herein that agents which reduce guanosine are effective at prevention and mitigation of viral diseases. This is demonstrated in three different viruses, using animal or in vitro models: 1. It is demonstrated that a low nucleotide diet (low guanosine diet) prevents and mitigates West Nile virus disease. including reducing mortality, in a mouse model; 2. It is demonstrated below that mycophenolic acid (which reduces guanosine levels) prevents Zika virus infection in an in vitro model; and 3. It is demonstrated below that a combination of a low nucleotide diet (low guanosine diet) and mycophenolic acid. given before infection and continued, prevents and mitigates Pandemic Influenza infection in a mouse model.

All references cited herein are incorporated herein by reference in their entireties.

BRIEF SUMMARY

The method is comprised of two parts. These two parts can be administered together or sequentially.
Part A—Methods for depletion of guanosine-containing nucleosides and nucleotides.
Part B—Methods for administering melanin and/or increasing the body content of melanin by modulation of metabolic processes.
The parts are briefly summarized below.
Part A—Method for Depletion of Guanosine-Containing Nucleosides and Nucleotides.

Guanine is a purine base which is a component of nucleosides such as guanosine and nucleotides such as guanosine monophosphate, guanosine diphosphate, and guanosine triphosphate. cyclic guanosine monophosphate, etc. Guanine is required for replication of most DNA and RNA. It is also a component of the ubiquitous G protein receptors, which are involved in innumerable signaling pathways.

Most microorganisms that cause disease do so partially by replicating themselves in high numbers. This includes viruses, bacteria, fungi, and parasites. This requires replication of DNA in bacteria, fungi, and parasites, and replication of DNA or RNA in viruses. In Zika, it is the RNA which replicates.

It has been demonstrated that restriction or complete inhibition of guanine supplies prevents replication of some viruses and other pathogenic organisms such as bacteria. This can be accomplished by several chemical agents (e.g. mycophenolic acid, tiazofurin, selenazofurin, ribavirin, 5-ethinyl-1-β-D-ribofuranosylimidazole-4-carboxamide)) (Neyts, J., and De Clercq, E. "Mycophenolate Mofetil Strongly Potentiates the Anti-herpesvirus Activity of Acyclovir." *Antiviral research* 40 (1998): 53-56.). Restriction of guanine supplies is generally not used in medical treatment of any infectious disease. It should be noted that early studies of mycophenolate showed relatively rapid emergence of bacterial resistance. and perhaps this is the reason why this strategy has not been adopted. Additionally, it is possible to significantly deplete a human's supply of guanosine by a novel selective diet restriction which is described below.

Part B—Methods for Administering Melanin and/or Increasing the Body Content of Melanin by Modulation of Metabolic Processes.

Melanin is a pigment best known for its ability in human skin to absorb ultraviolet radiation from the sun. Melanin has been clearly demonstrated to have antimicrobial properties which are active against some viruses, bacteria, fungi and parasites. Its mechanism of action seems to be unknown.

The best studied melanin in the literature is derived from cuttlefish ink. Cuttlefish is a type of cephalopod. Octopus and squid are also cephalopods and also have inks, which are used as a defense mechanism against predators. The ink contains approximately 15 to 20% melanin, about 5% protein and carbohydrates, and the rest is water.

Human beings also continuously synthesize melanin in the skin and perhaps in the nervous system. Various hormones and other agents have been demonstrated to be capable of increasing melanin synthesis in humans and other mammals. One example is Melanocyte-Stimulating Hormone (MSH).

The present disclosure represents a fundamentally novel strategy in developing therapy against Zika virus, other microbes and parasites. Historically, and increasingly so in the recent years, researchers, pharmaceutical companies, and governments devote their efforts toward targeting single agents or small groups of specific microbes. For instance, an enormous amount of resources has appropriately been devoted to fighting the HIV virus. However. as a result. most of the therapies developed are only active against that single microbe. Similarly, many of the new antibiotics developed in the last few decades are targeted to a small group of microbes. For instance the cephalosporins were developed specifically against penicillin resistant bacteria. While of course these advances are welcome, the cephalosporins are generally only active against the rather limited organisms against which they were developed.

The present disclosure represents a fundamentally different strategy from the historical strategy just described. The present disclosure targets the Zika virus and other disease-causing microbes including viruses, bacteria, fungi, and parasites. It does this using agents and methods with little toxicity compared to existing therapies.

The disclosure provides a method of preventing and/or treating a pathogenic infection in patient. the method comprising the steps of: selecting a patient in need of preventing and/or treating a pathogenic infection; administering to the patient at least one agent which depletes guanosine-containing nucleosides and nucleotides; wherein the pathogenic infection is prevented and/or treated in the patient. The disclosure provides a method wherein the pathogenic infection is selected from the group consisting of viral infection, bacterial infection, fungal infection, parasitic infection, and combinations thereof. The disclosure provides a method, wherein the pathogenic infection is a viral infection. The disclosure provides a method wherein the viral infection is selected from the group consisting of Zika virus, Norovirus, Respiratory Syncytial Virus, Influenza, Adenovirus 5, HPV 11, Lassa Fever virus, Powassan virus, Rift Valley virus, and combinations thereof. The disclosure provides a method, wherein the at least one agent which depletes guanosine-containing nucleosides and nucleotides is selected from the group consisting of mycophenolate, IMPDH enzyme inhibitors, agents which bind to guanine, or guanosine-containing nucleosides and nucleotides, and combinations thereof.

The disclosure provides a method of preventing and/or treating a pathogenic infection in patient, the method comprising the steps of: selecting a patient in need of preventing and/or treating a pathogenic infection; administering to the patient a diet which depletes guanosine-containing nucleosides and nucleotides; wherein the pathogenic infection is prevented and/or treated in the patient. The disclosure provides a method wherein the pathogenic infection is selected from the group consisting of viral infection, bacterial infection, fungal infection, parasitic infection, and combinations thereof. The disclosure provides a method wherein the pathogenic infection is a viral infection. The disclosure provides a method wherein the viral infection is selected from the group consisting of Zika virus, Norovirus, respiratory syncytial virus, Influenza, Adenovirus 5, HPV 11, Lassa Fever virus, Powassan virus, Rift Valley virus, and combinations thereof. The disclosure provides a method wherein the diet which depletes guanosine-containing nucleosides and nucleotides contains a nucleotide content which is selected from the group consisting of about 1000 mg/day, of about 750 mg/day, of about 500 mg/day, of about 250 mg/day, of about 100 mg/day, of about 75 mg/day, of about 50 mg/day. and of about 25 mg/day of nucleotide. The disclosure provides a method of administering to a patient a diet which depletes guanosine-containing nucleosides and nucleotides and an anti-viral agent. The disclosure provides a method of administering to a patient a diet which depletes guanosine-containing nucleosides and nucleotides and an anti-viral agent which is oseltamivir. The disclosure provides a method of preventing and/or treating a pathogenic infection in patient, the method comprising the steps of: selecting a patient in need of preventing and/or treating a pathogenic infection; administering to the patient at least one agent selected from the group consisting of melanin, melanin precursors, melanin derivatives, melanin analogs and related substances, and combinations thereof; wherein the pathogenic infection is prevented and/or treated in the patient. The disclosure provides a method wherein the pathogenic infection is selected from the group consisting of viral infection, bacterial infection, fungal infection, parasitic infection, and combinations thereof. The disclosure provides a method wherein the pathogenic infection is a viral infection. The disclosure provides a method wherein the viral infection is selected from the group consisting of Zika virus, Norovirus, Respiratory Syncytial Virus, Influenza, Adenovirus 5, HPV 11, Lassa Fever virus, Powassan virus, Rift Valley virus, and combinations thereof. The disclosure provides a method wherein the melanin precursor is selected from the group consisting of tyrosine, 3,4-dihydroxy phenylalanine (dopa). D-dopa, catechol, 5-hydroxyindole, tyramine, dopamine, m-aminophenol, o-aminophenol, p-aminophenol, 4-aminocatechol, 2-hydroxyl-1,4-naphthaquinone (henna), 4-methyl catechol, 3,4-dihydroxybenzylamine, 3,4-dihydroxybenzoic acid. 1,2-dihydroxynaphthalene. gallic acid, resorcinol, 2-chloroaniline, p-chloroanisole, 2-amino-p-cresol, 4,5-dihydroxynaphthalene 2,7-disulfonic acid, o-cresol, m-cresol, p-cresol, and combinations thereof. The disclosure provides a method wherein at least one agent selected from the group consisting of melanin, melanin precursors, melanin derivatives, melanin analogs and related substances. and combinations thereof is administered in topical form. The disclosure provides a method of preventing and/or treating a pathogenic infection in patient, the method comprising the steps of: selecting a patient in need of preventing and/or treating a pathogenic infection; administering to the patient at least one agent selected from the group consisting of melanin, melanin precursors, melanin derivatives, melanin analogs and related substances, and combinations thereof and an anti-viral agent. which may be oseltamivir.

The disclosure provides a pharmaceutical composition comprising at least one agent selected from the group consisting of melanin, melanin precursors, melanin derivatives, melanin analogs and related substances, and combinations thereof in a form for topical administration. The disclosure provides a pharmaceutical composition comprising at least one agent selected from the group consisting of melanin, melanin precursors, melanin derivatives, melanin analogs and related substances, and combinations thereof in a form for topical administration and an anti-viral agent which may be oseltamivir.

The disclosure provides a method of preventing and/or treating a pathogenic infection in patient, the method comprising the steps of: (i) selecting a patient in need of preventing and/or treating a pathogenic infection; (ii) administering to the patient at least one agent which depletes guanosine-containing nucleosides and nucleotides; and (iii) prior to, concurrently with, or subsequently to step (ii), administering to the patient a diet which depletes guanosine-containing nucleosides and nucleotides; wherein the pathogenic infection is prevented and/or treated in the patient. The disclosure provides a method wherein the pathogenic infection is selected from the group consisting of viral infection, bacterial infection, fungal infection, parasitic infection, and combinations thereof. The disclosure provides a method wherein the pathogenic infection is a viral infection. The disclosure provides a method wherein the viral infection is selected from the group consisting of Zika virus, Norovirus, Respiratory Syncytial Virus. Influenza, Adenovirus 5, HPV 11, Lassa Fever virus, Powassan virus, Rift Valley virus, and combinations thereof. The disclosure provides a method wherein the at least one agent which depletes guanosine-containing nucleosides and nucleotides is selected from the group consisting of mycophenolate, IMPDH enzyme inhibitors, agents which bind to guanine. or guanosine-containing nucleosides and nucleotides, and combinations thereof. The disclosure provides a method wherein the diet which depletes guanosine-containing nucleosides and nucleotides contains a nucleotide content which is selected from the group consisting of about 1000 mg/day, of about 750 mg/day, of about 500 mg/day, of about 250 mg/day, of about 100 mg/day, of about 75 mg/day, of about 50 mg/day, and of about 25 mg/day of nucleotide.

The disclosure provides a method of preventing and/or treating a pathogenic infection in a patient, the method comprising the steps of: selecting a patient in need of preventing and/or treating a pathogenic infection; administering to the patient at least one first agent which depletes guanosine-containing nucleosides and nucleotides; and administering to the patient at least one second agent selected from the group consisting of melanin, melanin precursors, melanin derivatives. melanin analogs and related substances, and combinations thereof; wherein the pathogenic infection is prevented and/or treated in the patient. The disclosure provides a method wherein the at least one first agent is administered prior to, concurrently with. or subsequently to the at least one second agent. The disclosure provides a method wherein the at least one first agent and at least one second agent are in a pharmaceutical composition. The disclosure provides a method wherein the at least one first agent and at least one second agent are in the same dosage form. The disclosure provides a method wherein the second agent is an anti-viral agent, which may be oseltamivir. The disclosure provides a method wherein the at least one first agent and at least one second agent are in separate dosage forms. The disclosure provides a method wherein the pharmaceutical composition is formulated or manufactured as a liquid, an elixir, an aerosol, a spray, a powder, a tablet, a pill, a capsule, a gel, a geltab. a nanosuspension, a nanoparticle, an extended release dosage form, or a topical formulation. The disclosure provides a method wherein the pathogenic infection is selected from the group consisting of viral infection, bacterial infection, fungal infection, parasitic infection, and combinations thereof. The disclosure provides a method wherein the pathogenic infection is a viral infection. The disclosure provides a method wherein the viral infection is selected from the group consisting of Zika virus. Norovirus, Respiratory Syncytial Virus. Influenza, Adenovirus 5, HPV 11, Lassa Fever virus. Powassan virus. Rift Valley virus, and combinations thereof. The disclosure provides a method wherein the at least one agent which depletes guanosine-containing nucleosides and nucleotides is selected from the group consisting of mycophenolate, IMPDH enzyme inhibitors, agents which bind to guanine, or guanosine-containing nucleosides and nucleotides, and combinations thereof. The disclosure provides a method wherein the melanin precursor is selected from the group consisting of tyrosine. 3,4-dihydroxy phenylalanine (dopa), D-dopa, catechol, 5-hydroxyindole, tyramine, dopamine, m-aminophenol, o-aminophenol, p-aminophenol, 4-aminocatechol, 2-hydroxyl-1,4-naphthaquinone (henna), 4-methyl catechol, 3,4-dihydroxybenzylamine, 3,4-dihydroxybenzoic acid, 1,2-dihydroxynaphthalene, gallic acid, resorcinol, 2-chloroaniline, p-chloroanisole, 2-amino-p-cresol, 4,5-dihydroxynaphthalene 2,7-disulfonic acid, o-cresol, m-cresol. p-cresol, and combinations thereof.

The disclosure provides a pharmaceutical composition comprising: (i) at least one first agent which depletes guanosine-containing nucleosides and nucleotides; and (ii) at least one second agent selected from the group consisting of melanin, melanin precursors, melanin derivatives, melanin analogs and related substances, and combinations thereof; wherein the pharmaceutical composition further comprises at least one pharmaceutically acceptable excipient. The disclosure provides a pharmaceutical composition wherein the at least one agent which depletes guanosine-containing nucleosides and nucleotides is selected from the group consisting of mycophenolate. IMPDH enzyme inhibitors, agents which bind to guanine, or guanosine-containing nucleosides and nucleotides, and combinations thereof. The disclosure provides a pharmaceutical composition wherein the pharmaceutical composition is formulated or manufactured as a liquid, an elixir, an aerosol, a spray, a powder, a tablet, a pill, a capsule, a gel, a geltab, a nanosuspension, a nanoparticle, an extended release dosage form, or a topical formulation. The disclosure provides a pharmaceutical composition wherein the at least one first agent and at least one second agent are in the same dosage form. The disclosure provides a pharmaceutical composition wherein the at least one first agent and at least one second agent are in separate dosage forms. The disclosure provides a pharmaceutical composition wherein the pharmaceutical composition is formulated or manufactured as a liquid, an elixir, an aerosol, a spray, a powder, a tablet, a pill, a capsule, a gel, a geltab, a nanosuspension, a nanoparticle, an extended release dosage form. or a topical formulation. The disclosure provides a pharmaceutical composition wherein the pharmaceutical composition is in a form for topical administration. The disclosure provides a pharmaceutical composition comprising: (i) at least one first agent which depletes guanosine-containing nucleosides and nucleotides; and (ii) at least one second agent selected from the group consisting of melanin, melanin precursors, melanin derivatives, melanin analogs and related substances. and combinations thereof and an anti-viral agent, which may be oseltamivir.

The disclosure provides a pharmaceutical composition comprising: (i) at least one first agent which depletes guanosine-containing nucleosides and nucleotides; and (ii) at least one second agent which is an anti-viral agent, which may be oseltamivir.

The disclosure provides a method of preventing and/or treating a pathogenic infection in a patient, the method comprising the steps of: selecting a patient in need of preventing and/or treating a pathogenic infection; administering to the patient at least one first agent which depletes guanosine-containing nucleosides and nucleotides; and administering to the patient at least one second agent selected from the group consisting of minocycline, doxycycline, tetracycline. tetracycline derivatives, L-DOPA, dopamine, and combinations thereof; wherein the pathogenic infection is prevented and/or treated in the patient. The disclosure provides a method wherein the at least one agent which depletes guanosine-containing nucleosides and nucleotides is selected from the group consisting of mycophenolate. IMPDH enzyme inhibitors, agents which bind to guanine. or guanosine-containing nucleosides and nucleotides, and combinations thereof. The disclosure provides a method wherein the at least one first agent is administered prior to, concurrently with, or subsequently to the at least one second agent. The disclosure provides a method wherein the at least one first agent and at least one second agent are in a pharmaceutical composition. The disclosure provides a method wherein the at least one first agent and at least one second agent are in the same dosage form. The disclosure provides a method wherein the at least one first agent and at least one second agent are in separate dosage forms. The disclosure provides a method wherein the pharmaceutical composition is formulated or manufactured as a liquid, an elixir, an aerosol, a spray. a powder, a tablet, a pill, a capsule, a gel, a geltab, a nanosuspension, a nanoparticle, an extended release dosage form, or a topical formulation. The disclosure provides a method wherein the pathogenic infection is selected from the group consisting of viral infection, bacterial infection, fungal infection, parasitic infection, and combinations thereof. The disclosure provides a method wherein the pathogenic infection is a viral infection. The disclosure provides a method wherein the viral infection is selected from the group consisting of Zika virus. Norovirus, Respiratory Syncytial Virus, Influenza. Adenovirus 5, HPV 11, Lassa Fever virus, Powassan virus, Rift Valley virus, and combinations thereof. The disclosure provides a method wherein the at least one agent which depletes guanosine-containing nucleosides and nucleotides is selected from the group consisting of mycophenolate. IMPDH enzyme inhibitors, agents which bind to guanine, or guanosine-containing nucleosides and nucleotides. and combinations thereof. The disclosure provides a method wherein the melanin precursor is selected from the group consisting of tyrosine, 3,4-dihydroxy phenylalanine (dopa), D-dopa, catechol, 5-hydroxyindole, tyramine, dopamine, m-aminophenol, o-aminophenol, p-aminophenol, 4-aminocatechol, 2-hydroxyl-1, 4-naphthaquinone (henna), 4-methyl catechol, 3,4-dihydroxybenzylamine, 3,4-dihydroxybenzoic acid, 1,2-dihydroxynaphthalene, gallic acid, resorcinol. 2-chloroaniline, p-chloroanisole, 2-amino-p-cresol, 4,5-dihydroxynaphthalene 2,7-disulfonic acid, o-cresol, m-cresol, p-cresol, and combinations thereof. The disclosure provides a method of preventing and/or treating a pathogenic infection in a patient. the method comprising the steps of: selecting a patient in need of preventing and/or treating a pathogenic infection; administering to the patient at least one first agent which depletes guanosine-containing nucleosides and nucleotides; and administering to the patient at least one second agent selected from the group consisting of minocycline, doxycycline, tetracycline, tetracycline derivatives, L-DOPA, dopamine, and combinations thereof, and an anti-viral agent which may be osctamivir.

The disclosure provides a pharmaceutical composition comprising: (i) at least one first agent which depletes guanosine-containing nucleosides and nucleotides; and (ii) at least one second agent selected from the group consisting of minocycline, doxycycline, tetracycline, tetracycline derivatives. L-DOPA, dopamine, and combinations thereof; wherein the pharmaceutical composition further comprises at least one pharmaceutically acceptable excipient. The disclosure provides a pharmaceutical composition wherein the at least one agent which depletes guanosine-containing nucleosides and nucleotides is selected from the group consisting of mycophenolate, IMPDH enzyme inhibitors, agents which bind to guanine, or guanosine-containing nucleosides and nucleotides, and combinations thereof. The disclosure provides a pharmaceutical composition wherein the pharmaceutical composition is formulated or manufactured as a liquid, an elixir, an aerosol, a spray. a powder, a tablet, a pill, a capsule. a gel, a geltab, a nanosuspension, a nanoparticle, an extended release dosage form, or a topical formulation. The disclosure provides a pharmaceutical composition wherein the at least one first agent and at least one second agent are in the same dosage form. The disclosure provides a pharmaceutical composition wherein the at least one first agent and at least one second agent are in separate dosage forms. The disclosure provides a pharmaceutical composition wherein the pharmaceutical composition is formulated or manufactured as a liquid, an elixir, an aerosol, a spray, a powder, a tablet, a pill, a capsule, a gel, a geltab, a nanosuspension, a nanoparticle, an extended release dosage form, or a topical formulation. The disclosure provides a pharmaceutical composition wherein the pharmaceutical composition is in a form for topical administration. The disclosure provides a pharmaceutical composition comprising: (i) at least one first agent which depletes guanosine-containing nucleosides and nucleotides; and (ii) at least one second agent which is an antiviral agent, which may be oseltamivir.

The disclosure provides a method of preventing and/or treating postviral neurological syndromes in a patient, the method comprising the steps of: selecting a patient in need of preventing and/or treating postviral neurological syndrome; administering to the patient at least one agent selected from the group consisting of melanin, melanin precursors, melanin derivatives, melanin analogs, minocycline, doxycycline, tetracycline, tetracycline derivatives. L-DOPA, dopamine, and combinations thereof; wherein the postviral neurological syndromes is prevented and/or treated in the patient. The disclosure provides a method wherein the postviral neurological syndromes are as a result of infection by a virus selected from the group consisting of Zika virus, Norovirus, Respiratory Syncytial Virus, Influenza, Adenovirus 5, HPV 11, Lassa Fever virus, Powassan virus, Rift Valley virus, and combinations thereof. The disclosure provides a method wherein at least one agent is administered in topical form. The disclosure provides a method of preventing and/or treating postviral neurological syndromes in a patient. the method comprising the steps of: selecting a patient in need of preventing and/or treating postviral neurological syndrome; administering to the patient at least one agent selected from the group consisting of melanin, melanin precursors, melanin derivatives, melanin analogs, minocycline, doxycycline, tetracycline, tetracycline derivatives, L-DOPA, dopamine, and combinations thereof, and an antiviral agent which may be oseltamivir.

The disclosure provides a method of preventing and/or treating a pathogenic infection in a patient, the method comprising the steps of: selecting a patient in need of preventing and/or treating a pathogenic infection; administering to the patient at least one agent selected from the group consisting of minocycline, doxycycline. tetracycline, tetracycline derivatives, L-DOPA, dopamine, and combinations thereof; wherein the pathogenic infection is prevented and/or treated in the patient. The disclosure provides a method wherein the at least one agent is administered prior to, concurrently with, or subsequently to the at least one second agent. The disclosure provides a method wherein the at least one agent is in a pharmaceutical composition. The disclosure provides a method wherein the pharmaceutical composition is formulated or manufactured as a liquid, an elixir, an aerosol, a spray, a powder, a tablet, a pill, a capsule, a gel, a geltab, a nanosuspension, a nanoparticle, an extended release dosage form, or a topical formulation. The disclosure provides a method wherein the pathogenic infection is selected from the group consisting of viral infection, bacterial infection, fungal infection, parasitic infection, and combinations thereof. The disclosure provides a method wherein the pathogenic infection is a viral infection. The disclosure provides a method wherein the viral infection is selected from the group consisting of Zika virus, Norovirus, Respiratory Syncytial Virus. Influenza, Adenovirus 5. HPV 11, Lassa Fever virus, Powassan virus, Rift Valley virus, and combinations thereof. The disclosure provides a method of preventing and/or treating a pathogenic infection in a patient, the method comprising the steps of: selecting a patient in need of preventing and/or treating a pathogenic infection; administering to the patient at least one agent selected from the group consisting of minocycline, doxycycline, tetracycline, tetracycline derivatives. L-DOPA, dopamine, and combinations thereof, and an anti-viral agent which may be oseltamivir.

The disclosure provides a pharmaceutical composition comprising: at least one agent selected from the group consisting of minocycline, doxycycline, tetracycline, tetracycline derivatives, L-DOPA, dopamine, and combinations thereof; wherein the pharmaceutical composition further comprises at least one pharmaceutically acceptable excipient. The disclosure provides a pharmaceutical composition wherein the pharmaceutical composition is formulated or manufactured as a liquid, an elixir, an aerosol, a spray, a powder, a tablet, a pill, a capsule, a gel, a geltab, a nanosuspension, a nanoparticle, an extended release dosage form, or a topical formulation. The disclosure provides a pharmaceutical composition wherein the pharmaceutical composition is formulated or manufactured as a liquid, an elixir, an aerosol, a spray, a powder, a tablet, a pill, a capsule, a gel, a geltab, a nanosuspension. a nanoparticle, an extended release dosage form, or a topical formulation. The disclosure provides a pharmaceutical composition wherein the pharmaceutical composition is in a form for topical administration. The disclosure provides a pharmaceutical composition comprising: at least one agent selected from the group consisting of minocycline, doxycycline, tetracycline, tetracycline derivatives, L-DOPA, dopamine, and combinations thereof, and an anti-viral agent which may be oseltamivir.

The disclosure provides a pharmaceutical composition comprising: at least one agent selected from the group consisting of minocycline, doxycycline, tetracycline, tetracycline derivatives, L-DOPA, dopamine, and combinations thereof; wherein the pharmaceutical composition further comprises at least one second agent which is an anti-viral agent, which may be oseltamivir.

The disclosure provides a method of preventing and/or treating postviral neurological syndromes in a patient, the method comprising the steps of: selecting a patient in need of preventing and/or treating postviral neurological syndrome; administering to the patient at least one agent selected from the group consisting of minocycline. doxycycline. tetracycline, tetracycline derivatives, L-DOPA, dopamine, and combinations thereof; wherein the postviral neurological syndrome is prevented and/or treated in the patient. The disclosure provides a method wherein the postviral neurological syndromes are as a result of infection by a virus selected from the group consisting of Zika virus. Norovirus. Respiratory Syncytial Virus. Influenza, Adenovirus 5, HPV 11. Lassa Fever virus. Powassan virus, Rift Valley virus, and combinations thereof. The disclosure provides a method wherein at least one agent is administered in topical form. The disclosure provides a method of preventing and/or treating postviral neurological syndromes in a patient, the method comprising the steps of: selecting a patient in need of preventing and/or treating postviral neurological syndrome; administering to the patient at least one agent selected from the group consisting of minocycline, doxycycline, tetracycline, tetracycline derivatives, L-DOPA, dopamine, and combinations thereof, and an anti-viral agent which may be oseltamivir.

The disclosure provides a method of preventing a viral infection in a patient, the method comprising the steps of: selecting a patient in need of preventing a viral infection; administering to the patient at least one agent which depletes guanosine-containing nucleosides and nucleotides; wherein the viral infection is a flaviviridae virus, and further wherein the viral infection is prevented in the patient. The disclosure provides a method wherein the flaviviridae virus is selected from the group consisting of Absettarov virus, Alfuy virus Apoi virus Aroa virus, Bagaza virus Border disease virus Bouboui virus Bovine diarrhea virus Bussuquara virus Bukalasa bat virus, Dengue virus group, Hog cholera virus, Zika virus. Yellow fever virus; Dengue virus; St. Louis encephalitis virus; Japanese encephalitis virus; Tick-borne encephalitis virus; Omsk hemorrhagic fever virus; Al Khumra virus; Kyasanur Forest disease virus; Louping ill virus; West Nile virus; Kunjin virus; Murray Valley fever virus; Powassan virus; Hepatitis C virus; Hepatitis G virus, and combinations thereof. The disclosure provides a method wherein the at least one agent which depletes guanosine-containing nucleosides and nucleotides is selected from the group consisting of mycophenolate, IMPDH enzyme inhibitors, agents which bind to guanine. or guanosine-containing nucleosides and nucleotides, and combinations thereof.

The disclosure provides a method of preventing a viral infection in a patient, the method comprising the steps of: selecting a patient in need of preventing a viral infection; administering to the patient a diet which depletes guanosine-containing nucleosides and nucleotides; wherein the viral infection is a flaviviridae virus, and further wherein the viral infection is prevented in the patient. The disclosure provides a method wherein the flaviviridae virus is selected from the group consisting of Absettarov virus, Alfuy virus Apoi virus Aroa virus. Bagaza virus Border disease virus Bouboui virus Bovine diarrhea virus Bussuquara virus Bukalasa bat virus, Dengue virus group, Hog cholera virus. Zika virus. Yellow fever virus; Dengue virus; St. Louis encephalitis virus; Japanese encephalitis virus; Tick-borne encephalitis virus; Omsk hemorrhagic fever virus; Al Khumra virus; Kyasanur Forest disease virus; Louping ill virus; West Nile virus; Kunjin virus; Murray Valley fever virus; Powassan virus; Hepatitis C virus; Hepatitis G virus. and combinations thereof. The disclosure provides a method wherein the diet which depletes guanosine-containing nucleosides and nucleotides contains a nucleotide content which is selected from the group consisting of about 1000 mg/day, of about 750 mg/day, of about 500 mg/day, of about 250 mg/day, of about 100 mg/day, of about 75 mg/day, of about 50 mg/day, and of about 25 mg/day of nucleotide.

The disclosure provides a method of preventing a viral infection in a patient, the method comprising the steps of: (i) selecting a patient in need of preventing a viral infection; (ii) administering to the patient at least one agent which depletes guanosine-containing nucleosides and nucleotides; and (iii) prior to, concurrently with, or subsequently to step (ii), administering to the patient a diet which depletes guanosine-containing nucleosides and nucleotides; wherein the virus is a flaviviridae virus, and further wherein the viral infection is prevented in the patient. The disclosure provides a method wherein the flaviviridae virus is selected from the group consisting of Absettarov virus, Alfuy virus Apoi virus Aroa virus, Bagaza virus Border disease virus Bouboui virus Bovine diarrhea virus Bussuquara virus Bukalasa bat virus, Dengue virus group, Hog cholera virus, Zika virus, Yellow fever virus; Dengue virus; St. Louis encephalitis virus; Japanese encephalitis virus; Tick-borne encephalitis virus; Omsk hemorrhagic fever virus; Al Khumra virus; Kyasanur Forest disease virus; Louping ill virus; West Nile virus; Kunjin virus; Murray Valley fever virus; Powassan virus; Hepatitis C virus; Hepatitis G virus, and combinations thereof. The disclosure provides a method wherein the at least one agent which depletes guanosine-containing nucleosides and nucleotides is selected from the group consisting of mycophenolate, IMPDH enzyme inhibitors, agents which bind to guanine, or guanosine-containing nucleosides and nucleotides, and combinations thereof. The disclosure provides a method wherein the diet which depletes guanosine-containing nucleosides and nucleotides contains a nucleotide content which is selected from the group consisting of about 1000 mg/day, of about 750 mg/day, of about 500 mg/day, of about 250 mg/day, of about 100 mg/day, of about 75 mg/day, of about 50 mg/day, and of about 25 mg/day of nucleotide.

The disclosure provides a method of preventing a viral infection in a patient, the method comprising the steps of: selecting a patient in need of preventing a viral infection; administering to the patient at least one agent which depletes guanosine-containing nucleosides and nucleotides; wherein the viral infection is a respiratory virus, and further wherein the viral infection is prevented in the patient. The disclosure provides a method wherein the respiratory virus is selected from the group consisting of Influenza virus type A. Influenza A H3N2; Influenza A H5N1 (low path); Influenza B (Victoria); Influenza B (Yamagata); Parainfluenza virus-3; Rhinovirus-14; Influenza A H7N9 virus; Influenza A H5N1 (high path), Adenoviruses, Avian influenza, Measles, Parainfluenza virus, Respiratory syncytial virus (RSV), Rhinoviruses, SARS coronavirus, and combinations thereof. The disclosure provides a method wherein the at least one agent which depletes guanosine-containing nucleosides and nucleotides is selected from the group consisting of mycophenolate, IMPDH enzyme inhibitors, agents which bind to guanine. or guanosine-containing nucleosides and nucleotides, and combinations thereof.

The disclosure provides a method of preventing a viral infection in a patient, the method comprising the steps of: selecting a patient in need of preventing a viral infection; administering to the patient a diet which depletes guanosine-containing nucleosides and nucleotides; wherein the viral infection is a respiratory virus, and further wherein the viral infection is prevented in the patient. The disclosure provides a method wherein the respiratory virus is selected from the group consisting of Influenza virus type A, Influenza A H3N2; Influenza A H5N1 (low path); Influenza B (Victoria); Influenza B (Yamagata); Parainfluenza virus-3; Rhinovirus-14; Influenza A H7N9 virus; Influenza A H5N1 (high path), Adenoviruses, Avian influenza, Measles, Parainfluenza virus, Respiratory syncytial virus (RSV), Rhinoviruses, SARS coronavirus, and combinations thereof. The disclosure provides a method wherein the diet which depletes guanosine-containing nucleosides and nucleotides contains a nucleotide content which is selected from the group consisting of about 1000 mg/day, of about 750 mg/day, of about 500 mg/day, of about 250 mg/day, of about 100 mg/day, of about 75 mg/day, of about 50 mg/day, and of about 25 mg/day of nucleotide.

The disclosure provides a method of preventing a viral infection in a patient, the method comprising the steps of: (i) selecting a patient in need of preventing a viral infection; (ii) administering to the patient at least one agent which depletes guanosine-containing nucleosides and nucleotides; and (iii) prior to, concurrently with, or subsequently to step (ii), administering to the patient a diet which depletes guanosine-containing nucleosides and nucleotides; wherein the viral infection is a respiratory virus, and further wherein the viral infection is prevented in the patient. The disclosure provides a method wherein the respiratory virus is selected from the group consisting of Influenza virus type A, Influenza A H3N2; Influenza A H5N1 (low path); Influenza B (Victoria); Influenza B (Yamagata); Parainfluenza virus-3; Rhinovirus-14; Influenza A H7N9 virus; Influenza A H5N1 (high path). Adenoviruses. Avian influenza, Measles. Parainfluenza virus, Respiratory syncytial virus (RSV), Rhinoviruses, SARS coronavirus, and combinations thereof. The disclosure provides a method wherein the at least one agent which depletes guanosine-containing nucleosides and nucleotides is selected from the group consisting of mycophenolate, IMPDH enzyme inhibitors. agents which bind to guanine, or guanosine-containing nucleosides and nucleotides, and combinations thereof. The disclosure provides a method wherein the diet which depletes guanosine-containing nucleosides and nucleotides contains a nucleotide content which is selected from the group consisting of about 1000 mg/day, of about 750 mg/day. of about 500 mg/day, of about 250 mg/day, of about 100 mg/day, of about 75 mg/day, of about 50 mg/day, and of about 25 mg/day of nucleotide.

The disclosure provides a method of preventing a viral infection in a patient, the method comprising the steps of: selecting a patient in need of preventing a viral infection; administering to the patient at least one agent which depletes guanosine-containing nucleosides and nucleotides; further wherein the viral infection is prevented in the patient. The disclosure provides a method wherein the virus which causes the viral infection is selected from the group consisting of Parvoviridae; Papovaviridae, Human papilloma virus (HPV); BK polyomavirus; JC polyomavirus); Adenoviridae (Adenovirus, types 40 and 41); Herpesviridae (simplex virus type 1 (HHV-1); Herpes simplex virus type 2 (HHV-2); Macacine herpesvirus 1; Varicella-zoster virus; Epstein-Barr virus; Cytomegalovirus); Human Herpesvirus 6; HHV-7; Kaposi's sarcoma-associated herpesvirus; Hepadnaviridae, Hepatitis B virus; Poxviridae (Smallpox (Variola major); Alastrim (Variola minor); Vaccinia; Cowpox; Monkeypox; Goat pox, pseudocowpox virus, bovine papular stomatitis virus, tanapox, volepox and related pox viruses such as avipox, buffalopox, racoonpox, squirrelpox, etc.); Molluscum contagiosum; Picornaviridae (Polio virus; Coxsackie A virus; Coxsackie B; virus; Foot and mouth disease; ECHO virus; Hepatitis A virus; Rhinovirus); Astroviridae; Caliciviridae (Norwalk virus; Norovirus; Sapoviruses; Hepatitis E virus); Reoviridae (Rotavirus); Togaviridae (Alpha viruses; Western equine encephalitis (WEE) virus; Eastern equine encephalitis (EEE) virus; Venezuelan equine encephalitis (VEE) virus; Chikungunya virus; Rubivirus (rubella)); Flaviviridae (Yellow fever virus; Dengue virus; St. Louis encephalitis virus; Japanese encephalitis virus; Tick-borne encephalitis virus; Omsk hemorrhagic fever virus; Al Khumra virus; Kyasanur Forest disease virus; Louping ill virus; West Nile virus; Kunjin virus; Murray Valley fever virus; Powassan virus; Hepatitis C virus; Hepatitis G virus); Coronaviridae (Respiratory illness (cold); Severe Acute Respiratory Syndrome)-corona virus (SARS-CoV)); Bunyaviridae (California encephalitis virus; La Crosse virus; Rift Valley fever virus; Phleboviruses; Sandfly fever virus; Nairovirus; Hantavirus); Orthomyxoviridae (Influenza virus (types A. B & C); Paramyxoviridae (Parainfluenza virus; Respiratory syncytial virus (RSV); Hendra virus disease (formerly equine morbillivirus); Nipah virus encephalitis; Mumps Measles; Newcastle disease virus); Rhabdoviridae (Rabies virus); Filoviridae (Marburg virus (acute hemorrhagic fever); Ebola virus (acute hemorrhagic fever)); Arenaviridae (Lymphocytic choriomeningitis virus; Lassa fever virus; Lujo virus; Chapare virus; Junin virus; Machupo virus; Guanarito virus; Sabia virus); Retroviridae (Human Immunodeficiency virus (HIV) types I and II; Human T-cell leukemia virus (HLTV) type I; Human T-cell leukemia virus (HLTV) type II; Spumaviruses; Xenotropic murine leukemia virus-related (XMRV), and combinations thereof. The disclosure provides a method wherein the at least one agent which depletes guanosine-containing nucleosides and nucleotides is selected from the group consisting of mycophenolate, IMPDH enzyme inhibitors, agents which bind to guanine. or guanosine-containing nucleosides and nucleotides, and combinations thereof.

The disclosure provides a method of preventing a viral infection in a patient, the method comprising the steps of: selecting a patient in need of preventing a viral infection; administering to the patient a diet which depletes guanosine-containing nucleosides and nucleotides; further wherein the viral infection is prevented in the patient. The disclosure provides a method wherein the virus which causes the viral infection is selected from the group consisting of Parvoviridae; Papovaviridae, Human papilloma virus (HPV); BK polyomavirus; JC polyomavirus); Adenoviridae (Adenovirus, types 40 and 41); Herpesviridae (simplex virus type 1 (HHV-1); Herpes simplex virus type 2 (HHV-2); Macacine herpesvirus 1; Varicella-zoster virus; Epstein-Barr virus; Cytomegalovirus); Human Herpesvirus 6; HHV-7; Kaposi's sarcoma-associated herpesvirus; Hepadnaviridae, Hepatitis B virus; Poxviridae (Smallpox (Variola major); Alastrim (Variola minor); Vaccinia; Cowpox; Monkeypox; Goat pox, pseudocowpox virus, bovine papular stomatitis virus, tanapox, volepox and related pox viruses such as avipox, buffalopox, racoonpox, squirrelpox, etc.); Molluscum contagiosum; Picornaviridae (Polio virus; Coxsackie A virus; Coxsackie B; virus; Foot and mouth disease; ECHO virus; Hepatitis A virus; Rhinovirus); Astroviridae; Caliciviridae (Norwalk virus; Norovirus; Sapoviruses; Hepatitis E virus); Reoviridae (Rotavirus); Togaviridae (Alpha viruses; Western equine encephalitis (WEE) virus; Eastern equine encephalitis (EEE) virus; Venezuelan equine encephalitis (VEE) virus; Chikungunya virus; Rubivirus (rubella)); Flaviviridae (Yellow fever virus; Dengue virus; St. Louis encephalitis virus; Japanese encephalitis virus; Tick-borne encephalitis virus; Omsk hemorrhagic fever virus; Al Khumra virus; Kyasanur Forest disease virus; Louping ill virus; West Nile virus; Kunjin virus; Murray Valley fever virus; Powassan virus; Hepatitis C virus; Hepatitis G virus); Coronaviridae (Respiratory illness (cold); Severe Acute Respiratory Syndrome)-corona virus (SARS-CoV)); Bunyaviridae (California encephalitis virus; La Crosse virus; Rift Valley fever virus; Phleboviruses; Sandfly fever virus; Nairovirus; Hantavirus); Orthomyxoviridae (Influenza virus (types A. B & C); Paramyxoviridae (Parainfluenza virus; Respiratory syncytial virus (RSV); Hendra virus disease (formerly equine morbillivirus); Nipah virus encephalitis; Mumps Measles; Newcastle disease virus); Rhabdoviridae (Rabies virus); Filoviridae (Marburg virus (acute hemorrhagic fever); Ebola virus (acute hemorrhagic fever)); Arenaviridae (Lymphocytic choriomeningitis virus; Lassa fever virus; Lujo virus; Chapare virus; Junin virus; Machupo virus; Guanarito virus; Sabia virus); Retroviridae (Human Immunodeficiency virus (HIV) types I and II; Human T-cell leukemia virus (HLTV) type I; Human T-cell leukemia virus (HLTV) type II; Spumaviruses; Xenotropic murine leukemia virus-related (XMRV), and combinations thereof. The disclosure provides a method wherein the diet which depletes guanosine-containing nucleosides and nucleotides contains a nucleotide content which is selected from the group consisting of about 1000 mg/day, of about 750 mg/day, of about 500 mg/day, of about 250 mg/day, of about 100 mg/day. of about 75 mg/day, of about 50 mg/day, and of about 25 mg/day of nucleotide.

The disclosure provides a method of preventing a viral infection in a patient, the method comprising the steps of: (i) selecting a patient in need of preventing a viral infection; (ii) administering to the patient at least one agent which depletes guanosine-containing nucleosides and nucleotides; and (iii) prior to, concurrently with, or subsequently to step (ii), administering to the patient a diet which depletes guanosine-containing nucleosides and nucleotides; wherein the viral infection is prevented in the patient. The disclosure provides a method wherein the virus which causes the viral infection is selected from the group consisting of Parvoviridae; Papovaviridae, Human papilloma virus (HPV); BK polyomavirus; JC polyomavirus); Adenoviridae (Adenovirus, types 40 and 41); Herpesviridae (simplex virus type 1 (HHV-1); Herpes simplex virus type 2 (HHV-2); Macacine herpesvirus 1; Varicella-zoster virus; Epstein-Barr virus; Cytomegalovirus); Human Herpesvirus 6; HHV-7; Kaposi's sarcoma-associated herpesvirus; Hepadnaviridae, Hepatitis B virus; Poxviridae (Smallpox (Variola major); Alastrim (Variola minor); Vaccinia; Cowpox; Monkeypox; Goat pox, pseudocowpox virus, bovine papular stomatitis virus, tanapox, volepox and related pox viruses such as avipox, buffalopox, racoonpox, squirrelpox, etc.); Molluscum contagiosum; Picornaviridae (Polio virus; Coxsackie A virus; Coxsackie B; virus; Foot and mouth disease; ECHO virus; Hepatitis A virus; Rhinovirus); Astroviridae; Caliciviridae (Norwalk virus; Norovirus; Sapoviruses; Hepatitis E virus); Reoviridae (Rotavirus); Togaviridae (Alpha viruses; Western equine encephalitis (WEE) virus; Eastern equine encephalitis (EEE) virus; Venezuelan equine encephalitis (VEE) virus; Chikungunya virus; Rubivirus (rubella)); Flaviviridae (Yellow fever virus; Dengue virus; St. Louis encephalitis virus; Japanese encephalitis virus; Tick-borne encephalitis virus; Omsk hemorrhagic fever virus; Al Khumra virus; Kyasanur Forest disease virus; Louping ill virus; West Nile virus; Kunjin virus; Murray Valley fever virus; Powassan virus; Hepatitis C virus; Hepatitis G virus); Coronaviridae (Respiratory illness (cold); Severe Acute Respiratory Syndrome)-corona virus (SARS-CoV)); Bunyaviridae (California encephalitis virus; La Crosse virus; Rift Valley fever virus; Phleboviruses; Sandfly fever virus; Nairovirus; Hantavirus); Orthomyxoviridae (Influenza virus (types A, B & C); Paramyxoviridae (Parainfluenza virus; Respiratory syncytial virus (RSV); Hendra virus disease (formerly equine morbillivirus); Nipah virus encephalitis; Mumps Measles; Newcastle disease virus); Rhabdoviridae (Rabies virus); Filoviridae (Marburg virus (acute hemorrhagic fever); Ebola virus (acute hemorrhagic fever)); Arenaviridae (Lymphocytic choriomeningitis virus; Lassa fever virus; Lujo virus; Chapare virus; Junin virus; Machupo virus; Guanarito virus; Sabia virus); Retroviridae (Human Immunodeficiency virus (HIV) types I and II; Human T-cell leukemia virus (HLTV) type I; Human T-cell leukemia virus (HLTV) type II; Spumaviruses; Xenotropic murine leukemia virus-related (XMRV), and combinations thereof. The disclosure provides a method wherein the at least one agent which depletes guanosine-containing nucleosides and nucleotides is selected from the group consisting of mycophenolate. IMPDH enzyme inhibitors, agents which bind to guanine. or guanosine-containing nucleosides and nucleotides, and combinations thereof. The disclosure provides a method wherein the diet which depletes guanosine-containing nucleosides and nucleotides contains a nucleotide content which is selected from the group consisting of about 1000 mg/day, of about 750 mg/day, of about 500 mg/day, of about 250 mg/day, of about 100 mg/day, of about 75 mg/day. of about 50 mg/day, and of about 25 mg/day of nucleotide.

The disclosure provides for the use of the compositions of the disclosure for the production of a medicament for preventing and/or treating the indications as set forth herein.

In accordance with a further embodiment, the present disclosure provides a use of the pharmaceutical compositions described above, in an amount effective for use in a medicament, and most preferably for use as a medicament for treating a disease or disorder, for example, as set forth in herein, in a subject.

In accordance with yet another embodiment, the present disclosure provides a use of the pharmaceutical compositions described above, and at least one additional therapeutic agent, in an amount effective for use in a medicament, and most preferably for use as a medicament for treating a disease or disorder associated with disease, for example, as set forth herein, in a subject.

The disclosure provides a method for treating and/or preventing a disease or condition as set forth herein in a patient, wherein said method comprises: selecting a patient in need of treating and/or preventing said disease or condition as set forth herein; administering to the patient a composition of the disclosure in a therapeutically effective amount, thereby treating and/or preventing said disease in said patient.

DETAILED DESCRIPTION OF THE INVENTION

In order to provide a clear and consistent understanding of the specification and claims, including the scope given to such terms, the following definitions are provided:

To the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

TAMIFLU® as available on the market comprises oseltamivir phosphate, which is a pro-drug of the active metabolite oseltamivir carboxylate, and is specifically adapted for oral administration. Where intranasal administration is intended according to the present disclosure the active form oseltamivir carboxylate may be used instead of the phosphate pro-drug form.

Thus, the term "oseltamivir" as used herein refers to either oseltamivir carboxylate or oseltamivir phosphate, unless explicitly stated otherwise or unless a different meaning is derivable from the disclosure. The antiviral agent may be selected from but is not limited to the group consisting of zanamivir, oseltamivir, peramivir and laninamivir. Antiviral agents may also include, but are not limited to, the following: acemannan; alovudine; alvircept sudotox; aranotin; arildone; atevirdine mesylate; avridine, carbovir, cipamfylline; clevadine, crixivan, cytarabine; desciclovir; dideoxyinosine, dideoxycytidine, disoxaril, edoxudine; enfuvirtide, entecavir, enviradene; enviroxime; famciclovir; famotine; fiacitabine; fialuridine; floxuridine, fosarilate; fosfonet, gancyclovir, kethoxal; levovirin, lobucavir; lopinovir, memotine, methisazone; moroxydine, oseltamivir, pirodavir, pleconaril, podophyllotoxin, rimantadine, sequanavir, somantadine, sorivudine, stallimycine, statolon; tilorone; tromantadine, valacyclovir, viramidine, viroxime. xenazoic acid, zalcitabine; zerit, zinviroxime, pyridine, α-methyl-1-adamantanemethylamine, hydroxy-ethoxymethylguanine, adamantanamine, 5-iodo-2'-deoxyuridine, trifluorothymidine, adenine arabinoside, 2',3'-dideoxynucleosides such as 2',3'-didoxycytidine, 2',3'-didcoxyadenosine, 2',3'-didoxyinosine, 2',3'-didehydrothymidine, co-trimoxazole, 9-[2-(R)-[[bis[Risopropoxy-carbonyl)oxy]-methoxy]phosphinoyl]methoxy]propyl]adenine, (R)-9-[2-(phosphonomethoxy)-propyl]adenine, tenofivir disoproxil, TAT inhibitors such as 7-chloro-5-(2-pyrryl)-3H-1,4-benzodiazepin-2(H)-one. Suitable dosage of the antiviral agent for administration may range from about 0.1 μg/day to about 2 g/day, from about 1 μg/day to about 1 g/day, from about 5 μg/day to about 500 mg/day, from about 10 μg/day to about 300 mg/day, or from about 1 mg/day to about 200 mg/day.

Administration: The application or delivery of a drug to a mammal in need of the drug. This term is intended to include any means of administration which accomplishes the application or delivery of the drug (i. e., topical, oral, aerosol, suppository, parenteral, e. g., intravenous. intramuscular, subcutaneous injection, e. g., into the tissue, intraperitoneally and the like). The term is also intended to include any means necessary to accomplish such administration. The term is further intended to include the in vivo production of a drug or aggregation of a drug moderated by another substance such as an enzyme (tyrosinase) or enzyme gene (tyrosinase gene) to moderate production of a drug (melanin) or its precursors, or a concentrating hormone (MCH) subcutaneously to moderate drug (melanin) concentration.

Treatment: Treatment is defined as administration to a mammal suffering from infections or burns or administration to a mammal at risk for such infections.

Melanin: Melanins are polymers produced by polymerization of reactive intermediates. The polymerization mechanisms include but are not limited to autoxidation, enzyme catalyzed polymerization and free radical initiated polymerization. The reactive intermediates are produced chemically or enzymatically from precursors. Suitable enzymes include, but are not limited to peroxidases and catalases, polyphenol oxidases, tyrosinases, tyrosine hydroxylases or lactases. The precursors which are connected to the reactive intermediates are hydroxylated aromatic compounds. Suitable hydroxylated aromatic compounds include, but are not limited to 1) phenols, polyphenols, aminophenols and thiophenols of aromatic or polycyclicaromatic hydrocarbons, including but not limited to phenol. tyrosine, pyrogallol, 3-aminotyrosine, thiophenol and. alpha.-naphthol; 2) phenols, polyphenols, aminophenols, and thiophenols of aromatic heterocyclic or heteropolycyclic hydrocarbons such as but not limited to 2-hydroxypyrrole, 2-pyrazole, 4-hydroxypyridine, 8-hydroxyquinoline, and 4, 5-dihydroxybenzothiazole. The term melanin includes naturally occurring melanins which are usually high molecular weight polymers and low molecular weight polymers as well as melanin analogs as defined below. Naturally occurring melanin includes eumelanins, phacomelanins, neuromelanins and allomelanins. The term melanin is also intended to include trichochromes when used hereafter. The term "melanin" is further intended to include melanin, melanin precursors, melanin analogs, melanin variants and melanin derivatives unless the context dictates otherwise.

Melanin Analog: Melanin in which a structural feature that occurs in naturally occurring or enzymatically produced melanins is replaced by an unusual substituent divergent from substituents traditionally present in melanin. An example of an unusual substituent is selenium in place of sulfur, such as selenocysteine.

Melanin Derivative: This term is intended to include any derivative of melanin which is capable of being converted to either melanin or a substance having melanin activity. An example of a melanin derivative is melanin attached to a dihydrotrigonelline carrier such as described in Bodor, N., Ann. N. Y. Acad. Sci. 507,289 (1987) to enable the melanin to cross the blood-brain barrier. The term melanin derivatives is also intended to include chemical derivatives of melanin, such as an esterified melanin.

Melanin Variant: Melanin variants include various subsets of melanin substances that occur as families of related materials. Included in these subsets, but not limited thereto, are: (1) Naturally occurring melanins produced by whole cells that vary in their chemical and physical characteristics; (2) Enzymatically produced melanins prepared from a variety of precursor substrates under diverse reaction conditions; (3) Melanin analogs in which a structural feature that occurs in (I) or (2) above is replaced by an unusual substituent divergent from the traditional; and (4) Melanin derivatives in which a substituent in a melanin produced in (1). (2) or (3) above is further altered by chemical or enzymatic means.

Tyrosinase: An enzyme which, in mammals, catalyzes: (a) the hydroxylation of tyrosine to dopa (3,4-dihydroxyphenylalanine); (b) the oxidation of dopa to dopaquinone; and (c) may catalyze the oxidation of 5,6-dihydroxyindole to indole-5,6-quinone. All of these reactions catalyzed by tyrosinase take place in the biosynthetic pathway which produces melanin. Tyrosinase is most commonly found in a glycosylated form in vivo.

Melanin Concentrating Hormone: Melanin concentrating hormone (MCH) is a peptide which has been isolated from fish pituitary glands. characterized and synthesized (Kawauchi, H. et al., Nature 305,321 (1983)). MCH has also been localized by immunohistochemistry in the brain and pituitary gland of salmon, frogs and rats (Baker, B. J. et al., Gen. Comp. Endocrinol. 50, 1423 (1983). Naito, N. et al., Neurosci. Lett. 70, 81 (1986), Skotfitsch, G. et al., Proc. Natl. Acad. Sci. USA 83, 1528 (1986) and Zamir, N. et al., Brain Research 373,240 (1986)).

A mammalian MCH-like substance has been detected using salmon MCH antiserum directed against salmon MCH by radioimmunoassay and immunohistochemistry (Zamir. N. et al., Proc. Natl. Acad. Sci. USA, supra). This mammalian MCH exhibits distinct chromatographic properties on both Reversed Phase High Performance Liquid Chromatography (RP-HPLC) and gel chromatography when compared to the fish enzyme. Id. The persistence of this mammalian MCH in the mammalian hypothalamo-neurohypophyseal system suggests a role for MCH in posterior pituitary function, such as the regulation of food and water intake. Id.

Other functions of this mammalian MCH peptide have also been suggested.

For example. due to the identification of MCH fibers in the human median eminence and pituitary stalk, it has been suggested that the peptide causes the aggregation or concentration of melanin in cells of the central nervous system and may be involved in the regulation of anterior pituitary function (Pelletier, G. et al., Brain Research 423.247 (1987)). Furthermore. Sekiya. K. et al. (Neuroscience 25, 925, 1988) suggest that MCH may act as a neurotransmitter and/or neuromodulator in the central nervous system or may regulate the pituitary portal-blood system and/or the neurosecretory system in mammals.

Melanin: Naturally occurring melanins include eumelanins, phaeomelanins, neuromelanins and allomelanins. Trichochromes which are low molecular weight polymers derived from the oxidation of tyrosine are also considered melanins for the purpose of this disclosure.

Melanins and melanin variants are as defined above. Melanin variants are considered melanins for the purpose of this disclosure unless the context indicates otherwise.

The patient or subject to be treated may be any animal or human. The subject is preferably mammalian. In some embodiments the subject is a human. In other embodiments the subject is an animal, more preferably a non-human mammal. The non-human mammal may be a domestic pet, or animal kept for commercial purposes, e.g. a race horse, or farming livestock such as pigs, sheep or cattle. As such the disclosure may have veterinary applications. Non-human mammals include rabbits, guinea pigs, rats, mice or other rodents (including any animal in the order Rodentia), cats, dogs, pigs, sheep, goats, cattle (including cows or any animal in the order Bos), horse (including any animal in the order Equidae), donkey. and non-human primates. The subject may be male or female. The subject may be a patient.

Part A—Methods for Depletion of Guanosine-Containing Nucleosides and Nucleotides: Specialized Diets and Dietary Program for Treatment of Zika and Other Viral Diseases Part A can be implemented using either or both of the following approaches.

Part A1—Administering agents which depletes guanosine-containing nucleosides and nucleotides.

One approach is that of administering agents (e.g. chemicals, or molecules such as immunoglobulins) that have the effect of reducing the content of guanosine-containing nucleosides and nucleotides in particular tissues or the whole body. One way to do this, for example, is that used by mycophenolate and similar compounds that inhibit the IMPDH enzyme. which is necessary for the production of guanosine monophosphate, a key intermediate in the nucleotide synthesis pathway. Another approach would be to administer agents which bind to guanine, or guanosine-containing nucleosides and nucleotides, to reduce their availability.

Part A2—Dietary restriction of guanosine intake and substances used by the body to synthesize guanosine. We describe below specialized diets that we have constructed and used which specifically reduce the dietary intake of guanosine.

It utilizes diets which are low in nucleic acids and their components but which are not nucleotide-free. The diets contain approximately 3% to 50% of the amount by weight of nucleotides seen in the normal western diet (2000 mg/day, from Ekelman, K. Disodium 5'Guanylate and Disodium 5'-Inosate. *WHO Food Additives Series, No.* 32 (1993). and preferably 10%-40%. The percentage of nucleotides, nucleosides, and other nucleic acid components in specific foods has been published by different researchers using various analytic techniques over the years (e.g. Lassek, E, and A Montag. "Nucleic Acid Components in Carbohydrate-rich Food." *Zeitschrift für Lebensnittel-Untersuchung und -Forschung* 190, no. 1 (1990): doi:1689090; Souci, S W, W Fachmann, H Kraut, Eva Kirchhoff, and Forschungsanstalt Forschungsanstalt für Deutsche. *Food Composition and Nutrition Tables*. Stuttgart: Medpharm, 2008; Brulé, D, G Sarwar, and L Savoiet. "Purine Content of Selected Canadian Food Products." *Journal of Food Composition and Analysis* 1, no. 2 (1988): 130-138.). A survey of the world literature on nucleic acid content of foods was conducted. In some cases where the individual nucleotides were not reported, the amount of total nucleotides and of guanosine-containing nucleotides could be estimated from the reported purine content. A set of diets with different percentages of nucleotides (compared to the typical Western diet) was created. These range between about 10% to 40% of the typical Western diet. A registered dietitian created these diets which were low in nucleotides but balanced for other necessary nutrients.

Choosing a diet with a given percent (or range) of nucleotides is optimized by medical evaluation of the condition and needs of the individual patient. Medical evaluation may include the following: level of antibody titers such as those of anti-nuclear antibody, anti-dsDNA antibodies, anti-guanosine antibody, evaluation of the presence and degree of organ damage in kidneys. lungs. joints, brain, and skin, subjective symptomatology such as pain, headaches. and evaluation criteria.

Additionally, it is proposed that all patients with pathogenic infections, and individuals susceptible to developing pathogenic infections, will benefit from diets in which the nucleotide level is 45% or less than the typical western diet, and in which the guanosine and guanosine-containing nucleotides are less than 45% of the typical western diet.

2. The diets initially recommended by the physician to the patient are low in their content of guanine, a nitrogenous base, and/or guanosine, a nucleoside, compared to the usual Western diet. The patient's response to the diet is evaluated over time and diets with sequentially more nucleotide content and more palatability are recommended so that the compliance and tolerability and palatability is at such a level that the patient can for years be maintained on a reduced nucleotide diet. For instance, if the patient is started by the physician on a Step 1 diet, it is likely that after a period of weeks or months the patient will be advanced to a Step 2 diet which has a greater nucleotide content, reflected in a larger range of foods which can be taken, and is therefore more palatable.

(Nucleotide-free diets are described in: Rudolph. F B, A D Kulkarni. W C Fanslow, R P Pizzini, S Kumar, and C T Van Buren. "Role of RNA As a Dietary Source of Pyrimidines and Purines in Immune Function." *Nutrition* 6, no. 1(1990): 45-52; Kulkarni. A D. F B Rudolph, and C T Van Buren. "The Role of Dietary Sources of Nucleotides in Immune Function: A Review." *The Journal of nutrition* 124. no. 8 Suppl (1994): 1442S-1446S.: 45-52).

The inventor's reduced nucleotide diets are fundamentally different from nucleotide-free diets. The nucleotide-free diets used in published animal experiments were almost entirely devoid of nucleotides and were said to contain a level of only 0.001% (Rudolph, F B. A D Kulkarni, W C Fanslow, R P Pizzini, S Kumar, and C T Van Buren. "Role of RNA As a Dietary Source of Pyrimidines and Purines in Immune Function." Nutrition 6, no. 1 (1990): 45-52).

The inventor has conducted extensive analysis of the nucleotide content of human foods from a variety of sources, and evaluated the nutritional content and palatability of potential nucleotide-free diets. The inventor has concluded that it is not practical for most people to stay on a nucleotide-free diet in a compliant manner for the period of months required to obtain substantial clinical benefit from this approach. A nucleotide-free diet is unlikely to be sufficiently palatable for extended use and would deter compliance. Also, use of a nucleotide-free diet for months in humans would likely lead to other dietary deficiencies.

As set forth above, the disclosure provides treatment of a patient with a diet which contains approximately 3% to 50% of the amount by weight of nucleotides seen in the normal western diet, which contains about 2000 mg/day of nucleotides. In exemplary embodiments, the diet of the disclosure contains a nucleotide content of about 1000 mg/day. of about 750 mg/day, of about 500 mg/day, of about 250 mg/day, of about 100 mg/day, of about 75 mg/day, of about 50 mg/day, of about 25 mg/day. In exemplary embodiments, the diet of the disclosure contains a nucleotide content compared to the normal Western diet of about 50%, of about 40%, of about 30%, of about 20%. of about 10%, of about 5%. of about 3%. In exemplary embodiments, the diet of the disclosure contains a nucleotide content compared to the normal Western diet of 3-50%, of about 10-40%, of about 20-30%. of about 3-40%, of about 3-30%, of about 10-30%, of about 10-20%.

2. Example diets: The nucleotide content of one Example Diet is about 28±5% of the typical Western diet. The nucleotide content of another Example Diet is about 43±5% of the typical Western diet.

3. The diet program is comprised of a period of months, e.g. 6 months, during which a physician and a dietician evaluate and work to optimize diet treatment for each pathogenic infection patient.

a. The physician initially evaluates the severity of the patient's disease based on signs and symptoms, laboratory tests, evidence of organ damage, etc., and then recommends a specific diet. The patient is followed over the next few months with repeat followup disease evaluations and diet adjustments by the physician. The patient may be asked to keep, as individually necessary, logs of symptoms such as headaches, skin rashes, joint pains. etc. These logs are periodically reviewed by the physician.

b. The dietician has an initial meeting with the patient in which the practical aspects of the diet program are explained in detail. This first visit includes describing weighing the foods to be included in the diet. characterizing the portion size for each type of food, keeping a food log. advising on the effect of cooking on food nucleotide content, etc. The patient will have one or more followup visits, as well as occasional other phone, email or other communications with the patient to answer questions and direct the treatment.

c. Depending on the severity of the patient's disease, an initial diet will be selected. As the patient stabilizes clinically or based on laboratory testing. the patient will be moved through a series of diets with increasing nucleotide content but which are still substantially lower compared to the typical Western diet. It is believed that for each patient there is a threshold for reactivity, and that if the diets are below that threshold the patient will have successfully minimized signs, symptoms, and progression of the pathogenic infection. The goal of the program is then to put the patient on a convenient and palatable maintenance diet which they can pragmatically follow for a period of years.

d. A specialized version of the low-guanosine diet has been constructed which meets the needs of pregnant women. Part B—Methods for Administering Melanin, and/or Increasing the Body Content of Melanin by Modulation of Metabolic Processes.

Melanin from different sources and in different formulations has been shown to have some therapeutic activity against some viruses, bacteria, fungi and parasites, but is not used clinically at all as far as the inventor has been able to determine. Additionally, melanin is very hard (Majerus. M. E. N., Mclanism. New York: Oxford University Press. 1998) and has been shown to represent a physical barrier to pathogens both on the skin (Tang, Huaping. Regulation and function of the melanization reaction in *Drosophila*. Fly 3 (2009): 105-111) and internally. It is amenable to a wide range of administration methods including topical and parenteral. It is generally considered to be non-toxic itself except to pathogens. Melanin has also been produced from genetically modified organisms including fungi and bacteria.

The present disclosure involves the use of one or more methods from each of Part A and part B. A method from Part A and a method from Part B can be administered together (e.g. in a single formulation, or singly at the same time), or sequentially in any order (e.g. A method from part A followed by a method from part B, or a method from part B followed by a method from part A)

Guanosine—depleting chemicals such as mycophenolate are active against microbes in much lesser doses than those currently used for its main indication that of immunosuppression for transplantation.

The present disclosure has the further advantage that it is unlikely that the Zika virus or other organisms will be able to develop a resistance to both of the different types of attack represented by Part A and Part B together. Another advantage of the present disclosure is that any microbes which were to develop resistance would still be susceptible to other available therapies.

Mycophenolate

As used herein, "mycophenolates" refers herein to mycophenolic acid ("MPA") and its analogs, and their pharmaceutically acceptable salts, derivatives, prodrugs, and metabolites. Exemplary mycophenolates for use in the present disclosure include mycophenolic acid and mycophenylate mofetil. Mycophenolic acid, or 6-(4-hydroxy-6-methoxy-7-methyl-3-oxo-1,3-dihydroisobenzofuran-5-yl)-4-methyl-hex-4-enoic acid, has the structure Mycophenolate mofetil is the 2-morpholinoethyl ester of mycophenolic acid, and has the formula:

Analogs of mycophenolic acid that have high IMPDH-inhibiting activity are also useful in the practice of the present disclosure include compounds with varying substituents in the 2-, 4-, 5-, and 6-positions on the mycophenolate core structure, as well as pharmaceutically acceptable salts, derivatives, prodrugs, and metabolites of such mycophenolate analogs. Such compounds are described for example, in the following U.S. patents incorporated herein by reference: U.S. Pat. No. 5,688,529 Mycophenolate mofetil high dose oral suspensions: U.S. Pat. No. 5,633,279 5-Substituted derivatives of mycophenolic acid U.S. Pat. No. 5,554,612 4-Amino-6-substituted mycophenolic acid and derivatives U.S. Pat. No. 5,538,969 4-Amino derivatives of 5-substituted mycophenolic acid U.S. Pat. No. 5,536,747 6-Substituted mycophenolic acid and derivatives U.S. Pat. No. 5,493,030 5-Substituted derivatives of mycophenolic acid; U.S. Pat. No. 5,444,072 6-Substituted mycophenolic acid and derivatives U.S. Pat. No. 5,441,953 4-Amino derivatives of mycophenolic acid U.S. Pat. No. 5,380,879 Derivatives of mycophenolic acid U.S. Pat. No. 4,861,776 Heterocyclic aminoalkyl esters of mycophenolic acid and derivatives thereof; U.S. Pat. No. 4,753,935 Morpholinoethylesters of mycophenolic acid; U.S. Pat. No. 4,748,173 Heterocyclic aminoalkyl esters of mycophenolic acid and derivatives thereof; U.S. Pat. No. 4,727,069 Heterocyclic aminoalkyl esters of mycophenolic acid, derivatives thereof Dose and administration time of mycophenolic acid for antiviral effects are surprisingly different than the current dose and administration time for prevention of transplant rejection. It is important to understand that mycophenolic acid's anti-viral effect is likely to require a small fraction (about 1-2% or less) of the clinical dose which is approved and commonly used for prevention of transplant rejection. For instance, Chan et al., 2013, p. 612 indicated that for a virus in which mycophenolic acid demonstrated an $EC_{50}$ of 0.17 meg/ml, the usual clinical doses of mycophenolic acid would result in local concentrations 60-300× greater than needed. This is directly comparable for our results. For instance, in one of the Norovirus tests we document here. $EC_{50}$ of 0.151 mcg/mL was reported. Even less mycophenolic acid would be needed to treat viruses such as Influenza A H1N1 and RSV in which we report $EC_{50}<0.10$ mcg/ml. Dramatically lower doses may suffice for mycophenolic acid to treat Zika virus, where a value of EC50 of 0.049 mcg/ml was obtained in one of our tests. Therefore. it is not only possible to achieve adequate body levels of mycophenolic acid to treat these viruses clinically, but also a small fraction of the current clinical dose may be more than adequate. To et al, 2016 also presented data on page 1812 supporting these conclusions.

A second beneficial difference in the administration of the mycophenolic acid for antiviral use compared to its current clinical usage is the following. Mycophenolic acid, when currently used clinically to prevent transplant rejection in an individual patient, typically is given for months or years at doses of 2000 mg to 3000 mg per day, to block lymphocyte cell proliferation. In contrast, the highly effective low dose antiviral treatments of the disclosure may require, for example, just one to two weeks of administration in an individual patient to cure his viral infection.

A third beneficial point is that the combination of low dose and short time of administration of mycophenolic acid to achieve the antiviral effect, is likely to drastically decrease the occurrence of those side effects (adverse events) which have typically been reported clinically where it is currently used at very high dose for very long periods of time. At low dose for short periods of time it is extremely unlikely to have immunosuppressive effects which could be detrimental to the body's resistance to other pathogens.

A fourth beneficial point is that the low dose, short time of administration usage described above may also serve to reduce the teratogenic potential of this drug, which occurs when it is used at high dose for long periods of time.

A fifth beneficial point regarding dosing and time of administration relates to those pathogenic infections which result in development of autoimmunity causing neurological illness such as Guillain-Barre Syndrome, encephalitis, myelitis, paralysis, confusion, weakness, etc. In those situations, for instance, the low effective antiviral dose can be titrated up so that an appropriate degree of mild immunosuppression is achieved simultaneously or shortly after the antiviral effect to block the autoimmunity from causing neurological illness. (It has been demonstrated that the immunosuppressive effect of mycophenolic acid on lymphocytes is dose-dependent, with lower doses having less effect (Vethe et al., 2008).)

For example, West Nile infection is well-documented to cause neurological illness. In a mouse model where West Nile infection leads to neurological illness, administration of appropriate doses of mycophenolic acid is demonstrated to mitigate the degree and occurrence of neurological illness.

The following references are incorporated herein in their entirety: Chan, J. F., Chan, K. H., Kao, R. Y., To, K. K., Zheng, B. J., Li, C. P., Li, P. T., Dai, J., Mok, F. K., Chen, H., Hayden, F. G., Yuen, K. Y. (2013). Broad-spectrum antivirals for the emerging Middle East respiratory syndrome coronavirus. J Infect 67: 606-616. To, K. K., Mok, K. Y., Chan, A. S., Cheung, N. N., Wang, P., Lui, Y. M., Chan, J. F., Chen, H., Chan, K. H., Kao, R. Y., Yuen, K. Y. (2016). Mycophenolic acid, an immunomodulator, has potent and broad-spectrum in vitro antiviral activity against pandemic, seasonal and avian influenza viruses affecting humans. J Gen Virol 97: 1807-1817. Vethe, N. T., Bremer, S., Rootwelt, H., Bergan, S. (2008). Pharmacodynamics of mycophenolic acid in CD4+ cells: a single-dose study of IMPDH and purine nucleotide responses in healthy individuals. Therapeutic drug monitoring 30: 647-655.

Effectiveness of Mycophenolic Acid Against Influenza

1. Data supporting the effectiveness of mycophenolic acid in treating important and currently clinically relevant strains of influenza.

To et al. (2016) pointed out that the demonstration by Chan et al. (2013) of effectiveness of mycophenolic acid against the historical Influenza A(H1N1) strain A/WSN/ 1933 in a chemical screening assay, was insufficient to determine whether it would be effective against other strains of influenza. To et al. (2016) then experimentally showed that mycophenolic acid is effective against pandemic flu H1/415, which is A/Hong Kong/415742/2009, and is sometimes written as A(H1N1)pdm09. They also showed it to be effective against seasonal influenza A(H3N2) virus, and avian-origin influenza A (H7N9), as well as other influenza A and influenza B viruses. These strains which they tested include those which are currently clinically relevant.

2. The disclosure provides for the use of mycophenolic acid to be active also against the following respiratory viruses: Influenza A H3N2; Influenza A H5N1 (low path); Influenza B (Victoria); Influenza B (Yamagata); Parainfluenza virus-3; Rhinovirus-14; Influenza A H7N9 virus; Influenza A H5N1 (high path).

The following references are incorporated herein by reference in their entireties:
Chan, J. F., Chan, K. H., Kao, R. Y., To, K. K., Zheng, B. J., Li, C. P., Li, P. T., Dai, J., Mok, F. K., Chen, H., Hayden, F. G., Yuen, K. Y. (2013). Broad-spectrum antivirals for the emerging Middle East respiratory syndrome coronavirus. J Infect 67: 606-616. To, K. K., Mok, K. Y., Chan, A. S., Cheung, N. N., Wang, P., Lui, Y. M., Chan, J. F., Chen, H., Chan, K. H., Kao, R. Y., Yuen, K. Y. (2016). Mycophenolic acid, an immunomodulator, has potent and broad-spectrum in vitro antiviral activity against pandemic, seasonal and avian influenza viruses affecting humans. J Gen Virol 97: 1807-1817. (First Published Online: 1 Aug. 2016.).

In a Zika Prevention Trial, MPA was pre-incubated with human cells 4 hours or 24 hours before Zika virus infection. In the VYR assays, MPA reduced virus to zero in Huh7 cells pre-incubated with drug for 24 hrs.

Minocycline, Doxycycline, and Other Tetracycline Derivatives for Zika Treatment

The disclosure provides the use of minocycline, doxycycline and other tetracycline derivatives, including for example tetracycline, for the prevention and treatment of infection by pathogenic agents, for example viruses, and in a specific embodiment the Zika virus. Minocycline is a preferred compound because it will also cross the blood brain barrier. Without being bound by any theory, it is believed that the primary mechanism is inhibition of viral replication, but other properties including antioxidant and anti-inflammatory effects on the host cells are believed to contribute. Several tetracycline derivatives have been demonstrated to inhibit other viruses, including retroviruses and other flaviviridae (Chapagain, 2012; Dutta, 2010; Michaelis, 2007; Rothan, 2014).

Chapagain, M. (2012). Minocycline Protects Mice against West nile virus (WNV)-associated severe disease 18th SNIP Scientific Conference. Journal of Neuroimmune Pharmacology 7: 5-81. Dutta, K., Anirban, B. (2011) Use of minocycline in viral infections. Indian Journal of Medical Research 133: 467. Michaelis, M., Kleinschmidt, M. C., Doerr, H. W., Cinatl, J. (2007). Minocycline inhibits West Nile virus replication and apoptosis in human neuronal cells. J Antimicrob Chemother 60: 981-986. Rothan, H. A., Mohamed, Z., Paydar, M., Rahman, N. A., Yusof, R. (2014). Inhibitory effect of doxycycline against dengue virus replication in vitro. Arch Virol 159: 711-718.

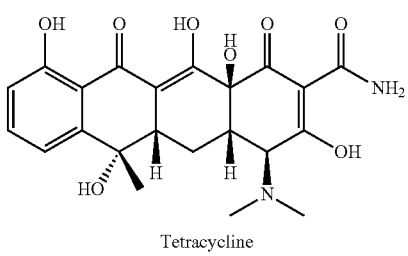

Tetracycline

-continued
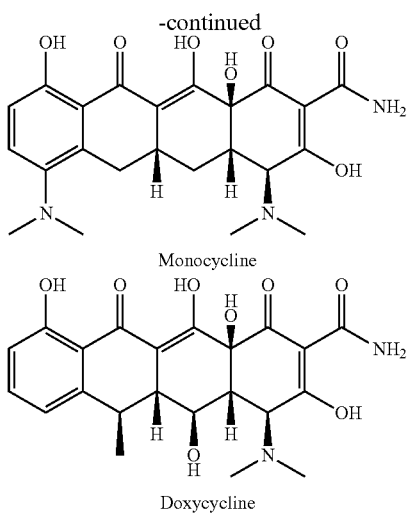
Monocycline
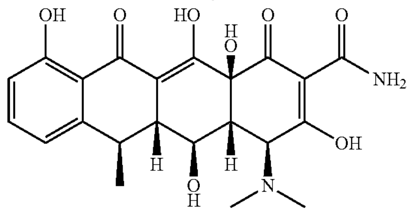
Doxycycline

L-DOPA, Dopamine, and Precursors in the Melanin Synthesis Pathway for Zika Treatment The disclosure provides that L-dopa, dopamine and precursors in the melanin synthesis pathway prevent and treat infection by Zika virus. L-DOPA is a preferred compound because it can be given orally and will also cross the blood brain barrier. Without being bound by any theory, the primary mechanism is believed to be inhibition of viral replication, but other properties including are believed to contribute. It has been proposed that in insects, several compounds in the melanin synthesis pathways are important in insect immunity and have anti-microbial effects (Nappi et al., 2005). L-Dopa has been demonstrated to reduce West Nile virus proliferation somewhat in cell culture, but the RNA levels of the virus were not reduced by L-Dopa (Blazquez et al., 2016). Blázquez, A. B., Martín-Acebes, M. A., Saiz, J. C. (2016). Inhibition of West Nile Virus Multiplication in Cell Culture by Anti-Parkinsonian Drugs. Front Microbiol 7: 296. Nappi, A. J., Christensen. B. M. (2005). Melanogenesis and associated cytotoxic reactions: applications to insect innate immunity. Insect Biochem Mol Biol 35: 443-459.

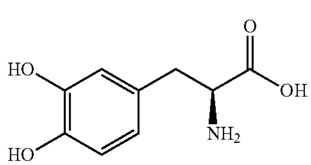

L-DOPA

Therapeutic Use of Melanin Overview

The present disclosure is directed to therapeutic uses of melanin, melanin precursors. melanin derivatives, melanin analogs and related substances. One particular aspect of the disclosure relates to the treatment or prevention of infections by the administration of active substances which cause an increased melanin concentration in the patient's infected tissues. Such substances include melanin, melanin precursors, melanin derivatives, melanin analogs, melanin variants, melanin-concentrating hormone (MCH), tyrosinase, tyrosinase gene and combinations thereof.

In one aspect, the present disclosure a method for treating or preventing pathogenic infections in a mammal comprising administering to a mammal in need of such treatment an amount effective for treating said infections of an agent which causes an increased concentration of melanin and related substance in said infections.

In another aspect, the present disclosure provides a method for preventing pathogenic infections in a mammal comprising administering to a mammal in need of such treatment an amount of an agent effective to prevent said infections of an agent which causes an increased concentration of melanin and related substances in said infections.

In yet another aspect the present disclosure provides a pathogenic infection-healing device selected from a patch, a strip, a dressing or a band comprising an amount of melanin or related substance effective to treat a infections in a mammal.

In yet another aspect the present disclosure provides a pharmaceutical formulation for treating or preventing pathogenic infections in a mammal comprising mineral oil and an infection treating effective amount of an agent which causes an increase in the concentration of melanin in said infected tissues.

In a further aspect, the present disclosure provides a pharmaceutical formulation for treating or preventing pathogenic infections in a mammal comprising another topical antibacterial cream or ointment and a infection-healing effective amount of an agent which causes an increased concentration of melanin and related substances in said infections.

In a still further aspect, the present disclosure provides a method for treating or preventing pathogenic infections in a mammal comprising administering to a mammal in need of such treatment an amount effective to treat said infections of a pharmaceutical formulation which causes an increase in the concentration of melanin in said infected tissues wherein said agent is selected from melanin, melanin precursors, melanin derivatives, melanin analogs, melanin variants, tyrosinase, tyrosinase gene, melanin concentration hormone and mixtures thereof.

In a still further aspect, the present disclosure provides a pharmaceutical formulation for treating or preventing pathogenic infections in a mammal comprising an emollient selected from ammonium lactate, ichthammol ointment and lanolin and an infection-healing effective amount of an agent which causes an increased concentration of melanin and related substances in said infections.

These and other aspects of the present disclosure will be apparent to those of ordinary skill in the art in light of the present description and claims.

Melanins

Melanin is a pigment which is found in many cells and organisms (Majerus. M. E. N., Melanism, New York: Oxford University Press 1998). It is resistant to analysis and degradation by chemical and physical agents (Prota, G., Melanins And Melanogenesis, New York: Academic Press, 1992). Therefore the complete structures of many melanins remain unknown, although a few have been identified and even synthesized (Prota, G., Melanins And Melanogenesis, New York: Academic Press, 1992).

Melanin is naturally found in small packets called melanosomes (Prota, G., Melanins And York: Academic Press, 1992), which are membrane-enclosed vesicles. Melanin is a hard substance (Majerus, M. E. N., Melanism, New York: Oxford University Press, 1998). The presence of many small melanosomes strengthens cells. The melanin in cells is separated by membranes and other cytoplasmic components. This arrangement permits flexibility in movement while preserving hardness to resist pressure.

Melanin is normally present in mammalian skin in cells called melanocytes (Prota. G., Melanins And Melanogenesis. New York: Academic Press, 1992). Melanocytes are most numerous in the epidermis and dermis of the skin, but are present in other tissues such as the eye, some nerves, the brain, and some blood cells.

In the epidermis there is approximately 1 melanocyte to 36 keratinocytes. In the dermis the ratio of melanocytes to fibroblasts is much more variable. Melanin is often found in healed skin (Majerus, M. E. N., Melanism, New York: Oxford University Press, 1998).

Mammalian colors are determined chiefly by two types, cumelanins and phaeomelanins. Eumelanins are derived from the precursor tyrosine and are generally insoluble and black or brown in color. Phacomelanins have as their precursors tyrosine and cysteine and are generally alkali-soluble and lighter in color. Allomelanins ("allo" meaning other) are formed from nitrogen-free precursors, primarily catechol and 1,8-dihydroxynaphthalene (see The Merck Index, Tenth Edition. page 827. item 5629. Melanins). Quinones are the usual intermediates in allomelanin synthesis. The synthesis of melanins occurs in nature as well as being produced synthetically. A further group of low molecular weight yellow, red and violet pigments is known as trichochromes. The trichochromes are usually classified with the melanins, since they serve as pigments and are derived from the oxidation of tyrosine.

The enzyme, tyrosinase, plays a key role in the synthesis of melanin and its derivatives. In mammals. tyrosinase is a glycosylated enzyme found in melanocytes. It has been theorized that tyrosinase functions by means of separate catalytic sites; one site for tyrosinase hydroxylase activity, another site for dopa oxidase activity, and a third independent site for dopa as a cofactor. (Hearing, V. J. et al., Biochem. J., 157: 549 (1976)). Tyrosinase may also play a role in catalyzing the oxidation of 5,6-dihydroxyindole to indole-5,6-quinone. (Korner, A. M. et al., Science 217.1163 (1982)). In vivo, mammalian tyrosinase undergoes extensive modification. When initially synthesized, tyrosinase has an apparent molecular weight of about 55,000. Glycosylation of the enzyme occurs as it is transferred through the Golgi complex and delivered to the melanocytes. (Imokawa, G. et al., J. Invest. Derm., 85,165 (1985)). During this modification of tyrosinase, sialic acid and 4 mol of asparagine-linked carbohydrate chains (containing mannose, glucosamine, galactose and are added to each mole of tyrosinase. (Ferrini, V. et al., Int. J. Biochem. 19,229 (1987)). The glycosylated tyrosinase has an apparent molecular weight of about 70.000. (Laskin, J. D. et al., J. Biol. Chem. 261. 16626 (1986)).

The glycosylated tyrosinase is delivered to the melanocytes by coated vesicles. In the melanocytes, the tyrosinase is membrane bound and aggregates into a high molecular weight form. In vivo, tyrosinase is under active metabolic control involving an active degradation system which results in a biological half-like of about ten hours. (Jimenez, M. et al., Fed. Proc. Fedn. Am. Socs. Exp. Biol. 45.1714 (1986)).

The melanins comprise a family of biopolymer pigments. A frequently used chemical description of melanin is that it is comprised of "heteropolymers of 5-6-dihydroxyindole and 5-6-dihydroxyindole-2-carboxylic acid" (Bettinger et al., 2009). Melanins are polymers produced by polymerization of reactive intermediates. The polymerization mechanisms include, but are not limited to, autoxidation, enzyme-catalyzed polymerization and free radical initiated polymerization. The reactive intermediates are produced chemically, electrochemically. or enzymatically from precursors. Suitable enzymes include, but are not limited to. peroxidases, catalases, polyphenol oxidases, tyrosinases, tyrosine hydroxylases, and laccases. The precursors that are connected to the reactive intermediates are hydroxylated aromatic compounds. Suitable hydroxylated aromatic compounds include, but are not limited to 1) phenols, polyphenols, aminophenols and thiophenols of aromatic or polycyclicaromatic hydrocarbons. including, but not limited to, phenol, tyrosine, pyrogallol, 3-aminotyrosine, thiophenol and α-naphthol; 2) phenols. polyphenols. aminophenols, and thiophenols of aromatic heterocyclic or heteropoly cyclic hydrocarbons such as, but not limited to, 2-hydroxypyrrole, 4-hydroxy-1,2-pyrazole, 4-hydroxypyridine, 8-hydroxyquinoline, and 4,5-dihydroxybenzothiazole.

The term melanin includes naturally occurring melanin polymers as well as melanin analogs as defined below. Naturally occurring melanins include eumelanins, phacomelanins, neuromelanins and allomelanins.

As used here, the term "melanin" refers to melanins, melanin precursors, melanin analogs, melanin variants, melanin derivatives, and melanin-like pigments, unless the context dictates otherwise. The term "melanin-like" also refers to hydrogels with melanin-like pigmentation and quinoid electrophilicity. This electrophilicity can be exploited for facile coupling with biomolecules.

As used herein, the term "melanin analog" refers to a melanin in which a structural feature that occurs in naturally-occurring or enzymatically-produced melanins is replaced by a substituent divergent from substituents traditionally present in melanin. An example of such a substituent is a selenium, such as selenocysteine, in place of sulfur.

As used herein, the term "melanin derivative" refers to any derivative of melanin which is capable of being converted to either melanin or a substance having melanin activity. An example of a melanin derivative is melanin attached to a dihydrotrigonelline carrier such as described in Bodor, N., Ann. N.Y. Acad. Sci. 507, 289 (1987), which enables the melanin to cross the blood-brain barrier. The term melanin derivatives is also intended to include chemical derivatives of melanin, such as an esterified melanin.

As used herein, the term "melanin variant" refers to various subsets of melanin substances that occur as families of related materials. Included in these subsets, but not limited thereto, are:
(1) Naturally occurring melanins produced by whole cells that vary in their chemical and physical characteristics;
(2) Enzymatically produced melanins prepared from a variety of precursor substrates under diverse reaction conditions;
(3) Melanin analogs in which a structural feature that occurs in (1) or (2) above is replaced by an unusual substituent divergent from the traditional; and
(4) Melanin derivatives in which a substituent in a melanin produced in (1), (2) or (3) above is further altered by chemical or enzymatic means.

As used herein, the term "Melanin-like substances" refers to heteropolymers of 5-6-dihydroxyindole and 5-6-dihydroxyindole-2-carboxylic acid which have one or more properties usually associated with natural melanins, such as UV absorption or semiconductor behavior.

Melanin Sources

Melanin and Melanin-like compounds can be obtained:
by extraction and purification from natural sources. e.g. cephalopods such as cuttlefish (e.g. Sepia) or squid (e.g. Loligo), bird feathers (e.g. from species with black strains such as Silkie chickens);

by chemical synthesis, whether water or non-water based e.g. (Deziderio, 2004) (daSilva et al., 2004; Lawrie et al., 2008; Pezzella et al., 2006);

by electrochemical synthesis, e.g. (Meredith et al., 2005);

by bioreactors created by utilization of natural or genetically altered bacteria, fungi, lichens. or viruses e.g. (della-Cioppa, 1998).

Melanin Manufacturing and Fabrication

Melanin and melanin-like compounds can be manufactured as particles, nanoparticles, dust, beads, or fibers that are woven or non-woven e.g. by methods as described by (Greiner and Wendorff, 2007), sheets e.g. (Meredith et al., 2005), films (daSilva et al., 2004), plates, bricks, chars, spheres, nodules, balls, graphite-like sheets and shards, liquids, gels, or solids (e.g. thermoplastic or thermoset). and by common chemical engineering molding and fabrication methods or custom methods. Sheets can range from one molecular layer to several millimeters. Fibers can range from nanometers to several millimeters.

The melanin material may be natural or synthetic, with natural pigments being extracted from plant and animal sources, such as squid, octopus. mushrooms, cuttlefish, and the like. In some cases, it may be desirable to genetically modify or enhance the plant or animal melanin source to increase the melanin production. Melanins are also available commercially from suppliers.

The following procedure describes an exemplary technique for the extraction of melanin from cuttlefish (*Sepia Officinalis*). 100 gm of crude melanin are dissected from the ink sac of 10 cuttlefish and washed with distilled water (3×100 ml). The melanin is collected after each wash by centrifugation (200×g for 30 minutes). The melanin granules are then stirred in 800 ml of 8 M Urea for 24 hours to disassemble the melanosomes. The melanin suspension is spun down at 22.000×g for 100 minutes and then washed with distilled water (5×400 ml). The pellet is washed with 50% aqueous DMF (5×400 ml) until a constant UV baseline is achieved from the washes. Finally. the pellet is washed with acetone (3×400 ml) and allowed to air dry.

Synthetic melanins may be produced by enzymatic conversion of suitable starting materials, as described in more detail hereinbelow. The melanins may be formed in situ within the porous particles or may be preformed with subsequent absorption into the porous particles.

Suitable melanin precursors include but are not limited to tyrosine, 3,4-dihydroxy phenylalanine (dopa). D-dopa, catechol, 5-hydroxyindole, tyramine, dopamine, m-aminophenol, o-aminophenol, p-aminophenol, 4-aminocatechol, 2-hydroxyl-1,4-naphthaquinone (henna), 4-methyl catechol, 3,4-dihydroxybenzylamine, 3,4-dihydroxybenzoic acid, 1,2-dihydroxynaphthalene, gallic acid, resorcinol, 2-chloroaniline, p-chloroanisole, 2-amino-p-cresol, 4,5-dihydroxynaphthalene2,7-disulfonic acid, o-cresol, m-cresol, p-cresol, and other related substances which are capable of being oxidized to tan, brown, or black melanin-like compounds capable of absorbing ultraviolet radiation when incorporated in the polymeric particle matrix of the present disclosure. Combinations of precursors can also be used.

The melanin precursor is dissolved in an aqueous solution, typically at an elevated temperature to achieve complete solution. A suitable amount of the enzyme tyrosinase (EC 1.14.18.1) is added to the solution, either before or after the melanin precursor. The concentration of tyrosinase is not critical, typically being present in the range from about 50 to about 5000 U/ml. The solution is buffered with an acetate, phosphate, or other suitable buffer, to a pH in the range from about 3 to 10. usually in the range from about 5 to 8, more usually being about 7. Melanin-like pigments can be obtained using suitable precursors even in the absence of an enzyme just by bubbling oxygen through a solution of a precursor for an adequate period of time.

Melanin material may be obtained by treatment of, e.g, cuttlefish ink or squid ink in a microwave, optionally with mixing.

Topical Administration of Melanin

Presented below are non limiting categories of topical agents and specific examples of commercially available products into which melanin and related substance may be incorporated. Burn Treatments Silver Sulfadiazine Cream 1% (catalog number. 32886 Henry Schein, Inc.) Emollients Ammonium Lactate Cream (catalog number. 1027036, Henry Schein, Inc.) Ichthammol Ointment-20% (catalog number 1020956. Henry Schein, Inc.) Lanolin (catalog number 1021756, Henry Schein. Inc.

Sun Screen Products Zinc Oxide and ointment (catalog number 4711456, Henry Schein, Inc.) Antibiotics and Antibacterials Bacitracin Ointment (catalog number 4706972, Henry Schein, Inc.) Clindamycin Topical solution (catalog number 1028791. Henry Schein, Inc.) Cream (catalog number 1027125, Henry Schein, Inc.) Erythromycin topical solution (catalog number 4207358, Henry Schein, Inc.) Gentamycin ointment (catalog number 4733872, Henry Schein, Inc.) Nystatin cream (catalog number 4201056, Henry Schein, Inc.) and Antiseborreics Clotrimazole Betamethasone cream (catalog number 1025190. Henry Schein, Inc.) Ketoconoizole Cream (catalog number 1024347. Henry Schein, Inc.) Miconiazole Nitrate Cream (catalog number 2723761. Henry Schein, Inc.) Nystatin Ointment (catalog number 1020986, Henry Schein, Inc.) Antiseptics Alcohol. Isopropyl 91% (catalog number Henry Schein. Inc.) Hydrogen Peroxide (catalog number 1023516. Henry Schein, Inc.) Isopropyl alcohol 70% (catalog number 1024716, Henry Schein, Inc.) Povidone Ointment (catalog number 4722656, Henry Schein, Inc.)

Viruses

A non-exhaustive list of viruses and their species which can be prevented and/or treated by the compostions and methods of the disclosure include, for example: Abadina virus (Reoviridae), Abelson murine leukemia virus (Retroviridae), Abras virus (Bunyaviridae), Absettarov virus (Flaviviridae), Abu Hammad virus (Bunyaviridae), Abu Mina virus (Bunyaviridae), Acado virus (Reoviridae), Acara virus (Bunyaviridae), Acciptrid herpesvirus (Herpesviridae), *Acheta domestica* densovirus (Parvoviridae). *Acrobasis zelleri* entomopoxvirus (Poxviridae), Adelaide River virus (Rhabdoviridae), Adeno-associated virus (Parvoviridae), *Aedes aegypti* densovirus (Parvoviridae), *Aedes aegypti* entomopoxvirus (Poxviridae). *Aedes albopictus* densovirus (Parvoviridae). *Aedes pseudoscutellaris* densovirus (Parvoviridae), African green monkey cytomegalovirus (Herpesviridae), African green monkey HHV-like virus (Herpesviridae), African green monkey polyomavirus (Papovaviridae), African horse sickness viruses (Reoviridae), African swine fever virus, African swine fever-like viruses, AG-virus (Bunyaviridae). AG-virus, (Bunyaviridae), *Agaricus bisporus* virus, Aguacate virus (Bunyaviridae). Ahlum water-borne virus (Tombusviridae). Aino virus (Bunyaviridae), Akabane virus (Bunyaviridae), AKR (endogenous) murine leukemia virus (Retroviridae). Alajuela virus (Bunyaviridae). Alcelaphine herpesvirus (Herpesviridae), Alenquer virus (Bunyaviridae), Aleutian disease virus (Parvoviridae), Aleutian mink disease virus (Parvoviridae). Alfuy virus (Flaviviridae). Allerton virus (Herpesviridae), Allitrich herpesvirus (Herpesviridae), *Allomyces arbuscula* virus, Almeirim virus (Reoviridae), Almpiwar virus (Rhabdoviridae), Altamira virus, (Reoviridae), Amapari virus (Arenaviridae), American ground squirrel herpesvirus, (Herpesviridae), *Amsacta moorei* entomopoxvirus (Poxviridae), Amyelosis chronic stunt virus (Caliciviridae), Ananindeua virus (Bunyaviridae), Anatid herpesvirus (Herpesviridae), Andasibe virus (Reoviridae), Anhanga virus (Bunyaviridae), Anhembi virus (Bunyaviridae), *Anomala cuprea* entomopoxvirus (Poxviridae), *Anopheles* A virus (Bunyaviridae), *Anopheles* virus (Bunyaviridae). Antequera virus (Bunyaviridae). Aotine herpesvirus (Herpesviridae), Apeu virus (Bunyaviridae). Aphodius tasmaniae entomopoxvirus (Poxviridae), Apoi virus (Flaviviridae). Aransas Bay virus (Bunyaviridae), Arbia virus (Bunyaviridae), Arboledas virus (Bunyaviridae). Arbroath virus (Reoviridae). Argentine turtle herpesvirus (Herpesviridae). Arkonam virus (Reoviridae), Aroa virus (Flaviviridae), *Arphia conspersa* entomopoxvirus (Poxviridae), Aruac virus (Rhabdoviridae), Arumowot virus (Bunyaviridae), Asinine herpesvirus (Herpesviridae). Atlantic cod uleus syndrome virus (Rhabodoviridae). Atlantic salmon reovirus Australia (Reoviridae), Atlantic salmon reovirus Canada (Reoviridae). Atlantic salmon reovirus USA (Reoviridae), *Atropa belladorma* virus (Rhabdoviridae), *Aucuba* bacilliform virus, Badnavirus, Aujeszky's disease virus (Herpesviridae), Aura virus (Togaviridae). Auzduk disease virus (Poxviridae), Avalon virus (Bunyaviridae), Avian adeno-associated virus (Parvoviridae), Avian carcinoma, Mill Hill virus (Retroviridae), Avian encephalomyelitis virus (Picornaviridae), Avian infectious bronchitis virus (Coronaviridae). Avian leukosis virus—RSA (Retroviridae), Avian myeloblastosis virus (Retroviridae), Avian myelocytomatosis virus (Retroviridae), Avian nephrites virus (Picornaviridae). Avian paramyxovirus (Paramyxoviridae), Avian reovirus (Reoviridae), B virus (Parvoviridae), B-lymphotropic papovavirus (Papovaviridae), Babahoya virus (Bunyaviridae), Babanki virus (Togaviridae), Baboon herpesvirus (Herpesviridae), Baboon polyomavirus (Papovaviridae), Bagaza virus (Flaviviridae), Bahia Grande virus (Rhabdoviridae). Bahig virus (Bunyaviridae). Bakau virus (Bunyaviridae). Baku virus (Reoviridae). Bald eagle herpesvirus (Herpesviridae), Bandia virus (Bunyaviridae), Bangoran virus (Rhabdoviridae), Bangui virus (Bunyaviridae), Banzi virus (Flaviviridae), Barmah Forest virus (Togaviridae), Barranqueras virus (Bunyaviridae), Barur virus (Rhabdoviridae). Batai virus (Bunyaviridae). Balarna virus (Bunyaviridae), Batken virus (Bunyaviridae), Bauline virus (Reoviridae). Beak and feather disease virus (Circoviridae). BeAn virus (Rhabdoviridae). BeAr virus (Bunyaviridae). Bebaru virus (Togaviridae), Belem virus (Bunyaviridae), Belmont virus ((Bunyaviridae)), Belterra virus (Bunyaviridae). Benevides virus (Bunyaviridae), Benfica virus (Bunyaviridae). Berne virus, (Coronaviridae), Berrimah virus (Rhabdoviridae), Bertioga virus (Bunyaviridae), Bhanja virus (Bunyaviridae), Bimbo virus (Rhabdoviridae), Bimiti virus (Bunyaviridae), Birao virus (Bunyaviridae), BivensArn virus (Rhabdoviridae), BK virus (Papovaviridae), Bluetongue viruses (Reoviridae). Bobaya virus (Bunyaviridae), Bobia virus (Bunyaviridae), Bobwhite quail herpesvirus (Herpesviridae). Boid herpesvirus (Herpesviridae). *Bombyx mori* densovirus (Parvoviridae). Boolarra virus (Nodaviridae), Boraceia virus (Bunyaviridae). Border disease virus (Flaviviridae), Boma disease virus, Botambi virus (Bunyaviridae), Boteke virus, (Rhabdoviridae). Bouboui virus (Flaviviridae), Bovine adeno-associated virus (Parvoviridae), Bovine adenoviruses (Adenoviridae), Bovine astrovirus (Astroviridae), Bovine coronavirus (Coronaviridae), Bovine diarrhea virus (Flaviviridae), Bovine encephalitis herpesvirus (Herpesviridae), Bovine enteric calicivirus (Caliciviridae), Bovine enterovirus (Picornaviridae), Bovine ephemeral fever virus (Rhabdoviridae). Bovine herpesvirus (Herpesviridae), Bovine immunodeficiency virus (Retroviridae). Bovine leukemia virus (Retroviridae), Bovine mamillitis virus (Herpesviridae). Bovine papillomavirus (Papovaviridae). Bovine papular stomatitis virus (Poxviridae), Bovine parainfluenza virus (Paramyxoviridae), Bovine parvovirus (Parvoviridae), Bovine polyomavirus (Papovaviridae), Bovine Respiratory Syncytial Virus (Paramyxoviridae), Bovine rhinovirus (Picornaviridae), Bovine syncytial virus (Retroviridae), Bozo virus (Bunyaviridae). Broadhaven virus (Reoviridae), Bruconha virus (Bunyaviridae), Brus Laguna virus (Bunyaviridae), Budgerigar fledgling disease virus (Papovaviridae), Buenaventura virus (Bunyaviridae), Buffalopox virus (Poxviridae), Buggy Creek virus (Togaviridae), Bujaru virus (Bunyaviridae), Bukalasa bat virus (Flaviviridae), Bunyamwera virus (Bunyaviridae), Bunyip creek virus (Reoviridae), Bushbush virus (Bunyaviridae), Bussuquara virus (Flaviviridae), Bwamba virus (Bunyaviridae), Cache Valley virus (Bunyaviridae), Cacipacore virus (Flaviviridae), Caddo Canyon virus (Bunyaviridae). Caimito virus (Bunyaviridae), Calchaqui virus (Rhabdoviridae), California encephalitis virus (Bunyaviridae), California harbor sealpox virus (Poxviridae), *Callistephus chinensis* chlorosis virus (Rhabdoviridae), Callitrichine herpesvirus (Herpesviridae), Camel contagious cethyma virus (Poxviridae). Camelpox virus (Poxviridae), *Camptochironomus tentans* entomopoxvirus (Poxviridae), Canancia virus (Bunyaviridae), Canarypox virus (Poxviridae), Candiru virus (Bunyaviridae). Canid herpesvirus (Herpesviridae), Caninde virus (Reoviridae), Canine adeno-associated virus (Parvoviridae), Canine adenovirus (Adenoviridae), Canine calicivirus (Caliciviridae), Canine coronavirus (Coronaviridae). Canine distemper virus (Paramyxoviridae). Canine herpcsvirus (Herpesviridae). Canine minute virus (Parvoviridae), Canine oral papillomavirus (Papovaviridae), Canine parvovirus (Parvoviridae), Canna yellow mottle virus (Badnavirus), Cape Wrath virus (Reoviridae), Capim virus (Bunyaviridae), Caprine adenovirus (Adenoviridae), Caprinc arthritis encephalitis virus (Retroviridae). Caprinc herpesvirus (Herpesviridae), Capuchin herpesvirus AL- (Herpesviridae). Capuchin herpesvirus AP- (Herpesviridae). Carajas virus (Rhabdoviridae), Caraparu virus (Bunyaviridae), Carey Island virus (Flaviviridae), Casphalia extranea densovirus (Parvoviridae), Catu virus (Bunyaviridae). Caviid herpesvirus ((Herpesviridae)). CbaAr virus (Bunyaviridae). Cebine herpesvirus (Herpesviridae), Cercopithecine herpesvirus (Herpesviridae), Cervid herpesvirus (Herpesviridae), CG-virus (Bunyaviridae). Chaco virus (Rhabdoviridae). Chagres virus (Bunyaviridae), Chamois contagious ecthyma virus (Poxviridae), Chandipura virus (Rhabdoviridae). Changuinola virus (Reoviridae). Charleville virus (Rhabdoviridae), Chelonid herpesvirus (Herpesviridae), Chelonid herpesvirus (Herpesviridae), Chelonid herpesvirus (Herpesviridae), Chenuda virus (Reoviridae). Chick syncytial virus (Retroviridae), Chicken anemia virus (Circoviridae), Chicken parvovirus (Paruoviridae), Chikungunya virus (Togaviridae), Chilibre virus (Bunyaviridae), Chim virus (Bunyaviridae), Chimpanzee herpesvirus (Herpesviridae), *Chironomus attenuatus* entomopoxvirus (Poxviridae), *Chironomus luridus* entomopoxvirus (Poxviridae), *Chironomus plumosus* erltomopoxvirus (Poxviridae), Chobar Gorge virus (Reoviridae). *Choristoneura biennis* entomopoxvirus (Poxviridae). *Choristoneura conflicta* entomopoxvirus (Poxviridae), *Choristoneura diversuma* entomopoxvirus (Poxviridae), *Chorizagrotis auxiliars* entomopoxvirus (Poxviridae), Chub reovirus Germany (Reoviridae), Ciconiid herpesvirus (Herpesviridae), Clo Mor virus (Bunyaviridae), CoAr-virus (Bunyaviridae), Coastal Plains virus (Rhabdoviridae), Cocal virus (Rhabdoviridae), Coital exanthema virus (Herpesviridae), ColAn-virus (Bunyaviridae). *Colocasia* bobone disease virus. (Rhabdoviridae). Colorado tick fever virus, (Reoviridae), Columbia SK virus, (Picornaviridae), Columbid herpesvirus, (Herpesviridae), Connecticut virus, (Rhabdoviridae), Contagious ecthyma virus, (Poxviridae). Contagious pustular dermatitis virus, (Poxviridae). Corfu virus, (Bunyaviridae), Corriparta virus, (Reoviridae), Cotia virus, (Poxviridae), Cowpox virus, (Poxviridae), Crimean-Congo hemorrhagic fever virus, (Bunyaviridae), CSIRO village virus, (Reoviridae), Cynara virus, (Rhabdoviridae). Cyprinid herpesvirus, (Herpesviridae), Dabakala virus, (Bunyaviridae), D'Aguilar virus, (Reoviridae), Dakar bat virus, (Flaviviridae). DakArk virus, (Rhabdoviridae), Deer papillomavirus, (Papovaviridae), *Demodema boranensis* entomopoxvirus, (Poxviridae), Dengue virus, (Flaviviridae), Dengue virus group. (Flaviviridae), Dependovirus, (Parvoviridae), Dera Ghazi Khan virus, (Bunyaviridae), Dera Ghazi Khan virus Group, (Bunyaviridae), Dermolepida albohirtum entomopoxvirus, (Poxviridae), Dhori virus. (Orthomyxoviridae). Diatraca saccharalis densovirus. (Parvoviridae). Dobrava-Belgrade virus, (Bunyaviridae), Dolphin distemper virus. (Paramyxoviridae), Dolphinpox virus, (Poxviridae). Douglas virus, (Bunyaviridae), Drosophila C virus, (Picornaviridae), Dry Tortugas virus, (Bunyaviridae), duck adenovirus. (Adenoviridae), Duck adenovirus, (Adenoviridae). Duck astrovirus, (Astroviridae), Duck hepatitis B virus, (Hepadnaviridae). Duck plague herpesvirus syn. anatid herpesvirus, (Herpesviridae), Dugbe virus, (Bunyaviridae), Duvenhage virus, (Rhabdoviridae). Eastern equine encephalitis virus, (Togaviridae), Ebola virus Filoviridae, *Echinochloa* hoja blanca virus; Genus Tenuivirus. *Echinochloa* ragged stunt virus, (Reoviridae), ectromelia virus, (Poxviridae), Edge Hill virus, (Flaviviridae), Egtved virus syn. viral hemorrhagic septicemia virus, (Rhabdoviridae), Elapid herpesvirus, (Herpesviridae), Elephant loxondontal herpesvirus, (Herpesviridae), Elephant papillomavirus, (Papovaviridae), Elephantid herpesvirus, (Herpesviridae), Ellidacy virus, (Reoviridae), Embu virus. (Poxviridae), Encephalomyocarditis virus, (Picornaviridae), Enseada virus, (Bunyaviridae), *Entamoeba* virus, (Rhabdoviridae), Entebbe bat virus, (Flaviviridae), Epizootic hemorrhagic disease viruses, (Reoviridae). Epstein-Barr virus, (Herpesviridae), Equid herpesvirus, (Herpesviridae), Equid herpesvirus, (Nerpesviridae), Equid herpesvirus, (Herpesviridae), Equine abortion herpesvirus, (Herpesviridae), Equine adeno-associated virus, (Parvoviridae), Equine adenovirus, (Adenoviridae), Equine arteritis virus, (Arterivirus), Equine cytomegalovirus, (Herpesviridae), Equine encephalosis viruses, (Reoviridae), Equine herpesvirus, (Herpesviridae), Equine infectious anemia virus, (Retroviridae). Equine papillomavirus. (Papovaviridae), Equine rhinopneumonitis virus, (Herpesviridae), Equine rhinovirus, (Picornaviridae), Erel-virus, (Bunyaviridae), Erinaceid herpesvirus, (Herpesviridae), Erve virus, (Bunyaviridae), *Erysimum* latent virus. Tymovirus. Esocid herpesvirus, (Herpesviridae), Essaouira virus, (Reoviridae), Estero Real virus. (Bunyaviridae), Eubenangee virus, (Reoviridae), *Euonymus* fasciation virus, (Rhabdoviridae), European bat virus, (Rhabdoviridae), European brown hare syndrome virus, (Caliciviridae). European elk papillomavirus, (Papovaviridae), European ground squirrel cytomegalovirus, (Herpesviridae), European hedgehog herpesvirus, (Herpesviridae), Everglades virus, (Togaviridae), Eyach virus, (Reoviridae), Facey's Paddock virus, (Bunyaviridae). Falcon inclusion body disease. (Herpesviridae), Falconid herpesvirus, (Herpesviridae), Farallon virus, (Bunyaviridae), Felid herpesvirus, (Herpesviridae). Feline calicivirus, (Caliciviridae), Feline herpesvirus, (Herpesviridae), Feline immunodeficiency virus. (Retroviridae), Feline infectious peritonitis virus, (Coronaviridae), Feline leukemia virus, (Retroviridae), Feline parlleukopenia virus, (Parvoviridae), Feline parvovirus, (Parvoviridae), Feline syncytial virus, (Retroviridae), Feline viral rhinotracheitis virus, (Herpesviridae), Fetal rhesus kidney virus, (Papovaviridae), Field mouse herpesvirus, (Herpesviridae), Figulus subleavis entomopoxvirus, (Poxviridae), Fiji disease virus, (Reoviridae), Fin V-virus, (Bunyaviridae), Finkel-Biskis-Jinkins murine sarcoma virus, (Retroviridae). Flanders virus, (Rhabdoviridae). Flexal virus, (Arenaviridae), Flock house virus, Nodaviridae, Foot-and-mouth disease virus A. (Picornaviridae), Foot-and-mouth disease virus ASIA, (Picornaviridae), Foot-and-mouth disease virus, (Picornaviridae), Forecariah virus, (Bunyaviridae), Fort Morgan virus, (Togaviridae), Fort Sherman virus, (Bunyaviridae), Foula virus, (Reoviridae), Fowl adenoviruses, (Adenoviridae), Fowl calicivirus, (Caliciviridae). Fowlpox virus, (Poxviridae), Fraser Point virus, (Bunyaviridae), Friend murine leukemia virus, (Retroviridae), Frijoles virus, (Bunyaviridae), Frog herpesvirus, (Herpesviridae), Fromede virus, (Reoviridae), Fujinami sarcoma virus, (Retroviridae). Fukuoka virus, (Rhabdoviridae), Gabek Forest virus, (Bunyaviridae), Gadget's Gully virus. (Flaviviridae). *Galleria mellonella* densovirus, (Parvoviridae), Gallid herpesvirus, (Herpesviridae), Gamboa virus, (Bunyaviridae), Gan Gan virus, (Bunyaviridae), Garba virus, (Rhabdoviridae), Gardner-Arnstein feline sarcoma virus, (Retroviridae). Geochelone carbonaria herpesvirus, (Herpesviridae). *Geochelone chilensis* herpesvirus, (Herpesviridae), *Geotrupes sylvaticus* entomopoxvirus. (Poxviridae). *Gerbera* symptomless virus, (Rhabdoviridae). Germiston virus, (Bunyaviridae). Getah virus, (Togaviridae). Gibbon ape leukemia virus. (Retroviridae), Ginger chlorotic fleckvirus, Sobemovirus. Glycine mottle virus, Tombusviridae, Goat herpesvirus, (Herpesviridae), Goatpox virus, (Poxviridae), *Goeldichironomus holoprasimus* cntomopoxvirus. (Poxviridae). Golden shiner reovirus. (Reoviridae). Gomoka virus, (Reoviridae), Gomphrena virus, (Rhabdoviridae). Gonometa virus. (Picornaviridae). Goose adenoviruses. (Adenoviridae), Goose parvovirus, (Parvoviridae), Gordil virus, (Bunyaviridae), Gorilla herpesvirus, (Herpesviridae), Gossas virus, (Rhabdoviridae). Grand Arbaud virus. (Bunyaviridae). Gray Lodge virus, (Rhabdoviridae), Gray patch disease agent of green sea turtle. (Herpesviridae), Great Island virus, (Reoviridae), Great Saltee Island virus, (Reoviridae), Great Saltee virus, (Bunyaviridae), Green iguana herpesvirus, (Herpesviridae). Green lizard herpesvirus, (Herpesviridae), Grey kangaroopox virus, (Poxviridae), Grimsey virus, (Reoviridae). Ground squirrel hepatitis B virus, (Hepadnaviridae). GroupA-K rotaviruses. (Reoviridae). Gruid herpesvirus, (Herpesviridae), GUU-virus, (Bunyaviridae), Guajara virus, (Bunyaviridae), Guama virus, (Bunyaviridae). Guanarito virus, (Arenaviridae). Guaratuba virus, (Bunyaviridae), Guaroa virus, (Bunyaviridae), Guinea pig cytomegalovirus, (Herpesviridae). Guinea pig herpesvirus, (Herpesviridae), Guinea pig type C oncovirus, (Retroviridae), Gumbo Limbo virus, (Bunyaviridae), Gurupi virus, (Reoviridae), H-virus, (Parvoviridae), H virus. (Bunyaviridae), Hamster herpesvirus. (Herpesviridae), Hamster polyomavirus, (Papovaviridae), Hantaan virus, (Bunyaviridae), Hanzalova virus. (Flaviviridae). Hardy- Zuckerman feline sarcoma virus, (Retroviridae). Hare fibroma virus. (Poxviridae), Hart Park virus, (Rhabdoviridae), Hartebeest herpesvirus, (Herpesviridae), Harvey murine sarcoma virus, (Retroviridae), Hazara virus, (Bunyaviridae), HB virus, (Parvoviridae), Hepatitis virus, (Picornaviridae). Hepatitis virus, (Hepadnaviridae). Hepatitis virus, (Flaviviridae), Herpesvirus M, (Herpesviridae), Herpesvirus papio, (Herpesviridae), Herpesvirus platyrrhinae type, (Herpesviridae), Herpesvirus pottos, (Herpesviridae), Herpesvirus saimiri, (Herpesviridae), Herpesvirus salmonis, (Herpesviridae), Herpesvirus sanguinus, (Herpesviridae), Herpesvirus scophthalmus, (Herpesviridae). Herpesvirus sylvilagus, (Herpesviridae). Herpesvirus T. (Herpesviridae), Herpesvirus tarnarinus, (Herpesviridae), Highlands J virus, (Togaviridae), Hirame rhabdovirus, (Rhabdoviridae), Hog cholera virus, (Flaviviridae), HoJo virus, (Bunyaviridae), Hepatitis delta virus, Satellites, Deltavirus, Hsiung Kaplow herpesvirus, (Herpesviridae), Hepatitis E virus, (Caliciviridae), Hepatopancreatic parvo-like virus of shrimps. (Parvoviridae), Heron hepatitis B virus. (Hepadnaviridae), Herpes ateles. (Herpesviridae). Herpes simiac virus. (Herpesviridae), Herpes simplex virus, (Herpesviridae), Herpes virus B, (Herpesviridae), Herpesvirus aotus, (Herpesviridae), Herpesvirus ateles strain. (Herpesviridae), Herpesvirus cuniculi, (Herpesviridae), Herpesvirus cyclopsis, (Herpesviridae), Huacho virus, (Reoviridae). Hughes virus, (Bunyaviridae). Human adenoviruses, (Adenoviridae). Human astrovirus, (Astroviridae), Human calicivirus, (Caliciviridae), Human caliciviruses, (Caliciviridae), Human coronavirus E, (Coronaviridae), Human coronavirus OC, (Coronaviridae), Human coxsackievirus, (Picornaviridae), Human cytomegalovirus, (Herpesviridae). Human echovirus, (Picornaviridae), Human enterovirus, (Picornaviridae), Human foamy virus, (Retroviridae), Human herpesvirus. (Herpesviridae), Human herpesvirus, Nerpesviridae, Human herpesvirus, (Herpesviridae). Human immunodeficiency virus, (Retroviridae), Human papillomavirus, (Papovaviridae), Human parainfluenza virus, (Paramyxoviridae), Human poliovirus, (Picornaviridae), Human Respiratory Syncytial Virus, (Paramyxoviridae), Human rhinovirus. (Picornaviridae), Human spumavirus, (Retroviridae). Human T-lymphotropic virus. (Retroviridae), Humpty Doo virus, (Rhabdoviridae), HV-virus, (Bunyaviridae), Hypr virus, (Flaviviridae). Laco virus. (Bunyaviridae), Ibaraki virus, (Reoviridae), Icoaraci virus, (Bunyaviridae), Ictalurid herpesvirus, (Herpesviridae), Len virus, (Reoviridae), Ife virus, (Reoviridae). Iguanid herpesvirus, (Herpesviridae), Ilesha virus, (Bunyaviridae), Ilheus virus. (Flaviviridae), Inclusion body rhinitis virus, (Herpesviridae), Infectious bovine rhinotracheitis virus. (Herpesviridae), Infectious bursal disease virus. Birnaviridae. Infectious hematopoietic necrosis virus, (Rhabdoviridae), Infectious laryngotracheitis virus, (Herpesviridae), Infectious pancreatic necrosis virus, Birnavirzdae, Influenza A virus (A/PR//(HN), (Orthomyxoviridae), Influenza B virus (B/Lee/), (Orthornyxoviridae), Influenza C virus (C/California/), (Orthomyxoviridae), Ingwavuma virus, (Bunyaviridae), Inini virus, (Bunyaviridae), Inkoo virus, (Bunyaviridae), Inner Frame virus, (Reoviridae), Ippy virus, (Arenaviridae), Irituia virus, (Reoviridae), Isfahan virus, (Rhabdoviridae). Israel turkey meningoencephalitis virus, (Flaviviridae), Issyk-Kul virus, (Bunyaviridae), Itaituba virus, (Bunyaviridae). Itaporanga virus, (Bunyaviridae), Itaqui virus, (Bunyaviridae), Itimirirn virus, (Bunyaviridae), Itupiranga virus, (Reoviridae), Jaagsickte virus, (Retroviridae), Jacareacanga virus, (Reoviridae), Jamanxi virus, (Reoviridae), Jamestown Canyon virus, (Bunyaviridae). Japanaut virus, (Reoviridae), Japanese encephalitis virus, (Flaviviridae), Jan virus, (Reoviridae), JC virus, (Papovaviridae). Joa virus. (Bunyaviridae), Joinjakaka virus, (Rhabdoviridae), Juan Diaz virus, (Bunyaviridae), Jugra virus, (Flaviviridae). Juncopox virus. (Poxviridae). Junin virus. (Arenaviridae), *Junonia coenia* densovirus, (Parvoviridae), Jurona virus, (Rhabdoviridae), Jutiapa virus, (Flaviviridae). K virus. (Papovaviridae), K virus, (Bunyaviridae), Kachemak Bay virus, (Bunyaviridae), Kadarn virus, (Flaviviridae), Kacng Khoi virus. (Bunyaviridae), Kaikalur virus, (Bunyaviridae). Kairi virus, (Bunyaviridae). Kaisodi virus. (Bunyaviridae). Kala Iris virus. (Reoviridae), Kamese virus, (Rhabdoviridae), Karnmavanpettai virus, (Reoviridae), Kannamangalam virus, (Rhabdoviridae), Kao Shuan virus, (Bunyaviridae), Karimabad virus. (Bunyaviridae), Karshi virus, (Flaviviridae). Kasba virus, (Reoviridae), Kasokero virus, (Bunyaviridae), Kedougou virus, (Flaviviridae), Kemerovo virus, (Reoviridae), Kenai virus, (Reoviridae), Kennedya virus Y, Potyviridae, Kern Canyon virus, (Rhabdoviridae), Ketapang virus, (Bunyaviridae), Keterah virus, (Bunyaviridae), Keuraliba virus, (Rhabdoviridae), Keystone virus, (Bunyaviridae). Kharagysh virus. (Reoviridae), Khasan virus. (Bunyaviridae), Kilham rat virus. (Parvoviridae). Kimberley virus, (Rhabdoviridae), Kindia virus. (Reoviridae). Kinkajou herpcsvirus. (Herpesviridae), Kirsten murine sarcoma virus, (Retroviridae), Kismayo virus, (Bunyaviridae), Klamath virus, (Rhabdoviridae), Kokobera virus, (Flaviviridae). Kolongo virus, (Rhabdoviridae). Koolpinyah virus, (Rhabdoviridae), Koongol virus, (Bunyaviridae), Kotonkan virus, (Rhabdoviridae), Koutango virus, (Flaviviridae), Kowanyama virus, (Bunyaviridae), Kumlinge virus, (Flaviviridae), Kunjin virus, (Flaviviridae), Kwatta virus, (Rhabdoviridae), Kyzylagach virus. (Togaviridae), La Crosse virus, (Bunyaviridae), La Joya virus. (Rhabdoviridae), La-Picdad-Michoacan-Mexico virus, (Paramyxoviridae), Lacertid herpesvirus, (Herpesviridae), Lactate dehydrogenase-elevating virus, (Arterivirus), Lagos bat virus, (Rhabdoviridae), Lake Clarendon virus, (Reoviridae), Lake Victoria cormorant herpesvirus, (Herpesviridae), Langat virus, Flaviviridae, Langur virus, (Retroviridae), Lanjan virus, (Bunyaviridae), Lapine parvovirus, (Parvoviridae), Las Maloyas virus, (Bunyaviridae), Lassa virus. (Arenaviridae), Lato river virus, (Tombusviridae), Le Dantec virus, (Rhabdoviridae). Leanyer virus, (Bunyaviridae), Lebombo virus, (Reoviridae), Lednice virus, (Bunyaviridae), Lee virus, (Bunyaviridae). Leporid herpesvirus, (Herpesviridae), *Leucorrhinia dubia* densovirus, (Parvoviridae), Lipovnik virus, (Reoviridae), Liverpool vervet monkey virus, (Herpesviridae), Llano Seco virus, (Reoviridae). *Locusta migratona* entomopoxvirus, (Poxviridae). Lokem virus, (Bunyaviridae), Lone Star virus, (Bunyaviridae), Lorisine herpesvirus, (Herpesviridae). Louping ill virus. Flaviviridae. Lucke frog herpesvirus, (Herpesviridae), Lum virus, (Parvoviridae). Lukuni virus. (Bunyaviridae). Lumpy skin disease virus. (Poxviridae), Lundy virus, (Reoviridae), *Lymantria dubia* densovirus, (Parvoviridae), Lymphocytic choriomeningitis virus, (Arenaviridae), Machupo virus, (Arenaviridae), Macropodid herpesvirus (Herpesviridae), Madrid virus, (Bunyaviridae), Maguari virus, (Bunyaviridae), Main Drain virus, (Bunyaviridae), Malakal virus, (Rhabdoviridae), Malignant catarrhal fever virus of European cattle, (Herpesviridae), Malpais Spring virus, (Rhabdoviridae), *Malva silvestris* virus, (Rhabdoviridae). Manawa virus, (Bunyaviridae), Manawatu virus, (Nodaviridae), Manitoba virus, (Rhabdoviridae), Manzanilla virus, (Bunyaviridae), Map turtle herpesvirus, (Herpesviridae), Mapputta virus, (Bunyaviridae), Maprik virus, (Bunyaviridae), Maraba virus, (Rhabdoviridae), Marburg virus, (Filoviridae), Marco virus, (Rhabdoviridae). Marck's disease herpesvirus, (Herpesviridae), Marituba virus, (Bunyaviridae). Marmodid herpesvirus, (Herpesviridae). Marmoset cytomegalovirus, (Herpesviridae). Marmoset herpesvirus, (Herpesviridae). Marmosetpox virus, (Poxviridae). Marrakai virus, (Reoviridae). Mason-Pfizer monkey virus, (Retroviridae), Masou salmon reovirus, (Reoviridae), Matruh virus, (Bunyaviridae), Matucare virus, (Reoviridae), Mayaro virus, (Togaviridae), Mboke virus, (Bunyaviridae), Meaban virus, (Flaviviridae), Measles (Edmonston) virus, (Paramyxoviridae), Medical Lake macaque herpesvirus, (Herpesviridae), *Melanoplus sanguinipes* entomopoxvirus, (Poxviridae). Melao virus, (Bunyaviridae), Mcleagrid herpesvirus, (Herpesviridae), Melilotus latent virus, (Rhabdoviridae). *Melolontha melolontha* entomopoxvirus, (Poxviridae), Mengovirus. (Picornaviridae). Mermet virus. (Bunyaviridae). Mice minute virus, (Parvoviridae), Mice pneumotropic virus, (Papovaviridae), *Microtus pennsylvanicus* herpesvirus, (Herpesviridae), Middelburg virus, (Togaviridae), Miller's nodule virus, (Poxviridae), Mill Door virus, (Reoviridae), Minatitlan virus, (Bunyaviridae), Mink calicivirus, (Caliciviridae), Mink enteritis virus, (Parvoviridae), Minnal virus, (Reoviridae), *Mirabilis* mosaic virus, Caulimovirus, Mirim virus, (Bunyaviridae), Mitchell river virus, (Reoviridae). Mobala virus, (Arenaviridae), Modoc virus, (Flaviviridae), Moju virus, (Bunyaviridae). Mojui dos Campos virus, (Bunyaviridae), Mokola virus, (Rhabdoviridae), Molluscum contagiosum virus. (Poxviridae). Molluscum-likepox virus, (Poxviridae), Moloney murine sarcoma virus, (Retroviridae), Moloney virus, (Retroviridae), Monkey pox virus, (Poxviridae), Mono Lake virus, (Reoviridae), *Montana myotis* leukoencephalitis virus, (Flaviviridae), Monte Dourado virus, (Reoviridae), Mopeia virus, (Arenaviridae), Moriche virus, (Bunyaviridae), Mosqueiro virus, (Rhabdoviridae). Mossuril virus. (Rhabdoviridae), Mount Elgon bat virus, (Rhabdoviridae), Mouse cytomegalovirus, (Herpesviridae). Mouse Elberfield virus, (Picornaviridae). Mouse herpesvirus strain, (Herpesviridae), Mouse mammary tumor virus, (Retroviridae), Mouse thymic herpesvirus, (Herpesviridae), Movar herpesvirus, (Herpesviridae), Mucambo virus, (Togaviridae), Mudjinbarry virus, (Reoviridae), Muir Springs virus, (Rhabdoviridae). Mule deerpox virus, (Poxviridae), Multimammate mouse papillomavirus, (Papovaviridae), Mumps virus, (Paramyxoviridae), Murid herpesvirus, (Herpesviridae), Murine adenovirus, (Adenoviridae), Z murine adenovirus, (Adenoviridae), Murine hepatitis virus, (Coronaviridae), Murine herpesvirus, (Herpesviridae). Murine leukemia virus, (Retroviridae), Murine parainfluenza virus, (Paramyxoviridae), Murine poliovirus, (Picornaviridae), Murine polyomavirus, (Papovaviridae), Murray Valley encephalitis virus, (Flaviviridae), Murre virus, (Bunyaviridae), Murutucu virus, (Bunyaviridae), Mykines virus, (Reoviridae), Mynahpox virus, (Poxviridae). Myxoma virus, (Poxviridae), Nairobi sheep disease virus, (Bunyaviridae), Naranjal virus, (Flaviviridae), Nasoule virus, (Rhabdoviridae). Navarro virus, (Rhabdoviridae), Ndelle virus, (Reoviridae), Ndumu virus, (Togaviridae), Neckar river virus, (Tombusviridae), Negishi virus, (Flaviviridae), Nelson Bay virus, New Minto virus, (Rhabdoviridae). Newcastle disease virus, (Paramyxoviridae), Ngaingan virus, (Rhabdoviridae), Ngari virus, (Bunyaviridae), Ngoupc virus, (Reoviridae), Nile crocodilepox virus, (Poxviridae), Nique virus, (Bunyaviridae), Nkolbisson virus, (Rhabdoviridae), Nola virus, (Bunyaviridae), North Clett virus, (Reoviridae), North End virus, (Reoviridae). Northern cereal mosaic virus, (Rhabdoviridae), Northern pike herpesvirus, (Herpesviridae), Northway virus, (Bunyaviridae), NorwaLk virus, (Caliciviridae), Ntaya virus, (Flaviviridae), Nugget virus, (Reoviridae), Nyabira virus, (Reoviridae), Nyamanini virus, Unassigned. Nyando virus, (Bunyaviridae), Oak-Vale virus, (Rhabdoviridae), Obodhiang virus, (Rhabdoviridae), Oceanside virus, (Bunyaviridae), Ockelbo virus, (Togaviridae), Odrenisrou virus, (Bunyaviridae), *Oedaleus senegalensis* entomopoxvirus, (Poxviridae). Oita virus, (Rhabdoviridae). Okhotskiy virus, (Reoviridae). Okola virus, (Bunyaviridae), Olifantsvlei virus, (Bunyaviridae), Omo virus, (Bunyaviridae), Omsk hemorrhagic fever virus, (Flaviviridae), Onchorhynchus masou herpesvirus, (Herpesviridae), O'nyong-nyong virus, (Togaviridae). Operophtera brurnata entomopoxvirus, (Poxviridae). Orangutan herpesvirus, (Herpesviridae), Orf virus, (Poxviridae), Oriboca virus, (Bunyaviridae), Oriximina virus, (Bunyaviridae), Oropouche virus, (Bunyaviridae), Orungo virus, (Reoviridae), Oryctes rhinoceros virus. Unassigned. Ossa virus, (Bunyaviridae), Ouango virus, (Rhabdoviridae), Oubi virus. (Bunyaviridae). Ourem virus, (Reoviridae), Ovine adeno-associated virus, (Parvoviridae). Ovine adenoviruses, (Adenoviridae), (Astroviridae), Ovine herpesvirus. (Herpesviridae), Ovine pulmonary adenocarcinoma virus, (Retroviridae), Owl hepatosplenitis herpesvirus, (Herpesviridae). P virus, (Bunyaviridae), Pacheco's disease virus, (Herpesviridae). Pacora virus, (Bunyaviridae). Pacui virus, (Bunyaviridae). Pahayokee virus. (Bunyaviridae), Palestina virus, (Bunyaviridae), Palyam virus, (Reoviridae), Pan herpesvirus, (Herpesviridae), Papio Epstein-Barr herpesvirus, (Herpesviridae), Para virus, (Bunyaviridae). Pararnushir virus, (Bunyaviridae), Parana virus, (Arenaviridae), Parapoxvirus of red deer in New Zealand, (Poxviridae), Paravaccinia virus, (Poxviridae), Parma wallaby herpesvirus, (Herpesviridae). Paroo river virus, (Reoviridae), Parrot herpesvirus, (Herpesviridae), Parry Creek virus, (Rhabdoviridae), Pata virus, (Reoviridae). Pates monkey herpesvirus pH delta, (Herpesviridae), Pathum Thani virus, (Bunyaviridae). Patois virus, (Bunyaviridae), Peaton virus, (Bunyaviridae). Percid herpesvirus, (Herpesviridae). Perdicid herpesvirus, (Herpesviridae), Perinet virus, (Rhabdoviridae). *Peripianata fuliginosa* densovirus- (Parvoviridae). Peste-des-petits-ruminants virus. (Paramyxoviridae). Petevo virus. (Reoviridae), Phalacrocoracid herpesvirus. (Herpesviridae), Pheasant adenovirus, (Adenoviridae), Phnom-Penh bat virus, (Flaviviridae), Phocid herpesvirus, (Herpesviridae), Phocine (scal) distemper virus, (Paramyxoviridae), Pichinde virus, (Arenaviridae). Picola virus. (Reoviridae), *Picris rapac* densovirus, (Parvoviridae), Pigeon herpesvirus, (Herpesviridae). Pigeonpox virus, (Poxviridae), Badnavirus Piry virus, (Rhabdoviridae), *Pisum* virus, (Rhabdoviridae). Pixuna virus, (Togaviridae), Playas virus, (Bunyaviridae), Pleuronectid herpesvirus, (Nerpesviridae), Pneumonia virus of mice, (Paramyxoviridae), Pongine herpesvirus, (Herpesviridae), Pongola virus. (Bunyaviridae), Ponteves virus, (Bunyaviridae), Poovoot virus, (Reoviridae), Porcine adenoviruses, (Adenoviridae), Porcine astrovirus, (Astroviridae), Porcine cireovirus, Circoviridae, Porcine enteric calicivirus, (Caliciviridae). Porcine enterovirus, (Picornaviridae), Porcine epidemic diarrhea virus, (Coronaviridae), Porcine hemagglutinating encephalomyelitis virus, (Coronaviridae). Porcine parvovirus, (Parvoviridae), Porcine respiratory and reproductive syndrome, (Arterivirus), Porcine rubulavirus, (Paramyxoviridae), Porcine transmissible gastroenteritis virus. (Coronaviridae), Porcine type C oncovirus, (Retroviridae), Porton virus, (Rhabdoviridae), Potosi virus, (Bunyaviridae). Powassan virus, (Flaviviridae), Precarious Point virus, (Bunyaviridae), Pretoria virus, (Bunyaviridae). Primate calicivirus, (Caliciviridae), Prospect Hill virus, (Bunyaviridae). *Pseudaletia includens* densovirus, (Parvoviridae). Pseudocowpox virus, (Poxviridae), Pseudolumpy skin disease virus, (Herpesviridae), Pseudorabies virus, (Herpesviridae). Psittacid herpesvirus, (Herpesviridae), Psittacinepox virus, (Poxviridae), Puchong virus, (Rhabdoviridae), Pueblo Viejo virus, (Bunyaviridae), Puffin Island virus, (Bunyaviridae), Punta Salinas virus, (Bunyaviridae), Punta Toro virus, (Bunyaviridae), Purus virus, (Reoviridae), Puumala virus, (Bunyaviridae), Qalyub virus, (Bunyaviridae), Quailpox virus, (Poxviridae), Quokkapox virus, (Poxviridae), Rabbit coronavirus, (Coronaviridae), Rabbit fibroma virus, (Poxviridae). Rabbit hemorrhagic disease virus. (Caliciviridae), Rabbit kidney vacuolating virus, (Papovaviridae), Rabbit oral papillomavirus, (Papovaviridae), Rabbitpox virus, (Poxviridae), Rabies virus, (Rhabdoviridae), Raccoon parvovirus. (Parvoviridae), Raccoonpox virus, (Poxviridae). Radi virus, (Rhabdoviridae). Rangifer tarandus herpesvirus, (Herpesviridae), Ranid herpesvirus, (Herpesviridae), *Raphanus* virus, (Rhabdoviridae). Rat coronavirus, (Coronaviridae). Rat cytomegalovirus, (Herpesviridae), Rat virus, R. (Parvoviridae), Raza virus, (Bunyaviridae). Razdan virus, (Bunyaviridae). Red deer herpesvirus, (Herpesviridae), Red kangaroopox virus, (Poxviridae). Reed Ranch virus, (Rhabdoviridae). herpesvirus, (Herpesviridae), Reindeer papillomavirus, (Papovaviridae), Reptile calicivirus, (Caliciviridae), Resistencia virus, (Bunyaviridae), Restan virus, (Bunyaviridae), Reticuloendotheliosis virus, (Retroviridae), Rhesus HHV-like virus, (Herpesviridae), Rhesus leukocyte associated herpesvirus strain, (Herpesviridae), Rhesus monkey cytomegalovirus. (Herpesviridae), Rhesus monkey papillomavirus, (Papovaviridae), Rheumatoid arthritis virus, (Parvoviridae), Rift Valley fever virus, (Bunyaviridae), Rinderpest virus, (Paramyxoviridae), Rio Bravo virus, (Flaviviridae), Rio Grande virus, (Bunyaviridae). RML virus, (Bunyaviridae), Rochambeau virus, (Rhabdoviridae), Rocio virus, (Flaviviridae), Ross River virus, (Togaviridae), Rost Islands virus, (Reoviridae), Rous sarcoma virus, (Retroviridae). Royal farm virus, (Flaviuiridae). RT parvovirus, (Parvoviridae), Rubella virus. (Togaviridae), Russian spring summer encephalitis virus, (Flaviviridae), S-virus, (Reoviridae), SA virus, (Herpesviridae), Sabio virus. (Arenaviridae). Sabo virus, (Bunyaviridae), Saboya virus, (Flaviviridae), Sacbrood virus, (Picornaviridae), Sagiyama virus, (Togaviridae), Saimiriine herpesvirus. (Herpesviridae), SaintAbb's Head virus, (Reoviridae), Saint-Floris virus, (Bunyaviridae), Sakhalin virus, (Bunyaviridae). Sal Vieja virus. (Flaviviridae). Salanga virus, (Bunyaviridae). Salangapox virus, (Poxviridae), Salchabad virus, (Bunyaviridae), Salmonid herpesvirus, (Herpesviridae). *Salmonis* virus, (Rhabdoviridae), *Sambucus* vein clearing virus, (Rhabdoviridae), SanAngelo virus, (Bunyaviridae), San Juan virus, (Bunyaviridae). San Miguel sealion virus, (Caliciviridae), San Perlita virus, (Flaviviridae), Sand rat nuclear inclusion agents, (Herpesviridae). Sandfly fever Naples virus. (Bunyaviridae). Sandfly fever Sicilian virus, (Bunyaviridae). Sandjimba virus. (Rhabdoviridae), Sango virus, (Bunyaviridae), Santa Rosa virus, (Bunyaviridae). Santarem virus, (Bunyaviridae), Sapphire II virus, (Bunyaviridae), Saraca virus, (Reoviridae), *Sarracenia purpurea* virus, (Rhabdoviridae), Sathuperi virus, (Bunyaviridae), Saumarez Reef virus, (Flaviviridae), Sawgrass virus, (Rhabdoviridae), *Schistocerca gregaria* entomopoxvirus, (Poxviridae), Sciurid herpesvirus, (Herpesviridae), Sciurid herpesvirus, (Herpesviridae), Scalpox virus, (Poxviridae), Seletar virus, (Reoviridae) Semliki Forest virus, (Togaviridae), *Sena* Madureira virus, (Rhabdoviridae) Sendai virus, (Pararmyxoviridae), Seoul Virus. (Bunyaviridae), Sepik virus, (Flaviviridae), Serra do Navio virus, (Bunyaviridae), Shamonda virus, (Bunyaviridae). Shark River virus, (Bunyaviridae), Sheep associated malignant catarrhal fever of, (Herpesviridae), Sheep papillomavirus. (Papovaviridae), Sheep pulmonary adenomatosis associated herpesvirus. (Herpesviridae), Sheeppox virus, (Poxviridae), Shiant Islands virus, (Reoviridae), Shokwe virus, (Bunyaviridae), Shope fibroma virus, (Poxviridae), Shuni virus. (Bunyaviridae), *Sibine fusca* densovirus, (Parvoviridae), Sigma virus, (Rhabdoviridae), Sikte water-borne virus, (Tombusviridae). Silverwater virus, (Bunyaviridae). virus. (Bunyaviridae). Simian adenoviruses. (Adenoviridae), Simian agent virus, (Papovaviridae), Simian enterovirus, (Picornaviridae). Simian foamy virus, (Retroviridae), Simian hemorrhagic fever virus, (Arterivirus), Simian hepatitis A virus, (Picornaviridae). Simian immunodeficiency virus, (Retroviridae). Simian parainfluenza virus, (Paramyxoviridae), Simian rotavirus SA, (Reoviridae), Simian sarcoma virus, (Retroviridae), Simian T-lymphotropic virus, (Retroviridae), Simian type D virus, (Retroviridae), Simian vancella herpesvirus. (Herpesviridae), Simian virus, (Papovaviridae). *Simulium vittatum* densovirus, (Parvoviridae). Sindbis virus, (Togaviridae), Sixgun city virus. (Reoviridae). Skunkpox virus. (Poxviridae), Smelt reovirus, (Reoviridae), Snakehead rhabdovirus, (Rhabdoviridae), Snowshoe hare virus, (Bunyaviridae), Snyder-Theilen feline sarcoma virus, (Retroviridae), Sofyn virus, (Flaviviridae), Sokoluk virus, (Flaviviridae), Soldado virus, (Bunyaviridae), Somerville virus, (Reoviridae). Sparrowpox virus, (Poxviridae), Spectacled caimanpox virus, (Poxviridae), SPH virus, (Arenaviridae), Sphenicid herpesvirus. (Herpesviridae). Spider monkey herpesvirus, (Herpesviridae), Spondweni virus, (Flaviviridae), Spring viremia of carp virus, (Rhabdoviridae), Squirrel fibroma virus. (Poxviridae), Squirrel monkey herpesvirus, (Herpesviridae), Squirrel monkeyretrovirus, (Retroviridae), SR-virus, (Bunyaviridae), Sripurvirus, (Rhabdoviridae), StAbbs Head virus, (Bunyaviridae), St. Louis encephalitis virus. (Flaviviridae), Starlingpox virus. (Poxviridae), Stratford virus, (Flaviviridae), Strigid herpesvirus, (Herpesviridae), Striped bass reovirus, (Reoviridae), Striped Jack nervous necrosis virus, (Nodaviridae), Stump-tailed macaque virus, (Papovaviridae), Suid herpesvirus, (Herpesviridae). Sunday Canyon virus, (Bunyaviridae), Sweetwater Branch virus, (Rhabdoviridae), Swine cytomegalovirus, (Herpesviridae), Swine infertility and respiratory syndrome virus, (Arterivirus). Swinepox virus. (Poxviridae), Tacaiuma virus, (Bunyaviridae), Tacaribe virus, (Arenaviridae), Taggart virus, (Bunyaviridae). Tahyna virus, (Bunyaviridae). Tai virus, (Bunyaviridae), Taiassui virus, (Bunyaviridae). Tamana bat virus. (Flaviviridae), Tamdy virus, (Bunyaviridae), Tamiami virus, (Arenaviridae), Tanapox virus. (Poxviridae), Tanga virus, (Bunyaviridae), Tanjong Rabok virus, (Bunyaviridae), Taro bacilliform virus, (Badnavirus), Tataguine virus. (Bunyaviridae). Taterapox virus. (Poxviridae), Tehran virus. (Bunyaviridae), Telok Forest virus, (Bunyaviridae), Tembe virus, (Reoviridae). Tembusu virus, (Flaviviridae). Tench reovirus. (Reoviridae), Tensaw virus, (Bunyaviridae), Tephrosia symptomless virus, (Tombusviridae), Termcil virus, (Bunyaviridae), Tete virus, (Bunyaviridae), Thailand virus. (Bunyaviridae). Theiler's murine encephalomyelitis virus. (Picornaviridae), Thermoproteus virus. Lipothrixviridae, Thiafora virus, (Bunyaviridae), Thimiri virus, (Bunyaviridae), Thogoto virus, (Orthomyxoviridae), Thormodseyjarklettur virus, (Reoviridae), Thottapalayam virus, (Bunyaviridae), Tibrogargan virus, (Rhabdoviridae). Tick-borne encephalitis virus, (Flaviviridae), Tillamook virus, (Bunyaviridae), Tilligerry virus, (Reoviridae), Timbo virus, (Rhabdoviridae), Tilmboteua virus, (Bunyaviridae), Tilmaroo virus, (Bunyaviridae), Tindholmur virus. (Reoviridae). Tlacotalpan virus, (Bunyaviridae), Toscana virus, (Bunyaviridae). Tradescantia/Zebrina virus, Potyviridae, Trager duck spleen necrosis virus, (Retroviridae), Tree shrew adenovirus. (Adenoviridae), Tree shrew herpesvirus, (Herpesviridae), *Triatoma* virus, (Picornaviridae), Tribec virus, (Reoviridae), Trivittatus virus. (Bunyaviridae). Trombetas virus, (Bunyaviridae), Trubanarnan virus, (Bunyaviridae), Tsuruse virus, (Bunyaviridae). Tucunduba virus, (Bunyaviridae), Tumor virus X. (Parvoviridae). Tupaia virus. (Rhabdoviridae), Tupaiid herpesvirus, (Herpesviridae). Turbot herpesvirus, (Herpesviridae), Turbot reovirus, (Reoviridae), Turkey adenoviruses. (Adenoviridae). Turkey coronavirus, (Coronaviridae), Turkey herpesvirus, (Herpesviridae), Turkey rhinotracheitis virus, (Paramyxoviridae). Turkeypox virus, (Poxviridae), Turlock virus, (Bunyaviridae), Turuna virus, (Bunyaviridae), Tyuleniy virus, (Flaviviridae) Uasin Gishu disease virus, (Poxviridae), Uganda S virus. (Flaviviridae). Ulcerative disease rhabdovirus, (Rhabdoviridae), Umatilla virus. (Reoviridae), Umbre virus, (Bunyaviridae), Una virus, (Togaviridae), Upolu virus, (Bunyaviridae), UR sarcoma virus, (Retroviridae). Urucuri virus, (Bunyaviridae). Usutu virus, (Flaviviridae). Uting a virus, (Bunyaviridae), Utive virus, (Bunyaviridae), Uukuniemi virus, (Bunyaviridae) Vaccinia subspecies, (Poxviridae), Vaccinia virus, (Poxviridae), Vaeroy virus, (Reoviridae), Varicella-zoster virus, (Herpesviridae), Variola virus, (Poxviridae), Vellore virus, (Reoviridae), Venezuelan equine encephalitis virus, (Togaviridae), Vesicular exanthema of swine virus, (Caliciviridae), Vesicular stomatitis Alagoas virus, Rkabdoviridae, Vesicular stomatitis Indiana virus, (Rhabdoviridae). Vesicular stomatitis New Jersey virus, (Rhabdoviridae), Vilyuisk virus, (Picornaviridae), Vinces virus, (Bunyaviridae), Viper retrovirus, (Retroviridae), Viral hemorrhagic septicemia virus, (Rhabdoviridae), Virgin River virus, (Bunyaviridae), Virus III, (Herpesviridae), Visna/maedi virus, (Retroviridae), Volepoxvirus, (Poxviridae), Wad Medani virus, (Reoviridae), Wallal virus, (Reoviridae), Walleye epidermal hyperplasia, (Herpesviridae), Wanowric virus, (Bunyaviridae), Warrego virus, (Reoviridae), Weddel water-borne virus, Tombusviridae, Weldona virus, (Bunyaviridae), Wesselsbron virus, (Flaviviridae), West Nile virus. (Flaviviridae). Western equine encephalitis virus, (Togaviridae), Wexford virus, (Reoviridae), Whataroa virus, (Togaviridae), Wildbeest herpesvirus, (Herpesviridae), Witwatersrand virus, (Bunyaviridae), Wongal virus, (Bunyaviridae), Wongorr virus, (Reoviridae), Woodchuck hepatitis B virus, (Hepadnaviridae), Woodchuck herpesvirus marmota, (Herpesviridae). Woolly monkey sarcoma virus, (Retroviridae), Wound tumor virus, (Reoviridae), WVU virus, (Reoviridae), WW virus, (Reoviridae), Wyeomyia virus, (Bunyaviridae). Xiburema virus, (Rhabdoviridae), Xingu virus, (Bunyaviridae), Y sarcoma virus, (Retroviridae). Yaba monkey tumor virus, (Poxviridae), Yaba-virus, (Bunyaviridae), Yaba-virus, (Bunyaviridae), Yacaaba virus, (Bunyaviridae), Yaounde virus, (Flaviviridae), Yaquina Head virus, (Reoviridae). Yata virus, (Rhabdoviridae). Yellow fever virus, (Flaviviridae). Yogue virus, (Bunyaviridae), Yokapox virus, (Poxviridae), Yokase virus, (Flaviviridae), *Yucca* baciliform virus, Badnavirus, Yug Bogdanovac virus, (Rhabdoviridae). Zaliv Terpeniya virus, (Bunyaviridae). *Zea mays* virus, (Rhabdoviridae), Zegla virus, (Bunyaviridae). Zika virus, (Flaviviridae), Zirqa virus. (Bunyaviridae).

Pathogenic Infections

In a preferred embodiment the pathogen is an intracellular pathogen, i.e. a pathogen capable of growing and reproducing inside the cells of a host. Bacterial examples which may be prevented and/or treated by the compositions and methods of the disclosure include but are not limited to *Francisella tularensis, Listeria monocytogenes, Salmonella, Brucella, Legionella, Mycobacterium, Nocardia, Rhodococcus equi, Yersinia, Neisseria meningitidis, Chlamydia, Rickettsia, Coxiella, Mycobacterium*, such as *Mycobacterium leprae* and *Treponema pallidum*. Fungal examples include but are not limited to *Histoplasma capsulatum, Cryptococcus neoformans* and *Pneumocystis jirovecii*. Examples of protozoa include but are not limited to Apicomplexans (e.g. *Plasmodium* spp., *Toxoplasma gondii* and *Cryptosporidium parvum*) and Trypanosomatids (e.g. *Leishmania* spp. and *Trypanosoma cruzi*).

The following is an exemplary but non-limiting discussion of various disease agents that could be the subject of prevention and/or treatment in accordance with the present disclosure.

Bacterial Pathogens

There are hundreds of bacterial pathogens in both the Gram-positive and Gram-negative families that cause significant illness and mortality around the word, despite decades of effort developing antibiotic agents. Antibiotic resistance is a growing problem in bacterial disease. Bacterial pathogens may be prevented and/or treated by the compostions and methods of the disclosure.

One of the bacterial diseases with highest disease burden is tuberculosis, caused by the bacterium *Mycobacterium tuberculosis*, which kills about 2 million people a year, mostly in sub-Saharan Africa. Pathogenic bacteria contribute to other globally important diseases, such as pneumonia, which can be caused by bacteria such as *Streptococcus* and *Pseudomonas*, and food borne illnesses, which can be caused by bacteria such as *Shigella, Campylobacter*, and *Salmonella. Pathogenic bacteria also cause infections such as tetanus, typhoid fever, diphtheria, syphilis, and leprosy.*

Conditionally pathogenic bacteria are only pathogenic under certain conditions, such as a wound facilitates entry of bacteria into the blood, or a decrease in immune function. For example, *Staphylococcus* or *Streptococcus* are also part of the normal human flora and usually exist on the skin or in the nose without causing disease, but can potentially cause skin infections, pneumonia, meningitis, and even overwhelming sepsis, a systemic inflammatory response producing shock, massive vasodilation and death. Some species of bacteria. such as *Pseudomonas aeruginosa. Burkholderia cenocepacia*, and *Mycobacterium avium*, are opportunistic pathogens and cause disease mainly in people suffering from immunosuppression or cystic fibrosis.

Other bacteria invariably cause disease in humans, such as obligate intracellular parasites (e.g., *Chlamydophila, Ehrlichia, Rickettsia*) that are capable of growing and reproducing only within the cells of other organisms. Still, infections with intracellular bacteria may be asymptomatic, such as during the incubation period. An example of intracellular bacteria is *Rickettsia*. One species of *Rickettsia* causes typhus, while another causes Rocky Mountain spotted fever. *Chlamydia*, another phylum of obligate intracellular parasites, contains species that can cause pneumonia or urinary tract infection and may be involved in coronary heart disease. *Mycobacterium, Brucella, Francisella, Legionella*, and *Listeria* can exist intracellular, though they are facultative (not obligate) intracellular parasites.

Gram-positive bacteria include *Staphylococcus aureus; Staphylococcus epidermidis; Staphylococcus saprophyticus; Streptococcus pyogenes* (Lancefield group A, beta-hemolytic); *Streptococcus agalactiae* (Lancefield group B, beta-hemolytic); *Streptococcus Viridans* group (most are alpha-hemolytic) including, for example, the *Mitus* group (*S. mitus, S. sanguis, S. parasanguis, S. gordonii, S. crista, S. infantis, S. oralis, S. peroris*), the *Salivarius* group (*S. salivarius, S. vestibularis, S. thermophilus*), the *Mutans* group (*S. mutans, S. sobrinus, S. criceti, S. rattus*, S. downei, S. *macacae*), and the *Anginosus* group (*S. anginosus. S. constellatus, S. intermedius*); *Streptococcus*, e.g., *S. bovis*, S. equinus (Lancefield group D, alpha-hemolytic); *Streptococcus pneumoniae* (no Lancefield antigen; alpha-hemolytic); *Peptostreptococcus* and *Peptococcus; Enterococcus faecalis; Enterococcus faecium; Corynebacterium* diphtheria; *Bacillus anthracis; Bacillus cereus; Clostridium C. botulinum* (more rarely, *C. baratii* and *C. butyricum*); *Clostridium tetani; Clostridium perfringens; Clostridium difficile; Clostridium sordellii; Listeria monocytogenes; Actinomyces israelii; Nocardia* asteroids; *Streptomyces.*

Gram-negative bacteria include *Neisseria meningitides; Neisseria* gonorrhoea; *Moraxella* (subgenera *Branhamella*) *catarrhalis*; Kingella (most commonly kingae); *Acinetobacter baumannii, Oligella ureolytica; Oligella urethralis; Escherichia coli; Shigella* (*S. dysenteriae, S. flexneri, S. boydii, S. sonnei*); *Salmonella* non typhoidal, including *S. enterica* serotype *enteritidis, S. enterica* serotype *typhimurium, S. enterica* serotype *Choleraesuis, S. bongori, Salmonella S. enterica* serotype *Typhi; Yersinia enterocolitica, Klebsiella pneumoniae; Proteus mirabilis; Enterobacter*; Cronobacter (formerly called *Enterobacter sakazakii*); *Serratia; Edwardsiella; Citrobacter; Hafnia; Providencia; Vibrio cholera; Vibrio parahemolyticus; Campylobacter; Helicobacter* (formerly called *Campylobacter*) *pylori, Pseudomonas aeruginosa; Burkholderia cepacia; Burkholderia mallei; Burkholderia pseudomallei; Stenotrophomonas maltophilia; Bacteroides fragilis, Bacteroides melaninogenicus; Fusobacterium; Haemophilus* influenza; *Haemophilus ducreyi; Gardnerella* (formerly called *Haemophilus*) *vaginalis; Bordetella pertussis; Legionella; Yersinia pestis; Francisella tularensis: Brucella B. melitensis* (infects sheep/goats); *B. abortus* (abortions in cows); *B. suis* (pigs); *B. canis* (dogs); *B. maris* (marine animals); *Pasteurella multocida; Streptobacillus moniliformis*; Spirillum minus; *Treponema pallidum; Treponema pallidum* subspecies pertenue; *Treponema pallidum* subspecies *endemicum; Treponema pallidum* subspecies caratcum; *Borrelia burgdorferi; Borrelia; Leptospira; Chlamydia trachomatis; Chlamydia* pneumonia; *Chlamydia psittaci; Rickettsiae rickettsia; Rickettsiae akari; Rickettsiae prowazekii; Rickettsiae typhi; Rickettsiae tsutsugamushi; Rickettsiae parkeri; Rickettsiae africae; Rickettsia conorii; Rickettsia australis; Rickettsia siberica; Rickettsia japonica; Bartonella Quintana; Bartonella henselae; Bartonella bacilliformis; Coxiella burnetii; Ehrlichia; Anaplasma phagocytophilum; Neorickettsia; Orientia; Klebsiella granulomatis* (formerly called *Calymmatobacterium granulomatis*); Capnocytophaga.

Other bacteria include *Mycobacterium tuberculosis; Mycobacterium bovis; Mycobacterium leprae; Mycobacterium avium-intracellulare* or *avium* complex (MAI or MAC); *Mycobacterium ulcerans; Mycobacterium kansasii; Mycobacterium marinum; Mycobacterium scrofulaceum; Mycobacterium fortuitum; Mycobacterium chelonei; Mycobacterium abscessus; Mycoplasma* pneumonia; *Ureaplasma urealyticum.*

Viral Pathogens

Vaccines may be developed for any viral pathogen for which protective antibodies are available. Viruses include DNA and RNA viruses. These include respiratory viruses such as Adenoviruses, Avian influenza, Influenza virus type A. Influenza virus type B, Measles. Parainfluenza virus, Respiratory syncytial virus (RSV), Rhinoviruses, and SARS coronavirus, gastro-enteric viruses such as Coxsackie viruses, enteroviruses such as Poliovirus and Rotavirus, hepatitis viruses such as Hepatitis B virus. Hepatitis C virus, Bovine viral diarrhea virus (surrogate), herpes viruses such as Herpes simplex 1. Herpes simplex 2. Human cytomegalovirus, and Varicella zoster virus, retroviruses such as Human immunodeficiency virus 1 (HIV-1), and Human immunodeficiency virus 2 (HIV-2). as well as Dengue virus, Hantavirus. Hemorrhagic fever viruses, Lymphocytic choriomeningitis virus, Smallpox virus, Ebola virus, Rabies virus, West Nile virus (WNV) and Yellow fever virus.

Examples of viruses which may be prevented and/or treated by the compostions and methods of the disclosure include Parvoviridae; Papovaviridae (Human papilloma virus (HPV); BK polyomavirus; JC polyomavirus); Adenoviridae (Adenovirus, types 40 and 41); Herpesviridae (simplex virus type 1 (HHV-1); Herpes simplex virus type 2 (HHV-2); Macacine herpesvirus 1; Varicella-zoster virus (VZV; HHV-3); Epstein-Barr virus (EBV; HHV-4); Cytomegalovirus (CMV; HHV-5); Human Herpesvirus 6 (HHV-6); HHV-7; Kaposi's sarcoma-associated herpesvirus (HHV-8); Hepadnaviridae (Hepatitis B virus); Poxviridae (Smallpox (Variola major); Alastrim (Variola minor); Vaccinia; Cowpox; Monkeypox; Goat pox, pseudocowpox virus, bovine papular stomatitis virus, tanapox, volepox and related pox viruses such as avipox, buffalopox, racoonpox, squirrelpox, etc.); Molluscum contagiosum; Picornaviridae (Polio virus; Coxsackie A virus; Coxsackie B; virus; Foot and mouth disease; ECHO virus; Hepatitis A virus; Rhinovirus); Astroviridae; Caliciviridae (Norwalk virus; Norovirus; Sapoviruses; Hepatitis E virus); Reoviridae (Rotavirus); Togaviridae (Alpha viruses; Western equine encephalitis (WEE) virus; Eastern equine encephalitis (EEE) virus; Venezuelan equine encephalitis (VEE) virus; Chikungunya virus; Rubivirus (rubella)); Flaviviridae (Yellow fever virus; Dengue virus; St. Louis encephalitis virus; Japanese encephalitis virus; Tick-borne encephalitis virus; Omsk hemorrhagic fever virus; Al Khumra virus; Kyasanur Forest disease virus; Louping ill virus; West Nile virus; Kunjin virus; Murray Valley fever virus; Powassan virus; Hepatitis C virus; Hepatitis G virus); Coronaviridae (Respiratory illness (cold); Severe Acute Respiratory Syndrome)-corona virus (SARS-CoV)); Bunyaviridae (California encephalitis virus; La Crosse virus; Rift Valley fever virus; Phleboviruses; Sandfly fever virus; Nairovirus; Hantavirus); Orthomyxoviridae (Influenza virus (types A. B & C); Paramyxoviridae (Parainfluenza virus; Respiratory syncytial virus (RSV); Hendra virus disease (formerly equine morbillivirus); Nipah virus encephalitis; Mumps Measles; Newcastle disease virus); Rhabdoviridae (Rabies virus); Filoviridae (Marburg virus (acute hemorrhagic fever); Ebola virus (acute hemorrhagic fever)); Arenaviridae (Lymphocytic choriomeningitis virus; Lassa fever virus; Lujo virus; Chapare virus; Junin virus; Machupo virus; Guanarito virus; Sabia virus); Retroviridae (Human Immunodeficiency virus (HIV) types I and II; Human T-cell leukemia virus (HLTV) type I; Human T-cell leukemia virus (HLTV) type II; Spumaviruses; Xenotropic murine leukemia virus-related (XMRV).

Fungal Pathogens

Pathogenic fungi are fungi that cause disease in humans or other organisms. The pathogenic fungi which may be prevented and/or treated by the compositions and methods of the disclosure include but are not limited to the following.

*Candida* species are important human pathogens that are best known for causing opportunist infections in immunocompromised hosts (e.g., transplant patients. AIDS sufferers, and cancer patients). Infections are difficult to treat and can be very serious. *Aspergillus* can and does cause disease in three major ways: through the production of mycotoxins; through induction of allergic responses; and through localized or systemic infections. With the latter two categories, the immune status of the host is pivotal. The most common pathogenic species are *Aspergillus fumigatus* and *Aspergillus flavus*. *Cryptococcus neoformans* can cause a severe form of meningitis and meningo-encephalitis in patients with HIV infection and AIDS. The majority of *Cryptococcus* species lives in the soil and do not cause disease in humans. *Cryptococcus laurentii* and *Cryptococcus albidus* have been known to occasionally cause moderate-to-severe disease in human patients with compromised immunity. *Cryptococcus gattii* is endemic to tropical parts of the continent of Africa and Australia and can cause disease in non-immunocompromised people. *Histoplasma capsulatum* can cause histoplasmosis in humans, dogs and cats. *Pneumocystis jirovecii* (or *Pneumocystis carinii*) can cause a form of pneumonia in people with weakened immune systems. such as premature children, the elderly, transplant patients and AIDS patients. Stachybotrys chartarum or "black mold" can cause respiratory damage and severe headaches. It frequently occurs in houses in regions that are chronically damp.

Examples include *Malassezia furfur; Exophiala werneckii; Microsporum* species; *Trichophyton* species; *Epidermophyton floccosum; Sporothrix schenckii; Phialophora verrucosa; Cladosporium carrinonii; Fonsecaea* species; *Coccidioides; Histoplasma capsulatum; Blastomyces dermatitidis; Cryptococcus neoformans; Cryptococcus gattii; Candida albicans; Aspergillus fumigatus; Aspergillus flavus; Aspergillus niger; Rhizopus; Rhizomucor; Mucor; Exserohilum*.

Parasites

Parasite presents a major health issue. particularly in under-developed countries around the world. Significant pathogenic parasites which may be prevented and/or treated by the compositions and methods of the disclosure include worms (roundworms, flatworms) and protozoa. *Entamoeba histolytica; Giardia lamblia; Trichomonas vaginalis; Plasmodium falciparum; Plasmodium malariae; Plasmodium ovale; Plasmodium vivax; Trypanosoma cruzi; Ascaris lumbricoides; Trichinella spiralis; Toxoplasma gondii; Leishmania donovani; Leishmania tropica; Leishmania braziliensis; Schistosoma mansoni; Schistosoma japonicum; Schistosoma haematobium; Cyclospora* cayetanensis; *Cryptosporidium*, e.g., *C. parvum, C. hominis; Cystoisospora* species (formerly called *Isospora* species), e.g., *C. belli; Naegleria fowleri; Acanthamoeba* species; *Sappinia diploidea; Sappinia pedata; Balamuthia mandrillaris; Pneumocystis jiroveci* (formerly called *Pneumocystis carinii*); *Plasmodium knowlesi; Babesia microti; Babesia divergens; Babesia duncani; Babesia* (no species name yet but designated MO-1); *Trypanosoma brucei* rhodesiense; *Trypanosoma brucei gambiense; Balantidium coli; Dientamoeba fragilis;* Phylum: Microsporidia; *Sarcocystis; Baylisascaris; Necator americanus; Ancylostoma duodenale; Strongyloides stercoralis; Trichinella pseudospiralis; Trichinella nelsoni; Trichinella britovi; Trichinella nativa; Trichuris trichiura; Enterobius vermicularis; Anisakis simplex; Pseudoterranova decipiens; Trichostrongylus; Oesophagostomum*, e.g., *O. bifurcom; Angiostrongylus; Capillaria; Dirofilaria; Loa boa; Onchocerca volvulus; Wuchereria bancrofti; Brugia malayi; Brugia timori; Mansonella, M. perstans; M. streptocerca; M. ozzardi; Dracunculus mediensis;* Cutaneous larva migrans (commonly *Ancylostoma braziliense*=dog hookworm; also *A. caninum, A. ceylanicum*, and *Uncinaria stenocephala*); Visceral larva migrans (most commonly *Toxocara canis*=dog roundworm, less commonly *Toxocara cati*=cat roundworm. *Baylisascaris procyonis*=raccoon roundworm) or ocular larva migrans or neural larva migrans (*B. procyonis*); *Gnathostoma G. spinigerum* and *G. hispidum; Dicrocoelium dendriticum; Echinostoma*, e.g., *E. hortense, E. macrorchis, E. revolutum, E. ilocanu*, and *E. perfoliatum; Thelazia; Shistosoma japonicum; Shistosoma mansoni; Shistosoma haematobium; Shistosoma intercalatum; Shistosoma mekongi; Austrobilharzia variglandis* and other schistosomes; *Tacnia solium; Tacnia saginata; Tacnia multiceps; Tacnia serialis; Tacnia asiatica; Diphyllobothrium latum; Hymenolepsis nana; Echinococcus; Paragonimus; Clonorchis sinensis; Dipylidium caninum; Fasciola, F. hepatica; F. gigantica; Fasciolopsis buski; Heterophyes heterophyes; Hymenolepsis, H. nana, H. dimnuta; Opisthorchis; Bertiella*, e.g., *B. studeri* and *B. mucronata; Macracanthorhynchus hirudinaceous; Moniliformis moniliformis; Bolbosoma* species; *Metagonimus yokogawai; Dioctophyme renale; Mesocestoides*, e.g., *M. lineatus* and *M. variabilis; Philophthalmus*, e.g., *P. lacrymosus, P. gralli, P. palpebrarum; Spirometra*, e.g., *S. mansoni, S. ranarum, S. mansonoides, S. erinacei; Sparganum proliferum*.

Pharmaceutical Dosage Forms

The compositions of the present disclosure can be processed by agglomeration, air suspension chilling, air suspension drying, balling, coacervation, coating, comminution, compression, cryopelletization, encapsulation, extrusion, wet granulation, dry granulation, homogenization, inclusion complexation, lyophilization, melting, microencapsulation, mixing, molding, pan coating, solvent dehydration, sonication, spheronization, spray chilling, spray congealing, spray drying, or other processes known in the art. The compositions can be provided in the form of a minicapsule, a capsule, a tablet, an implant, a troche, a lozenge (minitablet), a temporary or permanent suspension, an ovule, a suppository, a wafer, a chewable tablet, a quick or fast dissolving tablet, an effervescent tablet, a buccal or sublingual solid, a granule, a film, a sprinkle, a pellet, a bead, a pill, a powder, a triturate. a platelet, a strip or a sachet. Compositions can also be administered as a "dry syrup", where the finished dosage form is placed directly on the tongue and swallowed or followed with a drink or beverage. These forms are well known in the art and are packaged appropriately. The compositions can be formulated for oral, nasal, buccal, ocular, urethral, transmucosal, vaginal, topical or rectal delivery.

The pharmaceutical composition can be coated with one or more enteric coatings, seal coatings, film coatings, barrier coatings, compress coatings, fast disintegrating coatings, or enzyme degradable coatings. Multiple coatings can be applied for desired performance. Further. the dosage form can be designed for immediate release, pulsatile release, controlled release, extended release, delayed release, targeted release, synchronized release, or targeted delayed release. For release/absorption control, solid carriers can be made of various component types and levels or thicknesses of coats. with or without an active ingredient. Such diverse solid carriers can be blended in a dosage form to achieve a desired performance. The definitions of these terms are known to those skilled in the art. In addition, the dosage form release profile can be affected by a polymeric matrix composition, a coated matrix composition, a multiparticulate composition, a coated multiparticulate composition, an ion-exchange resin-based composition, an osmosis-based composition. or a biodegradable polymeric composition. Without wishing to be bound by theory. it is believed that the release may be effected through favorable diffusion, dissolution, erosion, ion-exchange, osmosis or combinations thereof.

When formulated as a capsule, the capsule can be a hard or soft gelatin capsule, a starch capsule, or a cellulosic capsule. Although not limited to capsules, such dosage forms can further be coated with, for example, a seal coating, an enteric coating, an extended release coating, or a targeted delayed release coating. These various coatings are known in the art, but for clarity, the following brief descriptions are provided: seal coating, or coating with isolation layers: Thin layers of up to 20 microns in thickness can be applied for variety of reasons. including for particle porosity reduction, to reduce dust, for chemical protection, to mask taste, to reduce odor, to minimize gastrointestinal irritation, etc. The isolating effect is proportional to the thickness of the coating. Water soluble cellulose ethers are preferred for this application. HPMC and ethyl cellulose in combination, or Eudragit E100, may be particularly suitable for taste masking applications. Traditional enteric coating materials listed elsewhere can also be applied to form an isolating layer.

Extended release coatings are designed to effect delivery over an extended period of time. The extended release coating is a pH-independent coating formed of, for example, ethyl cellulose, hydroxypropyl cellulose, methylcellulose, hydroxymethyl cellulose, hydroxyethyl cellulose, acrylic esters, or sodium carboxymethyl cellulose. Various extended release dosage forms can be readily designed by one skilled in art to achieve delivery to both the small and large intestines, to only the small intestine, or to only the large intestine, depending upon the choice of coating materials and/or coating thickness.

Enteric coatings are mixtures of pharmaceutically acceptable excipients which are applied to, combined with, mixed with or otherwise added to the carrier or composition. The coating may be applied to a compressed or molded or extruded tablet, a gelatin capsule, and/or pellets, beads, granules or particles of the carrier or composition. The coating may be applied through an aqueous dispersion or after dissolving in appropriate solvent. Additional additives and their levels, and selection of a primary coating material or materials will depend on the following properties: 1. resistance to dissolution and disintegration in the stomach; 2. impermeability to gastric fluids and drug/carrier/enzyme while in the stomach; 3. ability to dissolve or disintegrate rapidly at the target intestine site; 4. physical and chemical stability during storage; 5. non-toxicity; 6. easy application as a coating (substrate friendly); and 7. economical practicality.

Dosage forms of the compositions of the present disclosure can also be formulated as enteric coated delayed release oral dosage forms, i.e., as an oral dosage form of a pharmaceutical composition as described herein which utilizes an enteric coating to affect release in the lower gastrointestinal tract. The enteric coated dosage form may be a compressed or molded or extruded tablet/mold (coated or uncoated) containing granules, pellets, beads or particles of the active ingredient and/or other composition components, which are themselves coated or uncoated. The enteric coated oral dosage form may also be a capsule (coated or uncoated) containing pellets. beads or granules of the solid carrier or the composition, which are themselves coated or uncoated.

Delayed release generally refers to the delivery so that the release can be accomplished at some generally predictable location in the lower intestinal tract more distal to that which would have been accomplished if there had been no delayed release alterations. The preferred method for delay of release is coating. Any coatings should be applied to a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as an enteric coating in the practice of the present disclosure to achieve delivery to the lower gastrointestinal tract. Polymers for use in the present disclosure are anionic carboxylic polymers.

Shellac, also called purified lac, a refined product obtained from the, resinous secretion of an insect. This coating dissolves in media of pH>7. Colorants, detackifiers, surfactants, antifoaming agents, lubricants, stabilizers such as hydroxy propyl cellulose, acid/base may be added to the coatings besides plasticizers to solubilize or disperse the coating material, and to improve coating performance and the coated product.

In carrying out the method of the present disclosure, the combination of the disclosure may be administered to mammalian species, such as dogs. cats. humans. etc. and as such may be incorporated in a conventional systemic dosage form, such as a tablet, capsule, elixir or injectable. The above dosage forms will also include the necessary carrier material, excipient, lubricant, buffer. antibacterial, bulking agent (such as mannitol), anti-oxidants (ascorbic acid of sodium bisulfite) or the like.

The dose administered must be carefully adjusted according to age, weight and condition of the patient, as well as the route of administration, dosage form and regimen and the desired result.

The pharmaceutical compositions of the disclosure may be administered in the dosage forms in single or divided doses of one to four times daily. It may be advisable to start a patient on a low dose combination and work up gradually to a high dose combination.

Tablets of various sizes can be prepared, e.g., of about 1 to 2000 mg in total weight, containing one or both of the active pharmaceutical ingredients, with the remainder being a physiologically acceptable carrier of other materials according to accepted pharmaceutical practice. These tablets can be scored to provide for fractional doses. Gelatin capsules can be similarly formulated.

Liquid formulations can also be prepared by dissolving or suspending one or the combination of active substances in a conventional liquid vehicle acceptable for pharmaceutical administration so as to provide the desired dosage in one to four teaspoonful.

Dosage forms can be administered to the patient on a regimen of, for example, one, two, three, four, five, six, or other doses per day In order to more finely regulate the dosage schedule, the active substances may be administered separately in individual dosage units at the same time or carefully coordinated times. Since blood levels are built up and maintained by a regulated schedule of administration, the same result is achieved by the simultaneous presence of the two substances. The respective substances can be individually formulated in separate unit dosage forms in a manner similar to that described above.

In formulating the compositions, the active substances, in the amounts described above, may be compounded according to accepted pharmaceutical practice with a physiologically acceptable vehicle, carrier, excipient, binder, preservative, stabilizer, flavor. etc., in the particular type of unit dosage form.

Illustrative of the adjuvants which may be incorporated in tablets are the following: a binder such as gum tragacanth, acacia, corn starch or gelatin; an excipient such as dicalcium phosphate or cellulose; a disintegrating agent such as corn starch, potato starch, alginic acid or the like; a lubricant such as stearic acid or magnesium stearate; a sweetening agent such as sucrose, aspartame, lactose or saccharin; a flavoring agent such as orange, peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both. A syrup of elixir may contain the active compound, water, alcohol or the like as the carrier, glycerol as solubilizer. sucrose as sweetening agent, methyl and propyl parabens as preservatives, a dye and a flavoring such as cherry or orange.

One embodiment of this disclosure includes methods of treating, preventing, or diagnosing a particular disease or condition by administering the disclosed nanoparticles, composite nanoparticles, nanosuspension, or nanocapsules to a subject. In many instances, the nanoparticles, composite nanoparticles, or nanocapsules are administered alone or can be included within a pharmaceutical composition. An effective amount of a pharmaceutical composition, generally, is defined as that amount sufficient to ameliorate, reduce, minimize, or limit the extent of the disease or condition. More rigorous definitions may apply. including elimination, eradication, or cure of the disease or condition.

"Nanoparticles" are solid particles of an average particle diameter of. for example. less than about 1 micron (micrometer). One micron is 1,000 nanometers (nm). "Stabilized" nanoparticles are nanoparticles coated with a stabilizing material and having a reduced tendency for aggregation and loss of dispersion with respect to nanoparticles of the compound of the disclosure without a stabilizing coating. A nano-spray is a spray containing nanoparticles or a spray that produces nanoparticles. A nanodispersion is a dispersion containing nanoparticles. A nanosuspension is a suspension containing nanoparticles.

The liquid formulations useful herein may comprise a solvent. solution. suspension. microsuspension, nanosuspension, emulsion. microemulsion, gel or even a melt containing the active component or components. In some embodiments the nanoparticles, nanofibers, or nanofibrils may be in the form of, or within or on, granules, powders, suspensions, solutions, dissolvable films, mats. webs. tablets, or releasable forms particularly releasable dosage forms. Other particular useful forms are concentrates to which a diluting liquid is added prior to use. The product may also be sprayed onto the inner surface of a container to which a liquid is added later prior to use and the nanoparticles, nanofibers, or nanofibrils, are released into the liquid. Pharmaceutical compositions of the present disclosure can include nanoparticles, composite nanoparticles, nanosuspension, or nanocapsules of the present disclosure.

The composition may also include various antioxidants to retard oxidation of one or more active ingredient or nanoparticles, composite nanoparticles, nanosuspension, or nanocapsules. The prevention of the action of microorganisms can be brought about by preservatives such as various antibacterial and antifungal agents, including but not limited to parabens (e.g., methylparabens, propylparabens), chlorobutanol, phenol. sorbic acid, thimerosal or combinations thereof.

In order to increase the effectiveness of a treatment with the nanoparticles, nanogels, composite nanoparticles, nanosuspension, or nanocapsules of the present disclosure, it may be desirable to combine these nanoparticles, composite nanoparticles, or nanocapsules with other therapies effective in the treatment of a particular disease or condition.

The formulations as described above may be administered for a prolonged period, that is, for as long as the potential for a disease or condition remains or the symptoms continue.

Neurological Symptoms

Mycophenolic Acid and Zika Neurological Disease

The disclosure provides that mycophenolic acid and the other pharmaceutical compositions and methods of the disclosure will prevent, mitigate, and treat neurological disease resulting from infection by Zika virus.

Neurological sequelae of Zika infection include: Guillain Barre Syndrome, encephalitis, myelitis, encephalomyelitis, meningitis, meningoencephalitis, facial paralysis, confusion, weakness, cognitive dysfunction and other neurological disorders (Araujo et al., 2016). Many of these neurological complications are believed to be due to autoimmune responses to the viral infection which lead to immunological cells of the human body attacking nerves and supporting cells. Mycophenolate is a rather unique antiviral drug in that at high doses it has clinically impressive immunosuppressive properties. It has been discovered that by providing doses of mycophenolic acid that are above the minimum dose required for its antiviral effect but generally below the high doses used clinically for prevention of transplantation rejection, that neurological sequalae of Zika virus infection can be prevented, mitigated. and treated.

Mycophenolic Acid and Neurological Diseases Due to Other Viruses

In addition to Zika, other viruses are well known to have neurological sequellae, including West Nile virus (Morrey et al., 2013), influenza virus (Cardenas et al., 2014, norovirus (Chen et al., 2009), dengue virus (Sil et al., 2017). and other flaviviridae (Soloman et al., 2016). The disclosure provides for the use of mycophenolic acid which can prevent and treat neurological sequalae of other viruses including the above.

Morrey et al., 2013, reviewed mouse and hamster models for neurological sequelae of West Nile virus and showed how the animal models compare to the human neurological sequalae. The mouse model is utilized to demonstrate that administration of mycophenolic acid after infection with West Nile virus prevents and treats a range of neurological diseases and symptoms caused by West Nile virus.

The disclosure provides for the use of mycophenolic acid in preventing and treating neurological sequalae of viral diseases is enhanced by simultaneously administering a low nucleotide diet, and especially a low-guanosine diet. Limiting the availability of guanosine from the diet reduces the body pool of guanosine, thus enhancing the guanosine lowering effect of mycophenolic acid, which is responsible for its antiviral and anti-inflammatory and immunosuppressive properties.

In addition. the disclosure provides a method of preventing and/or treating postviral neurological syndromes in a patient, the method comprising the steps of: selecting a patient in need of preventing and/or treating postviral neurological syndrome; administering to the patient at least one agent selected from the group consisting of minocycline, doxycycline, tetracycline, tetracycline derivatives, L-DOPA, dopamine, and combinations thereof; wherein the postvirasl neurological syndrome is prevented and/or treated in the patient. The disclosure provides a method wherein the postviral neurological syndromes is as a result of infection by a virus selected from the group consisting of Zika virus, Norovirus. Respiratory Syncytial Virus. Influenza. Adenovirus 5, HPV 11. Lassa Fever virus, Powassan virus, Rift Valley virus, and combinations thereof. The disclosure provides a method wherein at least one agent is administered in topical form.

Araujo, A. Q., Silva, M. T., Araujo, A. P. (2016). Zika virus-associated neurological disorders: a review. Brain 139: 2122-2130. Cárdenas, G., Soto-Hernández, J. L., Díaz-Alba, A., Ugalde, Y., Mérida-Puga, J., Rosetti, M., Sciutto. E. (2014). Neurological events related to influenza A (H1N1) pdm09. Influenza Other Respir Viruses 8: 339-346. Chen, S. Y., Tsai, C. N., Lai, M. W., Chen, C. Y., Lin, K. L., Lin. T. Y., Chiu, C. H. (2009). Norovirus infection as a cause of diarrhea-associated benign infantile seizures. Clin Infect Dis 48: 849-855. Morrey, J. D., Siddharthan, V., Wang, H. (2013). Neurological approaches for investigating West Nile virus disease and its treatment in rodents. Antiviral Res 100: 535-545. Sil, A., Biswas, T., Samanta, M., Konar, M. C., De, A. K., Chaudhuri, J. (2017). Neurological manifestations in children with dengue fever: an Indian perspective. Trop Doct 47: 145-149. Soloman T. (2016). Flavivirus encephalitis and other neurological syndromes (Japanese encephalitis. WNV. Tick borne encephalitis, Dengue, Zika virus. International Journal of Infectious Diseases 45S: -24.

Packaging/Treatment Kits

The present disclosure relates to a kit for conveniently and effectively carrying out the methods in accordance with the present disclosure. Such kits may be suited for the delivery of solid oral forms such as tablets or capsules. Such a kit may include a number of unit dosages. Such kits can include a means for containing the dosages oriented in the order of their intended use. An example of a means for containing the dosages in the order of their intended uses is a card. An example of such a kit is a "blister pack". Blister packs are well known in the packaging industry and are widely used for packaging pharmaceutical unit dosage forms. If desired, the blister can be in the form of a childproof blister, i.e., a blister that is difficult for a child to open, yet can be readily opened by an adult. If desired, a memory aid can be provided, for example in the form of numbers, letters, or other markings or with a calendar feature and/or calendar insert, designating the days and the sections of a day in the treatment schedule in which the dosages can be administered, such as an AM dose is packaged with a "mid day" and a PM dose.; or an AM dose is packaged with a PM dose. Alternatively, placebo dosages, or vitamin or dietary supplements, either in a form similar to or distinct from the pharmaceutical active dosages, can be included.

Blister packs. clamshells or trays are forms of packaging used for goods; thus, the disclosure provides for blister packs, clamshells or trays comprising a composition (e.g., a (the multi-ingredient combination of drugs of the disclosure) combination of active ingredients) of the disclosure. Blister packs, clamshells or trays can be designed to be non-reclosable, so consumers can tell if a package has already opened. They are used to package for sale goods where product tampering is a consideration, such as the pharmaceuticals of the disclosure. In one aspect, a blister pack of the disclosure comprises a moulded PVC base, with raised areas (the "blisters") to contain the tablets, pills, etc. comprising the combinations of the disclosure, covered by a foil laminate. Tablets, pills, etc. are removed from the pack either by peeling the foil back or by pushing the blister to force the tablet to break the foil. In one aspect, a specialized form of a blister pack is a strip pack.

In one aspect, a blister pack also comprises a method of packaging where the compositions comprising combinations of ingredients of the disclosure are contained in-between a card and a clear PVC. The PVC can be transparent so the item (pill, tablet, geltab, etc.) can be seen and examined easily; and in one aspect, can be vacuum-formed around a mould so it can contain the item snugly and have room to be opened upon purchase. In one aspect, the card is brightly colored and designed depending on the item (pill, tablet. geltab, etc.) inside, and the PVC is affixed to the card using pre-formed tabs where the adhesive is placed. The adhesive can be strong enough so that the pack may hang on a peg, but weak enough so that this way one can tear open the join and access the item. Sometimes with large items or multiple enclosed pills, tablets, geltabs, etc., the card has a perforated window for access. In one aspect, more secure blister packs, e.g., for items such as pills, tablets, geltabs, etc. of the disclosure are used, and they can comprise of two vacuum-formed PVC sheets meshed together at the edges, with the informative card inside.

In one aspect, blister packaging comprises at least two components (e.g., is a multi-ingredient combination of drugs of the disclosure): a thermoformed "blister" which houses the product (e.g., a pharmaceutical combination of the disclosure), and then a "blister card" that is a printed card with an adhesive coating on the front surface. During the assembly process, the blister component. which is most commonly made out of PVC, is attached to the blister card using a blister machine. This machine introduces heat to the flange area of the blister which activates the glue on the card in that specific area and ultimately secures the PVG blister to the printed blister card. The thermoformed PVG blister and the printed blister card can be as small or large.

As discussed herein, the products of manufacture of the disclosure can comprise the packaging of the therapeutic drug combinations of the disclosure, alone or in combination, as "blister packages" or as a plurality of packettes, including as lidded blister packages, lidded blister or blister card or packets, or a shrink wrap.

Other means for containing said unit dosages can include bottles and vials, wherein the bottle or vial comprises a memory aid, such as a printed label for administering said unit dosage or dosages. The label can also contain removable reminder stickers for placement on a calendar or dayminder to further help the patient to remember when to take a dosage or when a dosage has been taken.

Topical Formulations

The term "topical" as employed herein relates to the use of a compound, derivative or analogue as described herein, incorporated in a suitable pharmaceutical carrier, and applied at the site for exertion of local action. Accordingly, such topical compositions including those forms in which the compound is applied externally by direct contact with the skin surface to be treated. Conventional forms for this purpose include ointments, liniments, creams, shampoos. lotions, pastes, jellies, sprays. aerosols, soaps. and the like, and may be applied in patches or impregnated dressings depending on the part of the body to be treated. The term "ointment" embraces formulations (including creams) having oleaginous, absorption. water-soluble and emulsion-type bases, e.g., petrolatum, lanolin, polyethylene glycols, as well as mixtures of these.

For topical use, the agent of the disclosure can be advantageously formulated using ointments, creams, liniments or patches as a carrier of the active ingredients. Also, these formulations may or may not contain preservatives, depending on the dispenser and nature of use. Such preservatives include those mentioned above, and methyl-, propyl-, or butyl-parahydroxybenzoic acid, betain, chlorhexidine, benzalkonium chloride, and the like. Various matrices for slow release delivery may also be used. Typically, the dose to be applied is in the range of about 0.1 ng to about 100 mg per day, or about 1 ng to about 10 mg per day, or about 10 ng to about 1 mg per day depending on the formulation. Non-limiting examples of topical products can include, without limitation, application stick, mascara, eyebrow coloring products, eye shadow or other eye lid coloring products, eyeliner, make-up removal products. antiaging products, facial or body powder, nail polish, mousse, sprays, styling gels, nail conditioner, bath and shower gels, shampoos, conditioners, cream rinses, hair dyes and coloring products, hair conditioners, sun tanning lotions and creams and sprays, sunscreens and sunblocks, skin conditioners, cold creams, moisturizers, hair sprays, soaps. body scrubs, exfoliants, astringents. depilatories and permanent waving solutions. antidandruff formulations, antisweat and antiperspirant compositions, shaving, preshaving and after shaving products, moisturizers, deodorants, cold creams, cleansers, skin gels, and rinses.

Furthermore, the topical product can be applied topically through the use of a patch or other delivery device. Delivery devices can include, but are not limited to, those that can be heated or cooled, as well as those that utilize iontophoresis or ultrasound.

For instance, the topical product can be applied, for example, by applying a composition in the form of a skin lotion, clear lotion, milky lotion, cream, gel, foam, ointment, paste, emulsion, spray, conditioner, tonic, cosmetic, application stick, pencil, foundation, nail polish, after-shave, or the like which is intended to be left on the skin or other keratinous tissue (i.e., a "leave-on" composition). After applying the composition to the keratinous tissue (e.g., skin), it in one embodiment, it is left on for a period of at least about 15 minutes, or at least about 30 minutes, or at least about 1 hour, or for at least several hours, e.g., up to about 12 hours. In one embodiment, the topical product is left on overnight. In another embodiment, the topical product is left on all day. Any part of the external portion of the face, hair, and/or nails can be treated, (e.g., face, lips, under-eye area, eyelids, scalp, neck, torso, arms, legs, chest, hands, legs, feet, fingernails, toenails, scalp hair, eyelashes, eyebrows, etc.).

Any suitable method can be used to apply the topical product, including but not limited to for example using the palms of the hands and/or fingers or a device or implement (e.g., a cotton ball, swab, pad, applicator pen, spray applicator, eyebrow brush, eyebrow brush pencil, pencil, mascara brush, etc.) Another approach to ensure a continuous exposure of the keratinous tissue to at least a minimum level of the topical product is to apply the compound by use of a patch applied, e.g., to the face. The patch can be occlusive, semi-occlusive or non-occlusive, and can be adhesive or non-adhesive. The topical product can be contained within the patch or be applied to the skin prior to application of the patch. The patch can also include additional actives such as chemical initiators for exothermic reactions. The patch can be left on for any suitable period of time. For example, a period of at least about 5 minutes, or at least about 15 minutes, or at least about 30 minutes. or at least about 1 hour, or at night as a form of night therapy. or in another embodiment all day.

Administration

The pharmaceutical compositions may be optimized for particular types of delivery. For example, pharmaceutical compositions for oral delivery are formulated using pharmaceutically acceptable carriers that are well known in the art. The carriers enable the agents in the composition to be formulated, for example, as a tablet. pill, capsule, solution, suspension, sustained release formulation; powder. liquid or gel for oral ingestion by the subject.

The liquid or solid compositions may contain suitable pharmaceutically acceptable excipients as set out above. Preferably the compositions are administered by the oral, intranasal or respiratory route for local or systemic effect. Compositions in preferably sterile pharmaceutically acceptable solvents may be nebulized by use of inert gases. Nebulized solutions may be breathed directly from the nebulizing device or the nebulizing device may be attached to a face mask, tent or intermittent positive pressure breathing machine. Solution, suspension or powder compositions may be administered, preferably orally or nasally. from devices that deliver the formulation in an appropriate manner.

Typically. the composition may be applied repeatedly for a sustained period of time topically on the part of the body to be treated, for example, the eyelids, eyebrows. skin or scalp. The dosage regimen will generally involve regular, such as daily, administration for a period of treatment of at least one month, or at least three months, or at least six months.

Alternatively, the composition may be applied intermittently, or in a pulsed manner. Accordingly. an alternative embodiment of the disclosure is to apply the composition on an intermittent or pulsed dosage schedule. For example, the composition of the disclosure may be used for two or more days, stopped, then restarted again at a time from between 2 weeks to 3 months later, and at even more long-spaced intervals in the case of the scalp.

The treatments may include various "unit doses." Unit dose is defined as containing a predetermined-quantity of the therapeutic composition. The quantity to be administered, and the particular route and formulation, are within the skill of those in the clinical arts. A unit dose need not be administered as a single injection but may comprise continuous infusion over a set period of time. Alternatively, the amount specified may be the amount administered as the average daily, average weekly. or average monthly dose.

The disclosure will be illustrated in more detail with reference to the following Examples, but it should be understood that the present disclosure is not deemed to be limited thereto.

EXAMPLES

Example 1

Prevention and Treatment of a Male at Risk for Zika Infection

In this example, the new method prevents or minimizes infection of humans by Zika virus. Here, a male at risk for being stung by an *Aedes* mosquito takes the following steps. He starts taking daily low dose oral mycophenolate one week before he travels to a Zika infested area and continues taking it while in the area. He applies a melanin containing lotion daily to skin not covered by clothing.

The use of these methods inhibits the infection in the following ways.

1. The lotion containing melanin is applied to the skin and is partially absorbed into the epidermis and dermis. It rapidly evaporates to leave a thin tough film. The external film of melanin minimizes or entirely prevents the entry of the virus in the skin from the stinger of the *Aedes* mosquito vector. If any virus is successfully injected into the epidermis or dermis, the absorbed melanin, which is toxic to the virus but not to human cells, eliminates or reduces the amount of live virus which has been introduced.

2. It has been demonstrated that three types of cells in the skin are normally susceptible to infection by the Zika virus: epidermal keratinocytes, dermal fibroblasts, and (dermal) macrophages. It has also been demonstrated that mycophenolate dramatically reduces guanosine levels in all three cell types. Thus because of relative depletion of guanosine in these cells, there is reduced (or absent) replication of the viral RNA in these cells as the guanosine necessary for replication of RNA is in short supply. Thus viral particles injected are only able to reproduce at a lower amount, or not at all, minimizing or terminating the infective load.

3. If in spite of the prior steps, the virus is successful in penetrating to the blood stream and causing a viremia, the systemic mycophenolate directly inhibits the replication of the Zika virus in the blood and throughout the body.

4. Note that since a very small amount of antigen is known to trigger the immune system responses, it is likely that even if the injected viral load is partially destroyed and the ability of remaining virus particles to replicate is limited, there is likely to be adequate viral antigen to stimulate the normal antiviral responses of the innate and adaptive immune systems.

Example 2

Prevention and Treatment of a Female at Risk for Pregnancy and Zika Infection.

Here, a female who is sexually active and may become pregnant is at risk for being stung by an *Aedes* mosquito and takes the following steps. She starts on a reduced guanosine diet designed for women who are pregnant or may become pregnant, one week before she travels to a Zika infested area and continues adhering to this diet while in the area. She applies a melanin containing lotion daily to skin not covered by clothing.

1. The lotion containing melanin is applied to the skin and is partially absorbed into the epidermis and dermis. It rapidly evaporates to leave a thin tough film. The external film of melanin minimizes or entirely prevents the entry of the virus in the skin from the stinger of the *Aedes* mosquito vector. If any virus is successfully injected into the epidermis or dermis, the absorbed melanin, which is toxic to the virus but not to human cells, eliminates or reduces the amount of live virus which has been introduced.

2. It has been demonstrated that three types of cells in the skin are normally susceptible to infection by the Zika virus: epidermal keratinocytes, dermal fibroblasts, and (dermal) macrophages. The reduced guanosine diet reduces guanosine levels in all three cell types. Thus because of relative depletion of guanosine in these cells, there is reduced (or absent) replication of the viral RNA in these cells as the guanosine necessary for replication of RNA is in short supply. Thus viral particles injected are only able to reproduce at a lower amount, or not at all, minimizing or terminating the infective load.

3. If in spite of the prior steps, the virus is successful in penetrating to the blood stream and causing a viremia, the relative lack of guanosine caused by the reduced diet limits the ability of the virus to replicate.

4. The above steps are successful in interdicting the infection sufficiently that an embryo or fetus is not damaged by the maternal viral infection.

Example 3

Treatment of a Patient with Multi-Drug Resistant Tuberculosis.

A traveler from the US contracts multi-drug resistant tuberculosis while in India. There are no known effective antibiotics. The patient is administered 3 ounces (about 90 gm) of cuttlefish ink (which contains melanin) mixed in his regular food twice per day for two weeks. Then mycophenolate mofetil 250 mg twice per day is added. The regimen is continued for 3 months leading to cure of the multidrug-resistant tuberculosis.

Example 4

Treatment of a Patient with Infectious Pulmonary Aspergillosis.

As asthma patient contracts infectious pulmonary aspergillosis, a fungal disease. The patient is administered 2 grams of melanin (1 gm/capsule) mixed in his regular food twice per day for two weeks. Then mycophenolate mofetil 250 mg twice per day is added. The regimen is continued for 3 months leading to cure of the aspergillosis.

Example 5

Diets with Reduced Guanosine Content

These invented diets are low in nucleic acids and their components but are not nucleotide-free. The diets contain approximately 3% to 50% of the amount by weight of nucleotides seen in the normal western diet (2000 mg/day, from Ekelman, K. Disodium 5'Guanylate and Disodium 5'-Inosate. *WHO Food Additives Series, No.* 32 (1993), and preferably 10%-40%.

The inventor has conducted extensive analysis of the nucleotide content of human foods from a variety of sources, and evaluated the nutritional content and palatability of potential nucleotide-free diets. The inventor has concluded that it is not practical for most people to stay on a nucleotide-free diet in a compliant manner for the period of months required to obtain substantial clinical benefit from this approach. A nucleotide-free diet is unlikely to be sufficiently palatable for extended use and would deter compliance. Also, use of a nucleotide-free diet for months in humans would likely lead to other dietary deficiencies.

As set forth above, the disclosure provides treatment of a patient with a diet which contains approximately 3% to 50% of the amount by weight of nucleotides seen in the normal western diet, which contains about 2000 mg/day of nucleotides. In exemplary embodiments, the diet of the disclosure contains a nucleotide content of about 1000 mg/day, of about 750 mg/day, of about 500 mg/day, of about 250 mg/day, of about 100 mg/day, of about 75 mg/day, of about 50 mg/day, of about 25 mg/day. In exemplary embodiments, the diet of the disclosure contains a nucleotide content compared to the normal Western diet of about 50%, of about 40%, of about 30%, of about 20%, of about 10%, of about 5%, of about 3%. In exemplary embodiments, the diet of the disclosure contains a nucleotide content compared to the normal Western diet of 3-50%, of about 10-40%, of about 20-30%, of about 3-40%, of about 3-30%, of about 10-30%, of about 10-20%.

Example 6

Diets with Reduced Guanosine Content Optimized for Women Who are Pregnant or May Become Pregnant.

The diets in Example 5 are modified to make them appropriate for women who are pregnant. The modified diets contain additional calcium, trace minerals, and B vitamin supplements. A supplement like Ensure or Boost would be added to the diet. There would be additional fatty acids and protein.

Example 7

In Vitro Demonstration of Method Efficacy

Using methods similar to those of Diamond et al, 2002, (Diamond, M., Zachariah, M, and Harris, E. "Mycophenolic Acid Inhibits Dengue Virus Infection by Preventing Replication of Viral RNA." *Virology* 304, no. 2 (2002): 211-221) mycophenolate and melanin are shown together, or when administered sequentially, to inhibit the replication of the Zika virus in vitro. For example, Zika virus is added to monolayers of hepatoma cells or hamster kidney cells at several different doses. They are incubated for 2 hours at a temperature of 37 C. The cells are washed several times. Mycophenolate or melanin or both are added to the cells after they are exposed to Zika. After 72 hours the cells are harvested. RNA, viral antigen, and virion are quantitated. The results show that mycophenolate and melanin together inhibit almost all replication of the Zika virus. Depending on the type of cells used, the dose of Zika virus, the doses of mycophenolate and/or melanin, the viral replication is inhibited in various degrees.

Example 8

Zika

Three in vitro tests showed MPA to be active against Zika Virus. The primary screening test (Zika-A) was carried out in monkey Vero cells. The two secondary screening tests were carried out against monkey Vero cells (Zika-B) and human cells (Zika-C).

| | | | | | | | |
|---|---|---|---|---|---|---|---|
| Virus Screened: | | | Zika Virus | | | | |
| Virus Strain: | | | MR766 | | | | |
| Cell Line: | | | Vero 76 | | | | |
| Vehicle: | | | DMSO | | | | |
| Drug Conc. Range: | | | 0.1-100 µg/ml | | | | |
| Control Conc. Range: | | | 0.1-100 µg/ml | | | | |
| Experiment Number: | | | Zika-089 | | | | |

| Control Drug Name | Control Assay Order | Control Assay Name | $EC_{50}$ | $EC_{90}$ | $CC_{50}$ | $SI_{50}$ | $SI_{90}$ |
|---|---|---|---|---|---|---|---|
| 6-Azauridine | Primary | Visual (Cytopathic effect/Toxicity) | 0.32 | | >100 | >310 | |
| 6-Azauridine | Primary | Neutral Red (Cytopathic effect/Toxicity) | 0.35 | | 83.3 | 238 | |

| ARB No. | Date Received m/dd/yy | Compound Name/ID | Drug Assay Order | Drug Assay Name | $EC_{50}$ | $EC_{90}$ | $CC_{50}$ | $SI_{50}$ | $SI_{90}$ |
|---|---|---|---|---|---|---|---|---|---|
| 16-000406 | Jun. 18, 2016 | EP1601 | Primary | Visual (Cytopathic effect/Toxicity) | <0.1 | | >100 | >1000 | |
| 16-000406 | Jun. 18, 2016 | EP1601 | Primary | Neutral Red (Cytopathic effect/Toxicity) | 0.15 | | 14 | 93 | |

| | | | | | | | |
|---|---|---|---|---|---|---|---|
| Virus Screened: | | | Zika virus | | | | |
| Virus Strain: | | | MR766 | | | | |
| Cell Line: | | | Vero 76 | | | | |
| Vehicle: | | | DMSO | | | | |
| Drug Conc. Range: | | | 0.1-100 µg/ml | | | | |
| Control Conc. Range: | | | 0.1-100 µg/ml | | | | |
| Experiment Number: | | | Zika-094 | | | | |

| Control Drug Name | Control Assay Order | Control Assay Name | $EC_{50}$ | $EC_{90}$ | $CC_{50}$ | $SI_{50}$ | $SI_{90}$ |
|---|---|---|---|---|---|---|---|
| 6-Azauridine | Secondary | Visual (Virus yield reduction)/Neutral Red (Toxicity) | | 1.3 | 9.9 | | 7.6 |
| 6-Azauridine | Secondary | Neutral Red (Cytopathic effect/Toxicity) | 0.37 | | 9.9 | 27 | |

| ARB No. | Date Received m/dd/yy | Compound Name/ID | Drug Assay Order | Drug Assay Name | $EC_{50}$ | $EC_{90}$ | $CC_{50}$ | $SI_{50}$ | $SI_{90}$ |
|---|---|---|---|---|---|---|---|---|---|
| 16-000406 | Jul. 8, 2016 | EP1601 | Secondary | Visual (Virus yield reduction)/Neutral Red (Toxicity) | | 0.3 | 2.3 | | 7.7 |

-continued

| ARB No. | Date Received m/dd/yy | Compound Name/ID | Drug Assay Order | Drug Assay Name | EC$_{50}$ | EC$_{90}$ | CC$_{50}$ | SI$_{50}$ | SI$_{90}$ |
|---|---|---|---|---|---|---|---|---|---|
| 16-000406 | Jul. 8, 2016 | EP1601 | Secondary | Neutral Red (Cytopathic effect/Toxicity) | 0.14 | | 2.3 | 16 | |

| | | | | |
|---|---|---|---|---|
| | Virus Screened: | | Zika virus | |
| | Virus Strain: | | MR766 | |
| | Cell Line: | | Huh7 | |
| | Vehicle: | | DMSO | |
| | Drug Conc. Range: | | 0.1-100 μg/ml | |
| | Control Conc. Range: | | 0.1-100 μg/ml | |
| | Experiment Number: | | Zika-094 | |

| Control Drug Name | Control Assay Order | Control Assay Name | EC$_{50}$ | EC$_{90}$ | CC$_{50}$ | SI$_{50}$ | SI$_{90}$ |
|---|---|---|---|---|---|---|---|
| 6-Azauridine | Secondary | Visual (Virus yield reduction)/Neutral Red (Toxicity) | | 27.4 | >100 | | >3.6 |
| 6-Azauridine | Secondary | Neutral Red (Cytopathic effect/Toxicity) | 1.2 | | >100 | >83 | |

| ARB No. | Date Received m/dd/yy | Compound Name/ID | Drug Assay Order | Drug Assay Name | EC$_{50}$ | EC$_{90}$ | CC$_{50}$ | SI$_{50}$ | SI$_{90}$ |
|---|---|---|---|---|---|---|---|---|---|
| 16-000406 | Jul. 9, 2016 | EP1601 | Secondary | Visual (Virus yield reduction)/Neutral Red (Toxicity) | | 0.088 | 1.6 | | 18 |
| 16-000406 | Jul. 9, 2016 | EP1601 | Secondary | Neutral Red (Cytopathic effect/Toxicity) | 0.14 | | 1.6 | 33 | |

Zika Prevention

MPA was pre-incubated with Huh7 cells 4 hours prior to Zika infection.

| | | | | |
|---|---|---|---|---|
| | Virus Screened: | | Zika virus | |
| | Virus Strain: | | MR766 | |
| | Cell Line: | | Huh7 | |
| | Vehicle: | | DMSO | |
| | Drug Conc. Range: | | 0.032-100 μg/ml | |
| | Control Conc. Range: | | 0.032-100 μg/ml | |
| | Experiment Number: | | Zika-138 | |

| Control Drug Name | Control Assay Order | Control Assay Name | EC$_{50}$ | EC$_{90}$ | CC$_{50}$ | SI$_{50}$ | SI$_{90}$ |
|---|---|---|---|---|---|---|---|
| NITD008 | Secondary | Visual (Virus yield reduction)/Neutral Red (Toxicity) | | 0.61 | >100 | | >164 |
| NITD008 | Secondary | Neutral Red (Cytopathic effect/Toxicity) | 1.1 | | >100 | >91 | |

| ARB No. | Date Received m/dd/yy | Compound Name/ID | Drug Assay Order | Drug Assay Name | EC$_{50}$ | EC$_{90}$ | CC$_{50}$ | SI$_{50}$ | SI$_{90}$ |
|---|---|---|---|---|---|---|---|---|---|
| 16-000406 | Nov. 2, 2016 | EP1601 | Secondary | Visual (Virus yield reduction)/Neutral Red (Toxicity) | | 42.71 | >100 | | >2.3 |
| 16-000406 | Nov. 2, 2016 | EP1601 | Secondary | Neutral Red (Cytopathic effect/Toxicity) | 0.17 | | >100 | >590 | |

MPA was pre-incubated with Huh7 cells 24 hours prior to Zika infection.

|  |  |  |  |  |  |  |
|---|---|---|---|---|---|---|
| Virus Screened: | | Zika virus | | | | |
| Virus Strain: | | MR766 | | | | |
| Cell Line: | | Huh7 | | | | |
| Vehicle: | | DMSO | | | | |
| Drug Conc. Range: | | 0.032-100 µg/ml | | | | |
| Control Conc. Range: | | 0.032-100 µg/ml | | | | |
| Experiment Number: | | Zika-138 | | | | |

| Control Drug Name | Control Assay Order | Control Assay Name | $EC_{50}$ | $EC_{90}$ | $CC_{50}$ | $SI_{50}$ | $SI_{90}$ |
|---|---|---|---|---|---|---|---|
| NITD008 | Secondary | Visual (Virus yield reduction)/Neutral Red (Toxicity) | | 1.0 | 27 | | 27 |
| NITD008 | Secondary | Neutral Red (Cytopathic effect/Toxicity) | 0.77 | | 27 | 34 | |

| ARB No. | Date Received m/dd/yy | Compound Name/ID | Drug Assay Order | Drug Assay Name | $EC_{50}$ | $EC_{90}$ | $CC_{50}$ | $SI_{50}$ | $SI_{90}$ |
|---|---|---|---|---|---|---|---|---|---|
| 16-000406 | Jun. 18, 2016 | EP1601 | Secondary | Visual (Virus yield reduction)/Neutral Red (Toxicity) | | 0.78 | 1.4 | | 1.8 |
| 16-000406 | Jun. 18, 2016 | EP1601 | Secondary | Neutral Red (Cytopathic effect/Toxicity) | 0.55 | | 1.4 | 2.5 | |

MPA was pre-incubated with Vero 76 cells 4 hours prior to Zika infection.

|  |  |
|---|---|
| Virus Screened: | Zika virus |
| Virus Strain: | MR766 |
| Cell Line: | Vero 76 |
| Vehicle: | DMSO |
| Drug Conc. Range: | 0.032-100 µg/ml |
| Control Conc. Range: | 0.032-100 µg/ml |
| Experiment Number: | Zika-138 |

| Control Drug Name | Control Assay Order | Control Assay Name | $EC_{50}$ | $EC_{90}$ | $CC_{50}$ | $SI_{50}$ | $SI_{90}$ |
|---|---|---|---|---|---|---|---|
| NITD008 | Secondary | Visual (Virus yield reduction)/Neutral Red (Toxicity) | | 7.81 | >100 | | >12.8 |
| NITD008 | Secondary | Neutral Red (Cytopathic effect/Toxicity) | 8.3 | | >100 | 0 | |

| ARB No. | Date Received m/dd/yy | Compound Name/ID | Drug Assay Order | Drug Assay Name | $EC_{50}$ | $EC_{90}$ | $CC_{50}$ | $SI_{50}$ | $SI_{90}$ |
|---|---|---|---|---|---|---|---|---|---|
| 16-000406 | Nov. 1, 2016 | EP1601 | Secondary | Visual (Virus yield reduction)/Neutral Red (Toxicity) | | 17.8 | >100 | | >5.6 |
| 16-000406 | Nov. 1, 2016 | EP1601 | Secondary | Neutral Red (Cytopathic effect/Toxicity) | >100 | | >100 | 0 | |

MPA was pre-incubated with Vero 76 cells 24 hours prior to Zika infection.

|  |  |
|---|---|
| Virus Screened: | Zika virus |
| Virus Strain: | MR766 |
| Cell Line: | Vero 76 |
| Vehicle: | DMSO |
| Drug Conc. Range: | 0.032-100 µg/ml |
| Control Conc. Range: | 0.032-100 µg/ml |
| Experiment Number: | Zika-138 |

| Control Drug Name | Control Assay Order | Control Assay Name | $EC_{50}$ | $EC_{90}$ | $CC_{50}$ | $SI_{50}$ | $SI_{90}$ |
|---|---|---|---|---|---|---|---|
| NITD008 | Secondary | Visual (Virus yield reduction)/Neutral Red (Toxicity) | | 31.62 | >100 | | >3.2 |
| NITD008 | Secondary | Neutral Red (Cytopathic effect/Toxicity) | 5.1 | | >100 | >20 | |

| ARB No. | Date Received m/dd/yy | Compound Name/ID | Drug Assay Order | Drug Assay Name | $EC_{50}$ | $EC_{90}$ | $CC_{50}$ | $SI_{50}$ | $SI_{90}$ |
|---|---|---|---|---|---|---|---|---|---|
| 16-000406 | Nov. 3, 2016 | EP1601 | Secondary | Visual (Virus yield reduction)/Neutral Red (Toxicity) | | 10 | 37 | | 3.7 |
| 16-000406 | Nov. 3, 2016 | EP1601 | Secondary | Neutral Red (Cytopathic effect/Toxicity) | 8 | | 37 | 4.6 | |

Example 9

Norovirus

Three in vitro tests showed MPA to be active against Norovirus. The primary screening test (NOV-A) was carried out with human norovirus. Additional testing was carried out with mouse norovirus (NOV-B). Secondary testing was done with human norovirus.

| | |
|---|---|
| Virus Screened: | NV |
| Virus Strain: | $GT_1$ |
| Cell Line: | $HG_{23}$ |
| Vehicle: | DMSO |
| Drug Conc. Range: | 0.05-100 uM |
| Control Conc. Range: | 3.7-100 uM |
| Experiment Number: | 16-21 |

| Control Drug Name | Control Assay Order | Control Assay Name | $EC_{50}$ | $EC_{90}$ | $CC_{50}$ | $SI_{50}$ | $SI_{90}$ |
|---|---|---|---|---|---|---|---|
| 2'C-methyl cytidine | primary | RNA Hybridization (Replicon)/RNA Hybridization (Toxicity) | 6.6 | 17 | >300 | >45 | >18 |

| ARB No. | Date Received m/dd/yy | Compound Name/ID | Drug Assay Order | Drug Assay Name | $EC_{50}$ | $EC_{90}$ | $CC_{50}$ | $SI_{50}$ | $SI_{90}$ |
|---|---|---|---|---|---|---|---|---|---|
| 16-000406 | Jul. 19, 2016 | EP1601 | Primary | RNA Hybridization (Replicon)/RNA Hybridization (Toxicity) | 0.151 | 1.3 | >100 | >622 | >77 |

| | |
|---|---|
| Virus Screened: | MNV |
| Virus Strain: | $MNV_{-1}$ |
| Cell Line: | $RAW_{264.7}$ |
| Vehicle: | DMSO |
| Drug Conc. Range: | 0.1-100 uM |
| Control Conc. Range: | 1.1-30 uM |
| Experiment Number: | 17-09 |

| Control Drug Name | Control Assay Order | Control Assay Name | $EC_{50}$ | $EC_{90}$ | $CC_{50}$ | $SI_{50}$ | $SI_{90}$ |
|---|---|---|---|---|---|---|---|
| 2'C-methyl cytidine | primary | NR (CPE)/ NR (Tox) | 1.0 | 3.2 | 51 | 51 | 16 |

-continued

| ARB No. | Date Received m/dd/yy | Trail No. | Compound Name/ID | Drug Assay Order | Drug Assay Name | $EC_{50}$ | $EC_{90}$ | $CC_{50}$ | $SI_{50}$ | $SI_{90}$ |
|---|---|---|---|---|---|---|---|---|---|---|
| 16-000406 | Jul. 19, 2016 | 1 | EP1601 | Primary | NR (CPE)/ NR (Tox) | 0.123 | 0.384 | 32 | 260 | 83 |

|  |  |
|---|---|
| Virus Screened: | NV |
| Virus Strain: | $GT_1$ |
| Cell Line: | $HG_{23}$ |
| Vehicle: | DMSO |
| Drug Conc. Range: | 0.024-100 uM |
| Control Conc. Range: | 3.7-100 uM |
| Experiment Number: | 17-14 |

| Control Drug Name | Control Assay Order | Control Assay Name | $EC_{50}$ | $EC_{90}$ | $CC_{50}$ | $SI_{50}$ | $SI_{90}$ |
|---|---|---|---|---|---|---|---|
| 2'C-methyl cytidine | secondary | qPCR (Replicon)/ NR (Tox) | 6.0 | 18 | >300 | >50 | >17 |

| ARB No. | Date Received m/dd/yy | Compound Name/ID | Drug Assay Order | Drug Assay Name | $EC_{50}$ | $EC_{90}$ | $CC_{50}$ | $SI_{50}$ | $SI_{90}$ |
|---|---|---|---|---|---|---|---|---|---|
| 16-000406 | Jul. 19, 2016 | EP1601 | Primary | qPCR (Replicon)/ NR (Tox) | 0.219 | 1.1 | 64 | 292 | 58 |

Example 10

Pandemic Influenza Flu

MPA was highly active against pandemic Influenza A H1N1 (California/07/2009).

|  |  |
|---|---|
| Virus Screened: | Influenza A virus $H_1N_1$ |
| Virus Strain: | California/07/2009 |
| Cell Line: | MDCK |
| Vehicle: | DMSO |
| Drug Conc. Range: | 0.1-100 μM |
| Control Conc. Range: | 0.32-320 μM |
| Experiment Number: | FLU-1195 |

| Control Drug Name | Control Assay Order | Control Assay Name | $EC_{50}$ | $EC_{90}$ | $CC_{50}$ | $SI_{50}$ | $SI_{90}$ |
|---|---|---|---|---|---|---|---|
| Ribavirin | Primary | Visual (Cytopathic effect/Toxicity) | 3.7 |  | >320 | >86 |  |
| Ribavirin | Primary | Neutral Red (Cytopathic effect/Toxicity) | 4.1 |  | >320 | >78 |  |

| ARB No. | Date Received m/dd/yy | Compound Name/ID | Drug Assay Order | Drug Assay Name | $EC_{50}$ | $EC_{90}$ | $CC_{50}$ | $SI_{50}$ | $SI_{90}$ |
|---|---|---|---|---|---|---|---|---|---|
| 16-000406 | Mar. 1, 2017 | EP1601 | Primary | Visual (Cytopathic effect/Toxicity) | <0.1 |  | >100 | >1000 |  |
| 16-000406 | Mar. 1, 2017 | EP1601 | Primary | Neutral Red (Cytopathic effect/Toxicity) | <0.1 |  | >100 | >1000 |  |

Example 11

Respiratory Syncytial Virus

MPA was highly active against Respiratory Syncytial Virus

|  |  |
|---|---|
| Virus Screened: | Respiratory syncytial virus |
| Virus Strain: | $A_2$ |
| Cell Line: | $MA_{-104}$ |
| Vehicle: | DMSO |
| Drug Conc. Range: | 0.1-100 μg/ml |

|  | Control Conc. Range:<br>Experiment Number: |  |  | 0.32-320 µg/ml<br>$RSV_{-0268}$ |  |  |  |  |
|---|---|---|---|---|---|---|---|---|

| Control Drug Name | Control Assay Order | Control Assay Name | $EC_{50}$ | $EC_{90}$ | $CC_{50}$ | $SI_{50}$ | $SI_{90}$ |
|---|---|---|---|---|---|---|---|
| Ribavirin | Primary | Visual (Cytopathic effect/Toxicity) | 7.6 |  | >320 | >42 |  |
| Ribavirin | Primary | Neutral Red (Cytopathic effect/Toxicity) | 12 |  | >320 | >27 |  |

| ARB No. | Date Received m/dd/yy | Compound Name/ID | Drug Assay Order | Drug Assay Name | $EC_{50}$ | $EC_{90}$ | $CC_{50}$ | $SI_{50}$ | $SI_{90}$ |
|---|---|---|---|---|---|---|---|---|---|
| 16-000406 | Mar. 1, 2017 | EP1601 | Primary | Visual (Cytopathic effect/Toxicity) | <0.1 |  | >100 | >1000 |  |
| 16-000406 | Mar. 1, 2017 | EP1601 | Primary | Neutral Red (Cytopathic effect/Toxicity) | <0.1 |  | >100 | >1000 |  |

Example 12

Others

Additionally, MPA was active against the following viruses:

Adenovirus 5, HPV 11, Lassa Fever, Powassan, Rift Valley.

|  |  |  |  |
|---|---|---|---|
| Virus Screened: | $Adenovirus_5$ |
| Virus Strain: | $Adenoid_{75}$ |
| Cell Line: | $A_{549}$ |
| Vehicle: | DMSO |
| Drug Conc. Range: | 0.1-100 µg/ml |
| Control Conc. Range: | 0.1-100 µg/ml |
| Experiment Number: | $ADV_{-0172}$ |

| Control Drug Name | Control Assay Order | Control Assay Name | $EC_{50}$ | $EC_{90}$ | $CC_{50}$ | $SI_{50}$ | $SI_{90}$ |
|---|---|---|---|---|---|---|---|
| 2,3-Dideoxy-cytidine | Primary | Visual (Cytopathic effect/Toxicity) | 3.2 |  | >100 | >31 |  |
| 2,3-Dideoxy-cytidine | Primary | Neutral Red (Cytopathic effect/Toxicity) | 3.2 |  | >100 | >31 |  |

| ARB No. | Date Received m/dd/yy | Compound Name/ID | Drug Assay Order | Drug Assay Name | $EC_{50}$ | $EC_{90}$ | $CC_{50}$ | $SI_{50}$ | $SI_{90}$ |
|---|---|---|---|---|---|---|---|---|---|
| 16-000406 | Jul. 15, 2016 | EP1601 | Primary | Visual (Cytopathic effect/Toxicity) | 0.32 |  | 15 | 47 |  |
| 16-000406 | Jul. 15, 2016 | EP1601 | Primary | Neutral Red (Cytopathic effect/Toxicity) | 0.31 |  | 12 | 39 |  |

|  |  |
|---|---|
| Virus Screened: | Human $papillomavirus_{11}$ |
| Virus Strain: | $RRP_{33715}LTR$ |
| Cell Line: | $C_{-33}A$ |
| Vehicle: | DMSO |
| Drug Conc. Range: | 0.048-150 µM |
| Control Conc. Range: | 0.048-150 µM |
| Experiment Number: | $HPV_{16-15}$ |

| Control Drug Name | Control Assay Order | Control Assay Name | $EC_{50}$ | $EC_{90}$ | $CC_{50}$ | $SI_{50}$ | $SI_{90}$ |
|---|---|---|---|---|---|---|---|
| 9-[2-(phosphono-methoxy)ethyl]guanine | Primary | Nano-Glo Luciferase (NanoLuc)/Cell Titer-Glo (Toxicity) | 7.27 | 25.21 | 140.59 | 19 | 6 |

| ARB No. | Date Received m/dd/yy | Compound Name/ID | Drug Assay Order | Drug Assay Name | EC$_{50}$ | EC$_{90}$ | CC$_{50}$ | SI$_{50}$ | SI$_{90}$ |
|---|---|---|---|---|---|---|---|---|---|
| 16-000406 | Jul. 15, 2016 | EP1601 | Primary | Nano-Glo Luciferase (NanoLuc)/Cell Titer-Glo (Toxicity) | 0.79 | 3.67 | >150 | >191 | >41 |

| | | | |
|---|---|---|---|
| Virus Screened: | | Lassa fever virus | |
| Virus Strain: | | Josiah | |
| Cell Line: | | Vero | |
| Vehicle: | | DMSO | |
| Drug Conc. Range: | | 0.1-100 µg/ml | |
| Control Conc. Range: | | 0.1-100 µM | |
| Experiment Number: | | LASV$_{-015}$ | |

| Control Drug Name | Control Assay Order | Control Assay Name | EC$_{50}$ | EC$_{90}$ | CC$_{50}$ | SI$_{50}$ | SI$_{90}$ |
|---|---|---|---|---|---|---|---|
| Ribavirin | Primary | Crystal violet (Plaque reduction)/ Neutral red (Toxicity) | 32 | | >100 | >3.1 | |

| ARB No. | Date Received m/dd/yy | Compound Name/ID | Drug Assay Order | Drug Assay Name | EC$_{50}$ | EC$_{90}$ | CC$_{50}$ | SI$_{50}$ | SI$_{90}$ |
|---|---|---|---|---|---|---|---|---|---|
| 16-000406 | Jul. 15, 2016 | EP1601 | Primary | Crystal violet (Plaque reduction)/ Neutral red (Toxicity) | 0.2 | | >100 | >500 | |

| | | | |
|---|---|---|---|
| Virus Screened: | | Powassan virus | |
| Virus Strain: | | LB | |
| Cell Line: | | BHK | |
| Vehicle: | | DMSO | |
| Drug Conc. Range: | | 0.1-100 µg/ml | |
| Control Conc. Range: | | 0.00001-0.01 µg/ml | |
| Experiment Number: | | POW$_{-055}$ | |

| Control Drug Name | Control Assay Order | Control Assay Name | EC$_{50}$ | EC$_{90}$ | CC$_{50}$ | SI$_{50}$ | SI$_{90}$ |
|---|---|---|---|---|---|---|---|
| Infergen | Primary | Visual (Cytopathic effect/Toxicity) | 0.00032 | | >0.01 | >31 | |
| Infergen | Primary | Neutral Red (Cytopathic effect/Toxicity) | 0.00026 | | >0.01 | >38 | |

| ARB No. | Date Received m/dd/yy | Compound Name/ID | Drug Assay Order | Drug Assay Name | EC$_{50}$ | EC$_{90}$ | CC$_{50}$ | SI$_{50}$ | SI$_{90}$ |
|---|---|---|---|---|---|---|---|---|---|
| 16-000406 | Jul. 15, 2016 | EP1601 | Primary | Visual (Cytopathic effect/Toxicity) | 0.32 | 3.2 | 10 | | |
| 16-000406 | Jul. 15, 2016 | EP1601 | Primary | Neutral Red (Cytopathic effect/Toxicity) | 0.36 | 1.1 | 3.1 | | |

| | | | |
|---|---|---|---|
| Virus Screened: | | Rift Valley fever virus | |
| Virus Strain: | | MP$_{-12}$ | |
| Cell Line: | | Vero$_{76}$ | |
| Vehicle: | | DMSO | |
| Drug Conc. Range: | | 0.1-100 µg/ml | |
| Control Conc. Range: | | 1-1000 µg/ml | |
| Experiment Number: | | RVFV$_{-154}$ | |

| Control Drug Name | Control Assay Order | Control Assay Name | EC$_{50}$ | EC$_{90}$ | CC$_{50}$ | SI$_{50}$ | SI$_{90}$ |
|---|---|---|---|---|---|---|---|
| Ribavirin | Primary | Visual (Cytopathic effect/Toxicity) | 11 | | >1000 | >91 | |
| Ribavirin | Primary | Neutral Red (Cytopathic effect/Toxicity) | 12 | | 1000 | >83 | |

-continued

| ARB No. | Date Received m/dd/yy | Compound Name/ID | Drug Assay Order | Drug Assay Name | $EC_{50}$ | $EC_{90}$ | $CC_{50}$ | $SI_{50}$ | $SI_{90}$ |
|---|---|---|---|---|---|---|---|---|---|
| 16-000406 | Jul. 15, 2016 | EP1601 | Primary | Visual (Cytopathic effect/Toxicity) | 3.1 | | 26 | 8.4 | |
| 16-000406 | Jul. 15, 2016 | EP1601 | Primary | Neutral Red (Cytopathic effect/Toxicity) | 4 | | 17 | 4.3 | |

Example 13

Below are the Day 7 and 33 results for the test panel in Cuttlefish Ink (Nortindal Sea Products lot N-L:IR:14/14B.B). The material showed good across the board reduction of the microbial challenge panel used. The panel includes representatives of common Gram negative and Gram positive pathogens and opportunistic pathogens, mold and yeast. The "Control sample" counts are for the un-spiked product and show it to maintain <10 colony-forming units per gram stored at ambient temperature.

Results; 33-day exposure at 20-25 C: (Counts in colony forming units/g)

| Organism [ATCC #] | $T_0$ | $T_{day\ 7}$ | 7-day % reduction of initial spike |
|---|---|---|---|
| S. aureus [6578] | $1.58 \times 10^3$ | $6.0 \times 10^2$ | 62.0% |
| E. coli [8739] | $2.34 \times 10^3$ | $6.8 \times 10^2$ | 70.9% |
| P. aeruginosa [9027] | $1.48 \times 10^3$ | <10 | 99.4% |
| C. albicans (yeast) [10231] | $4.5 \times 10^2$ | <10 | 98.0% |
| A. brasiliensis (mold) [16404] | $3.3 \times 10^2$ | $1.2 \times 10^2$ | 63.6% |

Control sample: <10

Example 14

Report of Microbiological Testing

| | | | | Cuttlefish ink | | | | |
|---|---|---|---|---|---|---|---|---|
| | | Inoculum | Day 1 | Day 2 | Day 3 | Day 7 | Log Reduction | |
| Staphylocos aureus ATCC 6538 | Mean Count | 1.08E+06 | 1.60E+06 | 1.67E+06 | 1.60E+06 | 5.95E+05 | 0.3 | NA/FIO |
| | % reduction | | -48.14181 | -54.1667 | -47.6852 | 44.9074 | | |
| Eschericia coli ATCC 8739 | Mean Count | 1.20E+06 | 7.80E+05 | 3.05E+05 | 1.94E+05 | 1.97E+04 | 1.8 | NA/FIO |
| | % reduction | | 34.7280 | 74.4770 | 83.8075 | 98.3556 | | |
| Pseudomonas aeruginosa ATCC 9027 | Mean Count | 1.08E+06 | 6.50E+05 | 1.13E+05 | 3.05E+04 | 3.10E+03 | 2.5 | NA/FIO |
| | % reduction | | 39.5349 | 89.5349 | 96.7442 | 99.7116 | | |
| Candida albicans ATCC 10231 | Mean Count | 5.05E+05 | 6.45E+05 | 3.85E+05 | 1.68E+05 | 3.95E+02 | 3.1 | NA/FIO |
| | % reduction | | -27.7228 | 23.7624 | 67.1287 | 99.9218 | | |
| Aspergillus brasiliensis ATCC 16404 | Mean Count | 9.85E+05 | 1.16E+06 | 1.04E+06 | 1.06E+06 | 6.95E+05 | 0.2 | NA/FIO |
| | % reduction | | -17.2589 | -5.0761 | -7.6142 | 29.4416 | | |

| Organism [ATCC #] | $T_0$ | $T_{day\ 7}$ | $T_{day\ 33}$ | day 33 % reduction of initial spike |
|---|---|---|---|---|
| S. aureus [6578] | $1.58 \times 10^3$ | $6.0 \times 10^2$ | $3.0 \times 10^1$ | 98.1% |
| E. coli [8739] | $2.34 \times 10^3$ | $6.8 \times 10^2$ | $1.1 \times 10^2$ | 95.3% |
| P. aeruginosa [9027] | $1.48 \times 10^3$ | <10 | <10 | 99.4% |
| C. albicans (yeast) [10231] | $4.5 \times 10^2$ | <10 | <10 | 98.0% |
| A. brasiliensis (mold) [16404] | $3.3 \times 10^2$ | $1.2 \times 10^2$ | $3.0 \times 10^1$ | 90.9% |

Control sample: <10

Results; 7-day exposure at 20-25 C: (Counts in colony forming units/g)

Example 15

Low Guanosine Diet Enhances Efficacy of Oseltamivir in Treating and Reducing Mortality from Pandemic Influenza Virus.

The inventor has discovered that low guanosine diets can dramatically and surprisingly enhance the efficacy of oseltamivir and other neuraminidase inhibitors for treatment and prevention of viral influenza, including pandemic influenza, and other viruses.

The $LD_{50}$ and $LD_{90}$ were determined for Influenza A/Ca/04/2009 (H1N1) virus in adult C57BL/6 mice on a low guanosine diet, and the effectiveness of oseltamivir was confirmed. Mouse adapted influenza A/California/04/2009 (H1N1pdm) was amplified in Madin-Darby canine kidney cells.

There were initially 10 mice per infection group; however, mice found dead the day of the viral infection were excluded from the results. Survival was based on body weight loss cutoffs of <30% of initial weight. Group A was fed the control diet (Harlan mouse lab diet), and Group B was fed a low guanosine diet, (Purina Mills #5755). Oseltamivir was given to both groups IP, BID for five days beginning four hours pre-infection. At 21 days post-infection, 4/10 (40%) of the mice in Group A (control diet) survived, and 9/9 (100%) of the mice in group B (low guanosine diet) survived. This demonstrated that a low guanosine diet more than doubled the efficacy of oseltamivir in preventing death from pandemic influenza virus.

Example 16

Prevention and Mitigation of West Nile Virus Disease by a Low Guanosine Diet Administered 0-4 Weeks Before Infection in Mice Introduction This experiment demonstrated that feeding a low-nucleotide diet (low guanosine diet) to mice before infection with West Nile Virus demonstrated a significant preventive effect on the disease.

Reduction of the nucleotide pool available for DNA and RNA synthesis has been demonstrated to reduce the replication of both microbes and lymphocytes. Nucleotides and their precursors come from two sources—nutrition and cellular synthetic pathways.

The current study uses a series of experimental groups with different times for pre-feeding, which are expected to show a range of effects. This allowed us to study the preventive effects of diet on West Nile Virus Disease.

Materials and Methods

Animals: C57BL/6 mice, greater than 7 weeks of age, from Charles River Laboratories.

Viruses: WN02 stock (KERN) grown in C6/36 mosquito cells was used. Viral cultures were first confirmed to be mycoplasma-free using the PlasmoTest kit Diets: Pellet TestDiets™ were obtained from Purina Mills. The low nucleotide diet was #5755 and the control diet was #5008.

Infectious cell culture assay: The virus titer in tissues were assayed using the virus yield assay where a specific volume of tissue homogenate was added to the first tube of a series of dilution tubes. Serial dilutions were made and added to Vero cells. Six days later the viral cytopathic effect (CPE) was used to identify the end-point of infection. Four replicates were used to calculate the infectious doses.

Experimental Design

See Table. Adult C57BL/6 female mice were randomized to the groups. All mice were fed diet with nucleotides (Purina Diet 5008) beginning at 4 weeks before viral challenge, except for mice in groups 7 and 2 fed low nucleotide diet (Purina Diet 5755). At 0, −1, and −2 weeks before viral challenge, diets of mice in groups 1, 3, 5, and 2 were changed to low-nucleotide diets (Table 1). Overall, the effects of low-nucleotide diet on WNV disease were evaluated when initiated on 0, 1, 2, and 4 weeks before viral challenge. The assigned diets were fed until the end on the study 21 days after viral challenge.

Sera collected at day 3 and spleen and kidney tissues at day 6 in group-B mice were assayed for WNV infectious titers. Survival, whole body weight, and disease signs were monitored throughout the experiment to day 21.

TABLE 1

Experimental design.

| Mice per group | Group # | Infected WNV, sham | Compound | Diet initiation |
|---|---|---|---|---|
| 20 | 1A | WNV | Diet 5755 low nucleotides | −0 weeks before challenge |
| 10 | 1B | WNV | Diet 5755 low nucleotides | −0 weeks before challenge |
| 20 | 3A | WNV | Diet 5755 low nucleotides | −1 weeks before challenge |
| 10 | 3B | WNV | Diet 5755 low nucleotides | −1 weeks before challenge |
| 20 | 5A | WNV | Diet 5755 low nucleotides | −2 weeks before challenge |
| 10 | 5B | WNV | Diet 5755 low nucleotides | −2 weeks before challenge |
| 20 | 7A | WNV | Diet 5755 low nucleotides | −4 weeks before challenge |
| 10 | 7B | WNV | Diet 5755 low nucleotides | −4 weeks before challenge |
| 20 | 9A | WNV | Diet 5008 with nucleotides | −4 weeks before challenge |
| 10 | 9B | WNV | Diet 5008 with nucleotides | −4 weeks before challenge |
| 5 | 2 | Sham | Diet 5755 low nucleotides | −4 weeks before challenge |
| 5 | 4 | Sham | Diet 5008 with nucleotides | −4 weeks before challenge |

Results and Discussion

To interpret the data, we consider the potential mechanism of action of a nucleotide-free diet. The hypothesized effect is that virus replication would be reduced and disease would be less in mice with reduced reserves of nucleotides, because the virus would not have the nucleotides sufficient to fully replicate. The other effect is increased immunosuppression in mice with nucleotide-free diets. The outcome of these two effects could counteract each other, i.e., there could be reduced viral replication, but increased immunosuppression to allow for increased viral replication. Additionally, increased immunosuppression could reduce neuropathogenesis and disease development.

The mortality of mice fed the low nucleotide diet were statistically lower ($P<0.05$) than the mortality of the control diet group, except for the mortality of mice fed the low nucleotide diet beginning at the time of infection. Importantly, even the low nucleotide diet administered at the time of infection appeared to have a lower mortality than the control diet even though it was not statistically lower.

The percentage of mice free of neurological disease appeared to roughly mirror the survival curves. The kidney infectious WNV titers (6 dpi) from mice administered low nucleotide diet at −2, −1, and 0 weeks relative to viral challenge were statistically lower ($P<0.01$) using the Dunnett's multiple comparison test.

Interestingly, serum and spleen titers from mice administered the nucleotide-free diet at the time of viral challenge were the only titers to be statistically different compare to those of mice administered the control diet. This suggests that the nucleotide pools change very rapidly in response to diet, even rapidly enough to observe effects when diet is administered at the time of viral challenge. Perhaps immunosuppression occurred in mice administered one week or longer before viral challenge to elevate viral titers above those of mice treated at the time of viral challenge.

Conclusions

The mortality of mice fed the low nucleotide diet before infection were statistically lower (P<0.05) than the mortality of the control diet group, except for the mortality of mice fed the low nucleotide diet beginning at the time of infection. This demonstrated the preventive effect of the low nucleotide diet on West Nile disease.

Example 17

Prevention and Mitigation of West Nile Virus Disease by a Low Guanosine Diet Administered 2 Days Before Infection in Mice Introduction This experiment demonstrated that a low nucleotide diet (low guanosine diet) administered 2 days before infection with West Nile Virus could prevent and/or mitigate the disease.

Materials and Methods

Animals: C57BL/6 mice, greater than 7 weeks of age, were used (Charles River Laboratories).

Viruses: WN02 stock (KERN) grown in C6/36 mosquito cells dated Oct. 31, 2013 was used. Viral cultures were first confirmed to be mycoplasma-free using the PlasmoTest kit.

Test articles: Pellet TestDiets™ were obtained from Purina Mills. The low nucleotide diet was #5755 and the control diet was #5008. Harlan mouse lab diet routinely fed to mice in this lab was also used as an additional control.

Infectious cell culture assay: The virus titer in tissues were assayed using the virus yield assay where a specific volume of tissue homogenate was added to the first tube of a series of dilution tubes. Serial dilutions were made and added to Vero cells. Six days later the viral cytopathic effect (CPE) was used to identify the end-point of infection. Four replicates were used to calculate the infectious doses.

Experimental Design

Adult C57BL/6 female mice were randomized to the groups (Table 1). All mice were fed a diet with nucleotides (Purina Diet 5008) beginning at 4 weeks before viral challenge, except for groups 13 and 10 that were fed the Harlan diet used routinely in this lab. At −2 days in relation to viral challenge (designated as day 0), the diets from groups designated in Table 1 were changed to low nucleotide diet (Groups Sham-6, WNV-9). The assigned diets were fed until the end on the study 21 days after viral challenge. Survival was monitored throughout the experiment to day 21.

TABLE 2

Experimental design.

| Mice per group | Group # | WNV | Compound | Diet 5008 dpi | Diet 5755 dpi | Regular diet |
|---|---|---|---|---|---|---|
| 15 | WNV-9 | y | low nucleotide diet | −29 to −3 | −2 to 21 | — |
| 15 | WNV-11 | y | diet with nucleotides | −29 to 21 | — | — |
| 15 | WNV-13 | y | Harlan regular diet | — | — | −29 to 21 |
| 5 | Sham-6 | n | low nucleotide diet | −29 to −3 | −2 to 21 | — |
| 5 | Sham-8 | n | diet with nucleotides | −29 to 21 | — | — |
| 5 | Sham-10 | n | Harlan regular diet | — | — | −29 to 21 |

Results

The low nucleotide diet administered 2 days before viral challenge significantly statistically improved survival (P<0.01) Some reduction in neurological disease signs (paralysis and tremor) was also seen.

Conclusions

A low nucleotide diet administered 2 days before viral challenge, significantly statistically improved survival, preventing in a statistically significant manner death, the most serious effect of the disease, and mitigating neurological sequelae of the disease.

Example 18

Experiment Demonstrating Prevention of Zika Virus Infection by Mycophenolic Acid In Vitro An experiment was carried out as specified in Example 8. In a Zika Prevention Trial, MPA was pre-incubated with human cells 4 hours or 24 hours before Zika virus infection. In the VYR assays, MPA reduced virus to zero in Huh7 cells pre-incubated with drug for 24 hrs.

The data leading to this assessment is shown in the following table:

TABLE 3

Prevention of Zika virus infection by mycophenolic acid

| Administration Time | Cell Type | 100 | 32 | 10 | Dose w Results MPA µg/ml 3.2 | 1 | 0.32 | 0.1 | None |
|---|---|---|---|---|---|---|---|---|---|
| | | | | | Virus Titer (Log10 CCID50/0.1 ml) | | | | |
| 4 hr pre-incubation | Huh7 cells | 0.67 | 4.5 | 4.5 | 4.5 | 4.5 | 4.5 | 4.5 | 4.5 |
| 24 hr pre-incubation | Huh7 cells | <.67 | <.67 | <.67 | 1.5 | 3.5 | 4.5 | 4.5 | 4.5 |

Note:
The bolded entries <0.67 represent no virus detected.

It is also important to note that at 4 hours preincubation (see reference to Example 8 above) a large effect of mycophenolic acid ($SI_{50}>590$) was seen in the Neutral Red assay, and a beneficial effect was shown in the VYR assay ($SI_{90}>2.3$).

Conclusion: Mycophenolic acid was shown to completely prevent infection by Zika virus when given 24 hours before infection, and strongly mitigated the infection when given 4 hours before the infection.

Example 19

Prevention and Mitigation of Pandemic Influenza Infection by Mycophenolate Mofetil (Prodrug of Mycophenolic Acid) and a Low Nucleotide Diet in Mice

Introduction

Reduction of the nucleotide pool available for DNA and RNA synthesis has been demonstrated to decrease the replication of both microbes and lymphocytes. Nucleotides and their precursors come from two sources, nutrition and cellular synthetic pathways. Mycophenolic acid (MPA) inhibits the synthesis of guanosine nucleotides.

We previously titrated the influenza A/Ca/04/2009 (H1N1) virus strain in C57BL/6 mice on a low nucleotide diet, determined the LD50 and LD90, and confirmed an effective dose of oseltamivir to be used as a positive control. For the current study we evaluated the efficacy of MPA against the recently developed mouse model of H1N1 infection in C57BL/6 mice maintained on a low nucleotide diet. Dosing and route was based on the human equivalent dose of mycophenolate mofetil (MMF), the prodrug form of MPA that is often used in humans because of its increased bioavailability. We also evaluated MMF in mice fed a standard diet to establish the importance of nucleotide restriction in the diet.

Materials and Methods

Animals: Female 18-20 g C57BL/6 mice from Charles River Laboratories (Wilmington, MA). Groups of animals were maintained on either standard rodent chow or low nucleotide rodent chow and tap water ad libitum for 7 days prior to virus challenge and continued throughout the study.

Virus: Mouse adapted influenza A/California/04/2009 (H1N1pdm). The virus stock was amplified in Madin-Darby canine kidney (MDCK) cells.

Compound: Mycophenolate mofetil (MMF) from Sigma. MMF was prepared in 0.5% carboxymethyl cellulose (CMC) for oral administration (PO). Oseltamivir phosphate (hereafter referred to as oseltamivir, which was used as a positive control) was obtained from Roche (Palo Alto, CA) as a powder, and prepared in sterile saline for intraperitoneal (IP) injection.

Experiment design: See Table. Mice were anesthetized by IP injection of ketamine/xylazine followed by intranasal exposure to a 75 µl suspension of influenza virus. The infectious inoculum of virus was prepared for administration at dilutions of 1:18,000 and 1:12,000 of the virus stock, corresponding to virus challenge doses of 210 and 320 50% cell culture infectious doses (CCID50) used for infection of the low nucleotide diet group of mice and the standard diet group respectively. MMF treatments and the 0.5% CMC placebo were administered PO twice daily (bid) for 6 days. Oseltamivir treatments were given IP bid for 5 days, starting at 4 h pre-infection. There were initially 10 mice per infection group, however, 8 mice were found dead the day of the viral infection and were excluded from the results (see Table 1). Survival was based on body weight loss cutoffs of <30% of initial weight.

Statistical analysis of the data: Survival curves were compared by the Mantel-Cox log-rank test. Mean day of death (MDD) comparisons were made by one-way ANOVA with Dunnett's multiple comparisons test. Differences in the number of survivors between compound-treated and placebo groups were analyzed by the Fisher's exact (two-tailed) test. Calculations were made using Prism 7.0 (GraphPad Software, San Diego, CA).

Results

In the present study, we evaluated the efficacy of MMF against an influenza A/California/04/2009 (H1N1pdm) infection in C57BL/6 mice fed either a low nucleotide diet or the standard mouse chow diet for 7 days prior to virus challenge and continued throughout the study.

1. In the mice fed the standard diet, MMF given at 40 and 4 mg/kg/day significantly ($P<0.05$) increased the Mean Day of Death (MDD) compared to the placebo-treated animals.

2. In mice fed the low nucleotide diet, treatment with 4 mg/kg/day MMF provided significant ($P<0.05$) protection when compared to the placebo-treated group

Conclusions

The results indicate that C57BL/6 mice fed a low nucleotide diet for 7 days prior to challenge with Pandemic Influenza Virus [influenza A/California/04/2009 (H1N1pdm) strain] had improved survival outcome at the dose of 4 mg/kg/day MMF bid for 6 days beginning 4 h pre-infection.

While the disclosure has been described in detail and with reference to specific examples thereof, it will be apparent to one skilled in the art that various changes and modifications can be made therein without departing from the spirit and scope thereof.

What is claimed is:

1. A method of preventing and/or treating a viral infection in a patient, the method comprising the steps of:
    selecting a patient in need of preventing and/or treating a viral infection;
    administering to the patient at least one agent selected from the group consisting of minocycline, doxycycline, tetracycline, tetracycline derivatives, and combinations thereof,
    wherein the viral infection is prevented and/or treated in the patient.

2. The method of claim 1 wherein the viral infection is selected from the group consisting of West Nile virus, Respiratory Syncytial Virus, Zika virus, Norovirus, Influenza, Adenovirus 5, HPV 11, Lassa Fever virus, Powassan virus, Rift Valley virus, and combinations thereof.

3. The method of claim 1, wherein the at least one agent is present in a pharmaceutical composition further comprising at least one pharmaceutically acceptable excipient.

4. The method of claim 3, wherein the pharmaceutical composition is formulated or manufactured in a dosage form selected from the group consisting of a liquid, an elixir, an aerosol, a spray, a powder, a tablet, a pill, a capsule, a gel, a geltab, a nanosuspension, a nanoparticle, an extended-release dosage form, a topical formulation, and combinations thereof.

5. The method of claim 4, wherein the patient is administered more than one agent, and the more than one agents are in the same dosage form.

6. The method of claim 5, wherein the dosage forms are administered to the patient on a regimen of one, two, three, four, five, six, or doses per day.

7. The method of claim 4, wherein the patient is administered more than one agent, and the more than one agents are in separate dosage forms.

8. The method of claim 7, wherein the dosage forms are administered to the patient on a regimen of one, two, three, four, five, six, or doses per day.

* * * * *